US006265187B1

(12) United States Patent
Scott et al.

(10) Patent No.: US 6,265,187 B1
(45) Date of Patent: Jul. 24, 2001

(54) RECOMBINANT ENDOTOXIN-NEUTRALIZING PROTEINS

(75) Inventors: Randal W. Scott, Mountain View; Marian N. Marra, Redwood City, both of CA (US)

(73) Assignee: Incyte Pharmaceuticals, Inc., Palo Alto, CA (US)

(*) Notice: Subject to any disclaimer, the term of this patent is extended or adjusted under 35 U.S.C. 154(b) by 0 days.

(21) Appl. No.: 08/431,517

(22) Filed: May 1, 1995

Related U.S. Application Data

(62) Continuation-in-part of application No. PCT/US94/04709, filed on Apr. 29, 1994, and a continuation-in-part of application No. 07/915,720, filed as application No. PCT/US91/05758 on Aug. 13, 1991, now Pat. No. 5,770,694, which is a continuation-in-part of application No. 07/681,551, filed on Apr. 5, 1991, now Pat. No. 5,171,739, which is a continuation-in-part of application No. 07/567,016, filed on Aug. 13, 1990, now abandoned, which is a continuation-in-part of application No. 07/468,696, filed on Jan. 22, 1990, now Pat. No. 5,089,274, which is a continuation-in-part of application No. 07/310,842, filed on Feb. 14, 1989, now abandoned, said application No. PCT/US94/04709, is a continuation-in-part of application No. 08/165,717, filed on Dec. 10, 1993, now abandoned, which is a continuation-in-part of application No. 08/056,292, filed on Apr. 30, 1993, now abandoned, which is a continuation-in-part of application No. 07/567,016, which is a continuation-in-part of application No. 07/468,696, which is a continuation-in-part of application No. 07/310,842.

(51) Int. Cl.$^7$ .................. C12N 15/09; C12N 15/00; C12P 21/06; A61K 51/00
(52) U.S. Cl. ................. 435/69.3; 435/69.1; 435/320.1; 424/1.11; 424/1.57; 536/23.1
(58) Field of Search .................. 424/1.11, 1.57; 536/23.1; 435/320.1, 69.1

(56) References Cited

U.S. PATENT DOCUMENTS

| | | | |
|---|---|---|---|
| 5,171,739 | 12/1992 | Scott ..................................... | 514/12 |
| 5,234,912 | 8/1993 | Marra et al. ........................... | 514/21 |
| 5,308,834 | 5/1994 | Scott et al. ............................. | 514/12 |
| 5,334,584 | 8/1994 | Scott et al. ............................. | 514/12 |
| 5,348,942 | 9/1994 | Little, II et al. . | |
| 5,458,874 | * 10/1995 | Pereira et al. ....................... | 424/85.1 |
| 5,643,570 | * 7/1997 | Theogan et al. .................. | 424/134.1 |

FOREIGN PATENT DOCUMENTS

| | | |
|---|---|---|
| 0272489 | 6/1988 | (EP) . |
| 0372130 | 6/1990 | (EP) . |
| WO 89/01486 | 2/1989 | (WO) . |
| WO 90/09183 | 8/1990 | (WO) . |
| WO 92/03535 | 3/1992 | (WO) . |
| WO 93/05797 | 4/1993 | (WO) . |
| WO 93/06228 | 4/1993 | (WO) . |
| WO 93/23434 | 11/1993 | (WO) . |
| 9418323 | * 8/1994 | (WO) ............................ C12N/15/62 |
| WO 95/00641 | 1/1995 | (WO) . |

OTHER PUBLICATIONS

Au–Young, J., et al. 1995. "A novel LBP–BPI fusion protein with in vivo efficacy and longer half–life," *J. Endotoxin Res.* 2:209–212.
Weiss, J. et al. (1975), "Partial Characterization and Purification of a Rabbit Granulocyte Factor that Increases Permeability of *Escherichia coli*," *J. Clin. Invest.* 55:33–42.
Morrison et al. (1976), "Binding of Polymyxin B to the Lipid A Portion of Bacterial Lipopolysaccharides," *Immunochemistry* 13:813–818.
Morrison et al. (1978), "The Effects of Bacterial Endotoxins on Host Mediation Systems," *Am. J. Pathol.* 93(2):527–617.
Weiss et al. (1978), "Purification and Characterization of a Potent Bactericidal and Membrane Active Protein from the Granules of Human Polymorphonuclear Leukoyctes," *J. Biol. Chem.* 253:2664–2672.
Elsbach et al. (1979), "Separation and Purification of a Potent Bactericidal/Permeability–increasing Protein and a Closely Associated Phospholipase A$_2$ from Rabbit Polymorphonuclear Leukocytes," *J. Biol. Chem.* 254:11000–11009.
Ziegler et al., "Treatment of gram–negative bacteremia and shock with human antiserum to a mutant *Escherichia coli*," (1982) *N. Engl. J. Med.* 307:1225–1230.
Weiss et al. (1982), "Killing of Gram–Negative Bacteria by Polymorphonuclear Leukocytes," *Am. Society Clin. Invest.* 69:959–970.
Weiss et al. (1982), "Sensitivity of K1–Encapsulated *Escherichia coli* to Killing by the Bactericidal/Permeability–Increasing Protein of Rabbit and Human Neutrophils," *Infect. Immun.* 38:1149–1153.
Weiss et al. (1983), "Role of Charge and Hydrophobic Interactions in the Action of the Bactericidal/Permeability–Increasing Protein of Neutrophils on Gram–negative Bacteria," *J. Clin. Invest.* 71:540–549.
Muello et al. (1983), "The Role Endotoxin in the Action of the Bactericidal/Permeability Increasing Neutrophil Protein on the Bacterial Envelope," *Clinical Research* 31(2):371A.

(List continued on next page.)

Primary Examiner—James Housel
Assistant Examiner—Padma Baskar
(74) Attorney, Agent, or Firm—McAndrews, Held & Malloy, Ltd.

(57) ABSTRACT

In general, the invention features a recombinant endotoxin-neutralizing polypeptide (RENP) characterized by (i) an amino acid sequence, (ii) an amino acid sequence and structure that facilitates selective and specific binding to lipopolysaccharide and (iii) once bound to the lipopolysaccharide, provides endotoxin-neutralizing activity. Preferably, the RENP is composed of an amino acid sequence similar to, but not identical to, an amino acid sequence of BPI, LBP, or both. Preferably, the RENP contains an LPS-binding domain derived from the amino acid sequence of BPI, LBP, or both. Preferably, the RENPs are covalently bound to a molecule which enhances the half-life of the polypeptide. The RENPs of the invention can be used in pharmaceutical compositions for therapeutic and prophylactic regimens, as well as in various in vitro and in vivo diagnostic methods.

12 Claims, 39 Drawing Sheets

OTHER PUBLICATIONS

Shenep et al. (1984), "Kinetics of Endotoxin Release During Antibiotic Therapy For Experimental Gram–Negative Bacterial Sepsis," *J. Infect. Dis.* 150(3):380–388.

Shafer et al. (1984), "Cationic Antimicrobial Proteins Isolated from Human Neutrophil Granulocytes in the Presence of Diisopropyl Fluorophosphate," *Infection and Immunity* 45:29–35.

Weiss et al. (1984), "The Role of Lipopolysaccharides in the Action of the Bactericidal/Permeability–Increasing Neutrophil Protein on the Bacterial Envelope," *J. Immunol.* 132(6):3109–15.

Duma, R.J., (1985), "Gram–Negative Bacillary Infections," *Am. J. of Med.* 78(Suppl. 6A):154–164.

Weiss et al. (1985), "Oxygen–Independent Intracellular and Oxygen–Dependent Extracellular Killing of *Escherichia coli* S15 by Human Polymorphonuclear Leukocytes," *The American Society of Clinical Investigation, Inc.* 76:206–212.

Weiss et al. (1985), "The Bactericidal/Permeability–Increasing Protein of Neutrophils Retains its Biological Activities After Cleavage by Neutrophil Proteases," *Clinical Research* 33(2):567(A).

Tobias et al. (1986), "Isolation of a Lipopolysaccharide–Binding Acute Phase Reactant from Rabbit Serum," *J. Exp. Med.* 164:777–793.

Hovde et al. (1986), "Characterization of a Protein from Normal Human Polymorphonuclear Leukocytes with Bactericidal Activity Against *Pseudomonas Aeruginosa*," *Infection and Immunity* 54:142–148.

Weiss et al. (1986), "Environmental Modulation of Lipopolysaccharide Chain Length . . . ," *Infection and Immunity* 51:594–599.

Ooi et al. (1987), "A 25–KDa $NH_2$–Terminal Fragment Carries all the Antibacterial Activities of the Human Neutrophil 60–KDa Bactericidal/Permeability–Increasing Protein," *J. Biol. Chem.* 262(31):14891–94.

Bone et al. (1987), "A Controlled Clinical Trial of High–Dose Methylprednisolone in the Treatment of Severe Sepsis and Septic Shock," *N. Engl. J. of Med.* 317(11):653–658.

Weiss et al. (1987), "Cellular and Subcellular Localization of the Bactericidal/Permeability–Increasing Protein of Neutrophils," *BA* 83(9):86173.

Spitznagel et al. (1987), "A Monoclonal Antibody that Inhibits the Antimicrobial Action of a 57 KD Cationic Protein of Human Polymorphonuclear Leukocytes," *J. Immunol.* 139:1291–1296.

Farley et al. (1987), "Antimicrobial Binding of a Radiolabeled Cationic Neutrophil Granule Protein," *Infection and Immunity* 55:1536–1539.

Weiss et al. (1987), "Cellular and Subcellular Localization of the Bactericidal/Permeability–Increasing Protein of Neutrophils," *Blood* 69(2):652–659.

Harkonen et al. (1988), "Phase I Study of a Murine Monoclonal Anti–Lipid A Antibody in Bacteremic and Nonbacteremic Patients," *Antimicrobial Agents and Chemotherapy* 32:710–716.

Harkonen et al. (1988), "Clinical Studies of Monoclonal Anti–Lipid A Antibody XMMEN–OE5," *Bacterial Endotoxins: Pathophysiological Effects, Clinical Significance, and Pharmacological Control,* Alan R. Liss, Inc., pp. 395–406.

Appelmelk et al. (1988), "Production, Characterization and Biological Effects of Monoclonal Antibodies to Different Parts of the Gram–Negative Lipopolysaccharide Core Region," *Bacterial Endotoxins: Pathophysiological Effects, Clinical Significance, and Pharmacological Control,* Alan R. Liss, Inc., pp. 373–382.

Larrick et al. (1988), "Generation of a Protective Human Monoclonal for the Treatment of Gram–Negative Sepsis," *Bacterial Endotoxins: Pathophysiological Effects, Clinical Significance, and Pharmacological Control,* Alan R. Liss, Inc., pp. 383–393.

Tobias et al. (1988), "A Family of Lipopolysaccharide Binding Proteins Involved in Responses to Gram–Negative Sepsis," *J. Biol. Chem.* 263(27):13479–13481.

Gray et al. (1988), "Cloning of the Gene of the Human BPI Protein," *Clinical Research* 36(3):620A.

Veld et al. (1988), "Effects of the Bactericidal/Permeability–Increasing Protein of Polymorphonuclear Leukocytes on Isolated Bacterial Cytoplasmic Membrane Vesicles," *Infection and Immunity* 56:1203–1208.

Farley et al. (1988), "Lipopolysaccharide Structure Determines Ionic and Hydrophobic Binding of a Cationic Antimicrobial Neutrophil Granule Protein," *Infection and Immunity* 56:1589–1592.

Elsbach et al. (1988), "Bactericidal/Permeability Increasing Protein (BPI) of Granulocytes: Structure and Function," *Bacteria–Host Cell Interaction,* pp. 47–60.

Luckow et al. (1988), "Trends in the Development of Baculovirus Expression Vectors," *Bio/Technology* 6:47–55.

Tobias et al. (1989), "Identification of a Lipid A Binding Site in the Acute Phase Reactant Lipopolysaccharide Binding Protein," *J. Biol. Chem.* 264:10867–10871.

Wright et al. (1989), "Lipopolysaccharide (LPS) Binding Protein opsonizes LPS–Bearing Particles for Recognition by a Novel Receptor on Macrophages," *J. Exp. Med.* 170:1231–1241.

Gray et al. (1989), "Cloning of the cDNA of a Human Neutrophil Bactericidal Protein," *The Journal of Biological Chemistry* 264(16):9505.

Leong et al. (1989), "Cloning of the cDNA of a Human Neutrophil Bactericidal Protein," *J. Cell Biochem. Suppl.* 13:66.

Mannion et al. (1989), "Preferential Binding of the Neutrophil Cytoplasmic Granule–Derived Bactericidal/Permeability Increasing Protein to Target Bacteria: Implications and Use as a Means of Purification," *J. Immuno.* 142:2807–2812.

Marra et al. (1990), "Bactericidal/Permeability–Increasing Protein has Endotoxin–Neutralizing Activity," *J. Immunol.* 144:662–666.

Mannion et al. (1990), "Separation of Sublethal and Lethal Effects of the Bactericidal/Permeability Increasing Protein on *Escherichia coli,*" *J. Clin. Invest.* 85:853–860.

Pereira et al. (1990), "The Ontogeny of a 57–Kd Cationic Antimicrobial Protein of Human Polymorphonuclear Leukocytes: Localization to a Novel Granule Population," *Blood* 76:825–834.

Schumann et al. (1990), "Structure and Function of Lipopolysaccharide Binding Protein," *Science* 249:1429–1431.

Wright et al. (1990), "CD14, a Receptor for Complexes of Lipopolysaccharide (LPS) Binding Protein," *Science* 249:1431.

Larrick et al. (1991), "Complementary DNA Sequence of Rabbit Cap 18—A Unique Lipopolysaccharide Binding Protein," *Biochem. Biophys. Research Communications* 179:170–175.

Ooi et al. (1991), "Endotoxin–Neutralizing Properties of the 25kD N–Terminal Fragment and a Newly Isolated 30 kD C–Terminal Fragment of the 55–60 kD Bactericidal/Permeability–Increasing Protein of Human Neutrophils," *J. Exp. Med.* 174:649–655.

Ziegler et al. (1991), "Treatment of gram–negative bacteremia and septic shock with HA–1A human monoclonal antibody against endotoxin—a randomized, double–blind, placebo–controlled trial," *N. Engl. J. Med.* 324:429–436.

Greenman et al. (1991), "A controlled clinical trial of E5 murine monoclonal IgM antibody to endotoxin in the treatment of gram–negative sepsis," *JAMA* 266:1097–1102.

Baumgartner et al. (1991), "The HA–1A monoclonal antibody for gram–negative sepsis," *N. Engl. J. Med.* 325:279–283.

Marra et al. (1994), "Endotoxin–binding and –neutralizing properties of recombinant bactericidal/permeability–increasing protein and monoclonal antibodies HA–1A and E5," *Critical Care Medicine* 22(4):559–565.

Fisher et al. (1994) "Human neutrophil bactericidal/permeability–increasing protein reduces mortality rate from endotoxin challenge: a placebo–controlled study," *Critical Care Medicine* 22(4):553–558.

Wilde et al. (1994), "Bactericidal/permeability–increasing protein and lipopolysaccharide (LPS)–binding protein," *J. Biol. Chem.* 269(26):17411–17416.

Haran et al. (1995), "Lipopolysaccharide binding protein (LBP) and bactericidal/increasing permeability (BPI) in CAPD during bacterial peritonitis (BP)," *Abstract Reproduction Form,* XIIIth International Congress of Nephrology.

Haran et al. (1995), "Circulating levels of lipopolysaccharide–binding protein, bactericidal/permeability–increasing protein and soluble CD14 in patients with chronic renal failure: effect on binding of LPS to patients' monocytes," *Abstract Reproduction Form,* XIIIth International Congress of Nephrology.

Gray et al. Journal of Biological Chemistry 264(16):9505–9509, 1989.

Gray et al. Clinical Research, 36(3):620A, 1988 (Abstract).

* cited by examiner

```
                                                              -25
Human  LBP-a  (as reported by Schumann et al.)          m
       LBP-b  (correct sequence)                        m
                                                                    g g
                        -20              -10                  t a l
                g a l a h a - l p s i l a l - l t s t p e a l
                g a a l - - l p s - - - - - - - - s t p e a l 10             20              50
Human  LBP-a   A N P G L V A R I T D K G L Q Y A A A Q E G L L A L
       LBP-b   A N P G L V A R I T D K G L Q Y A A A Q E G L L A L 30              40                              70
Human  LBP-a   Q S E L L R I T L P D D F T G D L R I P H V G R G R
       LBP-b   Q S E L L R I T L P D D F T G D L R I P H V G R G R 60
Human  LBP-a   Y E F H S L N I H S C E L L H S A L R P V P G Q Q G
       LBP-b   Y E F H S L N I H S C E L L H S A L R P V P G Q Q G
```

```
                          80                  90                 100
Human LBP-a    L S L S I S D S S I R V Q G R W K V R K S F F K L
Human LBP-b    L S L S I S D S S I R V Q G R W K V R K S F F K L 110                 120
Human LBP-a    Q G S F D V S V K G I S I S V N L L L G S E - S
Human LBP-b    Q G S F D V S V K G I S I S V N L L L G S E - S 130                 140
Human LBP-a    G R P T G C Y L S S C S S D I A D V E V D M S G - D
Human LBP-b    G R P T V T A * * * S S D I A D V E V D M S G - D 150              160              170
Human LBP-a    S G W L L N L F H N Q I E S K F Q K V L E S R I C      25k/30k
Human LBP-b    F G W L L N L F H N Q I E S K F Q K V L E S R I C 180                 190
Human LBP-a    E M I Q K S V S S D L Q P Y L Q T L P V T T E I D
Human LBP-b    E M I Q K S V S S D L Q P Y L Q T L P V T T E I D
```

FIG. 1B

```
                    *200                      210                      220
Human LBP-a    S  F  A  D  I  D  Y  S  L  V  E  A  P  R  A  T  A  Q  M  L  E  V  M  F  K
Human LBP-b    S  F  A  D  I  D  Y  S  L  V  E  A  P  R  A  T  A  Q  M  L  E  V  M  F  K 230                      240                              270
Human LBP-a    G  E  I  F  H  R  N  H  R  S  P  V  T  L  L  A  A  A  -  -  -  -  E  E  H  E  E  G  Y
Human LBP-b    G  E  I  F  H  R  N  H  R  S  P  V  T  L  L  A  A  A  A  V  M  S  L  P  *  *  *  *  *

250                      260                      270
Human LBP-a    N  K  M  V  Y  F  A  I  S  D  Y  V  F  N  T  A  S  L  V  Y  H  E  E  G  Y
Human LBP-b    N  K  M  V  Y  F  A  I  S  D  Y  V  F  N  T  A  S  L  V  Y  H  E  E  G  Y 280                      290
Human LBP-a    L  N  F  S  I  T  D  D  M  I  P  P  D  S  N  I  R  L  T  T  K  S  F  R  P
Human LBP-b    L  N  F  S  I  T  D  D  M  I  P  P  D  S  N  I  R  L  T  T  K  S  F  R  P 300                      310                      320
Human LBP-a    F  V  P  R  L  A  R  L  Y  P  N  M  N  L  E  L  Q  G  S  V  P  S  A  P  L
Human LBP-b    F  V  P  R  L  A  R  L  Y  P  N  M  N  L  E  L  Q  G  S  V  P  S  A  P  L
```

```
             330                340                                     
Human  LBP-a  L N F S P G N L S V D P Y M E I D A F V L L P S S
Human  LBP-b  L N F S P G N L S V D P Y M E I D A F V L L P S S 350                360        370
Human  LBP-a  S K E P V F R L S V A T N V S A T L T F N T S K I
Human  LBP-b  S K E P V F R L S V A T N V S A T L T F N T S K I 390
Human  LBP-a  T G F L K P G K V K V E L K E S K V G L F N A E L
Human  LBP-b  T G F L K P G K V K V E L K E S K V G L F N A E L 400                410                420
Human  LBP-a  L E A L L N Y Y I L N T L Y P K F N D K L A E G F
Human  LBP-b  L E A L L N Y Y I L N T F * P K F N D K L A E G F 430                440
Human  LBP-a  P L P L L K R V Q L Y D L G L Q I H K D F L F L G
Human  LBP-b  P L P L L K R V Q L Y D L G L Q I H K D F L F L G 450        456
Human  LBP-a  A N V Q Y M R V
Human  LBP-b  A N V Q Y M R V
```

| FIGURE 3A |
|-----------|
| FIGURE 3B |
| FIGURE 3C |
| FIGURE 3D |

BPI cDNA

```
  1  CAG GCC TTG AGG TTT TGG CAG CTC TGG AGG ATG AGA GAG AAC ATG GCC      48
  1                                             Met Arg Glu Asn Met Ala    6

49  AGG GGC CCT TGC AAC GCG CCG AGA TGG GTG TCC CTG ATG CTC GTC           96
  7  Arg Gly Pro Cys Asn Ala Pro Arg Trp Val Ser Leu Met Leu Val          22

97  GCC ATA GGC ACC GCC GTG ACA GCG GCC AAC CCT GGC GTC GTG GTC         144
 23  Ala Ile Gly Thr Ala Val Thr Ala Ala Asn Pro Gly Val Val Val          38

145  AGG ATC TCC CAG AAG GGC CTG GAC TAC GCC AGC CAG CAG ACG GCC         192
 39  Arg Ile Ser Gln Lys Gly Leu Asp Tyr Ala Ser Gln Gln Thr Ala          54

193  GCT CTG CAG AAG GAG CTG AAG AGG ATT CCT GAC TAC TCA GAC             240
 55  Ala Leu Gln Lys Glu Leu Lys Arg Ile Pro Asp Tyr Ser Asp             70

241  AGC TTT AAG ATC AAG CAT CTT GGG AAG GGG CAT TAT AGC TTC TAC AGC     288
 71  Ser Phe Lys Ile Lys His Leu Gly Lys Gly His Tyr Ser Phe Tyr Ser     86

289  ATG GAC ATC CGT GAA TTC CAG CTT CCC AGT TCC CAG ATA AGC ATG GTG     336
 87  Met Asp Ile Arg Glu Phe Gln Leu Pro Ser Ser Gln Ile Ser Met Val    102
```

```
337  CCC AAT GTG GGC CTT AAG TTC TCC ATC AGC AAC GCC AAT ATC AAG ATC  384
103  Pro Asn Val Gly Leu Lys Phe Ser Ile Ser Asn Ala Asn Ile Lys Ile  118

385  AGC GGG AAA TGG AAG GCA CAA AAG AGA TTC TTA AAA ATG AGC GGC AAT  432
119  Ser Gly Lys Trp Lys Ala Gln Lys Arg Phe Leu Lys Met Ser Gly Asn  134

433  TTT GAC CTG AGC ATA GAA GGC ATG TCC ATT TCG GCT GAT CTG AAG CTG  480
135  Phe Asp Leu Ser Ile Glu Gly Met Ser Ile Ser Ala Asp Leu Lys Leu  150

481  GGC AGT ACC CCC ACG GGC AAG TCA ATC ACC TGC AGC TGC AGC TGC AGC  528
151  Gly Ser Asn Pro Thr Gly Lys Ser Ile Thr Cys Ser Cys Cys Ser Cys  166

529  AGC AGT CAC GTG CAC GTG CTC TTC TTC CAC ATC TCA AAG AGC AAA GTC  576
167  Ser Ser His Val His Val Leu Phe Phe His Ile Ser Lys Ser Lys Val  182

577  GGG TGG CTG ATC CAA AGC CAG GTC TGC GAG CAC AAA ATT GAG TCT CGA  624
183  Gly Trp Leu Ile Gln Ser Gln Val Cys Glu His Lys Ile Glu Ser Arg  198

625  AAC AAG ATG AAC AGC CAA CCT TAT TTC CAG AAA GTG ACC AAT TCT GTA TCC  672
199  Asn Lys Met Asn Ser Gln Pro Tyr Phe Gln Lys Val Thr Asn Ser Val Ser  214

673  TCC AAG CTG CAA CCT TAT CAG ACT CCA GTA ATG ACC AAA ATA  720
215  Ser Lys Leu Gln Pro Tyr Gln Thr Pro Val Met Thr Lys Ile  230

721  GAT TCT GTG GCT GGA ATC AAC AAT TAT GGT CTG GTG GCA CCT CCA GCA ACC  768
231  Asp Ser Val Ala Gly Ile Asn Asn Tyr Gly Leu Val Ala Pro Pro Ala Thr  246
```

| | | | | | | | | | |
|---|---|---|---|---|---|---|---|---|---|
| 769 | ACG | GCT | GAG | ACC | CTG | GAT | GTA | CAG | ATG | AAG | GGG | GAG | TTT | TAC | AGT | GAG | 816 |
| 247 | Thr | Ala | Glu | Thr | Leu | Asp | Val | Gln | Met | Lys | Gly | Glu | Phe | Tyr | Ser | Glu | 262 |
| 817 | AAC | CAC | CAC | AAT | CCA | CCT | TTT | GCT | CCA | GTG | ATG | GAG | TTT | CCC | 864 |
| 263 | Asn | His | His | Asn | Pro | Pro | Phe | Ala | Pro | Val | Met | Glu | Phe | Pro | 278 |
| 865 | GCT | GCC | CAT | GAC | CGC | ATG | GTA | TCA | GGC | CTC | TAC | GAC | TAC | TTC | TTC | 912 |
| 279 | Ala | Ala | His | Asp | Arg | Met | Val | Ser | Gly | Leu | Tyr | Asp | Tyr | Phe | Phe | 294 |
| 913 | AAC | ACA | GCC | GGG | CTT | GTA | TAC | CAA | GAG | GCT | GGG | GTC | TTG | AAG | ATG | ACC | 960 |
| 295 | Asn | Thr | Ala | Gly | Leu | Val | Tyr | Gln | Glu | Ala | Gly | Val | Leu | Lys | Met | Thr | 310 |
| 961 | CTT | AGA | GAT | GAC | ATT | CCA | AAG | GAG | TCC | CAA | TTT | CGA | CTG | ACA | ACC | 1008 |
| 311 | Leu | Arg | Asp | Asp | Ile | Pro | Lys | Glu | Ser | Gln | Phe | Arg | Leu | Thr | Thr | 326 |
| 1009 | AAG | TTC | TTT | GGA | ACC | TTC | CTA | CCT | GAG | GTG | GCC | AAG | TTT | CCC | AAC | 1056 |
| 327 | Lys | Phe | Phe | Gly | Thr | Phe | Leu | Pro | Glu | Val | Ala | Lys | Phe | Pro | Asn | 342 |
| 1057 | ATG | AAG | ATA | CAG | CAT | GTC | TCA | GCC | ACC | TCC | TGG | CAC | CCA | AAG | CTG | TCT | 1104 |
| 343 | Met | Lys | Ile | Gln | His | Val | Ser | Ala | Thr | Ser | Pro | His | Pro | Lys | Leu | Ser | 358 |
| 1105 | GTG | CAG | CCC | ACC | CTT | CTT | ACC | TTC | TAC | CCT | GCT | GAT | GTC | CAG | GCC | 1152 |
| 359 | Val | Gln | Pro | Thr | Leu | Leu | Thr | Phe | Tyr | Pro | Ala | Val | Asp | Val | Gln | Ala | 374 |
| 1153 | CTT | GCC | GTC | CTC | CCC | AAC | TCC | TCC | ATG | TCC | GCT | TTC | CTC | TTC | ATT | GGC | 1200 |
| 375 | Leu | Ala | Val | Leu | Pro | Asn | Ser | Ser | Met | Ser | Ala | Ser | Leu | Phe | Ile | Gly | 390 |
| 1201 | ATG | CAC | ACA | ACT | GGT | TCC | ATG | GAG | GTC | AGC | GCC | GCC | GAG | TCC | AAC | AGG | CTT | 1248 |
| 391 | Met | His | Thr | Thr | Gly | Ser | Met | Glu | Val | Ser | Ala | Ala | Glu | Ser | Asn | Arg | Leu | 406 |

FIG. 3C

```
1249  GTT GGA GAG CTC AAG CTG GAT AGG CTG CTC CTG GAA CTG AAG CAC TCA  1296
 407  Val Gly Glu Leu Lys Leu Asp Arg Leu Leu Leu Glu Leu Lys His Ser   422

1297  AAT ATT GGC CCC TTC GTT GAA TTG CTG CAG GAT ATC ATG AAC TAC       1344
 423  Asn Ile Gly Pro Phe Val Glu Leu Leu Gln Asp Ile Met Asn Tyr       438

1345  ATT GTA CCC ATT CTT GTG CTT CCC AGG GTT AAC CTA GAG CAG AAA       1392
 439  Ile Val Pro Ile Leu Val Leu Pro Arg Val Asn Leu Glu Gln Lys       454

1393  GGC TTC CCT CTC CCG ACG GCC AGA GTC CAG CTC TAC AAC GTA GTG       1440
 455  Gly Phe Pro Leu Pro Thr Ala Arg Val Gln Leu Tyr Asn Val Val       470

1441  CTT CAG CCT CAC CAG AAC TTC CTG CTG GGT GCA GAC GTT GTC TAT       1488
 471  Leu Gln Pro His Gln Asn Phe Leu Leu Gly Ala Asp Val Val Tyr       486

1489  AAA TGA AGG CAC CAG CAG GGG TGC CGG CTG GGG TCA GCC GCA CCT GTT CCT  1536
 487  Lys ***                                                              488

1537  GAT GGG CTG TGG GGC ACC AAG AAT CCT CTC CAG                      1584

1585  ATC TTA ACC AAG AGC CCC TTG CAA ACT TCT TCG ACT CAG ATT CAG AAA  1632

1633  TGA TCT AAA CAC GAG GAA ACA TTA TTC ATT GGA AAA GTG CAT GGT GTG  1680

1681  TAT TTT AGG GAT TAT GAG CTT CTT TCA AGG GCT AAG GCT GCA GAG ATA  1728

1729  TTT CCT CCA GGA ATC GTG TTT CAA TTG TAA CCA AGA AAT TTC CAT TTG  1776

1777  TGC TTC ATG AAA AAA AAC TTC TGG TTT TTT TCA TGT G                1813
```

FIG. 3D

Human LBP    Expression clone

|  |  |  |  |  |  |  |  |  |  |  |  |  |  |  |  |  |
|---|---|---|---|---|---|---|---|---|---|---|---|---|---|---|---|---|
| 1<br>1 | GCT<br>NheI | AGC | CCA | CTG | CAC | TGG | GAA | TCT | AGG | ATG<br>Met | GGG<br>Gly | GCC<br>Ala | TTG<br>Leu | GCC<br>Ala | AGA<br>Arg | GCC<br>Ala | 48<br>7 |
| 49<br>8 | CTG<br>Leu | CCG<br>Pro | TCC<br>Ser | ATA<br>Ile | CTG<br>Leu | CTG<br>Leu | GCA<br>Ala | TTG<br>Leu | CTG<br>Leu | CTT<br>Leu | ACG<br>Thr | TCC<br>Ser | ACC<br>Thr | CCA<br>Pro | GAG<br>Glu | GCT<br>Ala | 96<br>23 |
| 97<br>24 | CTG<br>Leu | GGT<br>Gly | GCC<br>Ala | AAC<br>Asn | CCC<br>Pro | GGC<br>Gly | TTG<br>Leu | GTC<br>Val | GCC<br>Ala | AGG<br>Arg | ATC<br>Ile | ACC<br>Thr | GAC<br>Asp | AAG<br>Lys | GGA<br>Gly | CTG<br>Leu | 144<br>39 |
| 145<br>40 | CAG<br>Gln | TAT<br>Tyr | GCG<br>Ala | GCC<br>Ala | CAG<br>Gln | GAG<br>Glu | GGG<br>Gly | CTA<br>Leu | TTG<br>Leu | GCT<br>Ala | CTG<br>Leu | CAG<br>Gln | AGT<br>Ser | GAG<br>Glu | CTG<br>Leu | CTC<br>Leu | 192<br>55 |
| 193<br>56 | AGG<br>Arg | ATC<br>Ile | ACG<br>Thr | CTG<br>Leu | CCT<br>Pro | GAC<br>Asp | TTC<br>Phe | ACC<br>Thr | GGG<br>Gly | GAC<br>Asp | TTG<br>Leu | AGG<br>Arg | ATC<br>Ile | CCC<br>Pro | CAC<br>His | GTC<br>Val | 240<br>71 |
| 241<br>72 | GGC<br>Gly | CGT<br>Arg | GGG<br>Gly | CGC<br>Arg | TAT<br>Tyr | GAG<br>Glu | TTC<br>Phe | CAC<br>His | AGC<br>Ser | GCG<br>Ala | CTG<br>Leu | AGG<br>Arg | AAC<br>Asn | ATC<br>Ile | CAC<br>His | TGT<br>Cys | GAG<br>Glu | 288<br>87 |
| 289<br>88 | CTT<br>Leu | CAC<br>His | CGT<br>Arg | TCT<br>Ser | GCG<br>Ala | CTG<br>Leu | AGG<br>Arg | CCT<br>Pro | GTC<br>Val | CCT<br>Pro | GGC<br>Gly | CAG<br>Gln | GGC<br>Gly | CTG<br>Leu | AGT<br>Ser | CTC<br>Leu | 336<br>103 |
| 337<br>104 | AGC<br>Ser | ATC<br>Ile | TCC<br>Ser | GAC<br>Asp | TCC<br>Ser | TCC<br>Ser | ATC<br>Ile | CGG<br>Arg | GTC<br>Val | CAG<br>Gln | GGC<br>Gly | AGG<br>Arg | TGG<br>Trp | AAG<br>Lys | GTG<br>Val | CGC<br>Arg | 384<br>119 |
| 385<br>120 | AAG<br>Lys | TCA<br>Ser | TTC<br>Phe | TTC<br>Phe | AAA<br>Lys | CTA<br>Leu | CAG<br>Gln | GGC<br>Gly | TCC<br>Ser | TTT<br>Phe | GAT<br>Asp | GTC<br>Val | AGT<br>Ser | GTC<br>Val | AAG<br>Lys | GGC<br>Gly | 432<br>135 |
| 433<br>136 | ATC<br>Ile | AGC<br>Ser | ATT<br>Ile | TCG<br>Ser | AAC<br>Asn | GTC<br>Val | TCG<br>Ser | AAC<br>Asn | CTC<br>Leu | CTG<br>Leu | TTG<br>Leu | GGC<br>Gly | AGC<br>Ser | GAG<br>Glu | TCC<br>Ser | GGG<br>Gly | AGG<br>Arg | 480<br>151 |

| FIGURE 4A |
| FIGURE 4B |
| FIGURE 4C |

FIG. 4A

| | | | | | | | | | | | | | | | | |
|---|---|---|---|---|---|---|---|---|---|---|---|---|---|---|---|---|
| 481 | CCC | ACA | GTT | ACT | GCC | TCC | AGC | TGC | AGT | GAC | ATC | GCT | GAC | GTG | GAG | 528 |
| 152 | Pro | Thr | Val | Thr | Ala | Ser | Ser | Cys | Ser | Asp | Ile | Ala | Asp | Val | Glu | 167 |
| 529 | GTG | GAC | ATG | TCG | GGA | GAC | TTC | GGG | TGG | CTG | AAC | CTC | TTC | CAC | AAC | 576 |
| 168 | Val | Asp | Met | Ser | Gly | Asp | Phe | Gly | Trp | Leu | Asn | Leu | Phe | His | Asn | 183 |
| 577 | CAG | ATT | GAG | TCC | AAG | TTC | AAA | GTA | CTG | GAG | AGC | AGG | ATT | TGC | GAA | 624 |
| 184 | Gln | Ile | Glu | Ser | Lys | Phe | Lys | Val | Leu | Glu | Ser | Arg | Ile | Cys | Glu | 199 |
| 625 | ATG | ATC | CAG | AAA | TCG | GTG | TCC | GAT | CTA | CAG | CCT | TAT | CTC | CAA | ACT | 672 |
| 200 | Met | Ile | Gln | Lys | Ser | Val | Ser | Asp | Leu | Gln | Pro | Tyr | Leu | Gln | Thr | 215 |
| 673 | CTG | CCA | GTT | ACA | GAG | ATT | GAC | AGT | TTC | GCC | GAT | ATT | GAT | TAT | AGC | 720 |
| 216 | Leu | Pro | Val | Thr | Glu | Ile | Asp | Ser | Phe | Ala | Asp | Ile | Asp | Tyr | Ser | 231 |
| 721 | TTA | GTG | GAA | GCC | CCT | CGG | GCA | ACA | GCC | CAG | ATG | CTG | GAG | GTG | TTT | 768 |
| 232 | Leu | Val | Glu | Ala | Pro | Arg | Ala | Thr | Ala | Gln | Met | Leu | Glu | Val | Phe | 247 |
| 769 | AAG | GGT | GAA | ATC | TTT | CAT | CGT | AAC | CAC | CGT | TCT | CCA | GTT | ACC | CTC | CTT | 816 |
| 248 | Lys | Gly | Glu | Ile | Phe | His | Arg | Asn | His | Arg | Ser | Pro | Val | Thr | Leu | Leu | 263 |
| 817 | GCT | GCA | GTC | ATG | AGC | CTT | CCT | GAG | GAA | CAC | AAC | AAA | ATG | GTC | TAC | TTT | 864 |
| 264 | Ala | Ala | Val | Met | Ser | Leu | Pro | Glu | Glu | His | Asn | Lys | Met | Val | Tyr | Phe | 279 |
| 865 | GCC | ATC | TCG | GAT | TAT | GTC | TTC | AAC | ACG | GCC | AGC | CTG | GTT | TAT | CAT | GAG | 912 |
| 280 | Ala | Ile | Ser | Asp | Tyr | Val | Phe | Asn | Thr | Ala | Ser | Leu | Val | Tyr | His | Glu | 295 |
| 913 | GAA | GGA | TAT | CTG | AAC | TTC | TCC | ATC | ACA | GAT | GAC | ATG | ATA | CCG | CCT | GAC | 960 |
| 296 | Glu | Gly | Tyr | Leu | Asn | Phe | Ser | Ile | Thr | Asp | Asp | Met | Ile | Pro | Pro | Asp | 311 |
| 961 | TCT | AAT | ATC | CGA | AAG | ACC | ACC | AAG | TCC | TTC | CGA | CCC | TTC | GTC | CCA | CGG | 1008 |
| 312 | Ser | Asn | Ile | Arg | Lys | Thr | Thr | Lys | Ser | Phe | Arg | Pro | Phe | Val | Pro | Arg | 327 |

FIG. 4B

```
1009 TTA GCC AGG CTC TAC CCC AAC ATG AAC CTG GAA CTC CAG GGA TCA GTG 1056
 328 Leu Ala Arg Leu Tyr Pro Asn Met Asn Leu Glu Leu Gln Gly Ser Val  343

1057 CCC TCT GCT CCG CTC CTG AAC TTC AGC CCT GGG AAT CTG TCT GTG GAC 1104
 344 Pro Ser Ala Pro Leu Leu Asn Phe Ser Pro Gly Asn Leu Ser Val Asp  359

1105 CCC TAT ATG GAG ATA GAT GCC TTT GTG CTC TTG CCC AGC TCC AGC AAG 1152
 360 Pro Tyr Met Glu Ile Asp Ala Phe Val Leu Leu Pro Ser Ser Ser Lys  375

1153 GAG CCT GTC TTC CGG CTC AGT GCC GTG ACT AAT GTC TCC GCC ACC TTG 1200
 376 Glu Pro Val Phe Arg Leu Ser Val Ala Thr Asn Val Ser Ala Thr Leu  391

1201 ACC TTC AAT ACC AGC AAG ATC ACT GGG TTC CTG AAG CCA GGA AAG GTA 1248
 392 Thr Phe Asn Thr Ser Lys Ile Thr Gly Phe Leu Lys Pro Gly Lys Val  407

1249 AAA GTG GAA CTG AAA GAA TCC CTA TTC GGA GTT TTC AAT GCA GAG CTG 1296
 408 Lys Val Glu Leu Lys Glu Ser Leu Phe Gly Val Leu Asn Ala Glu Leu  423

1297 TTG GAA GCG CTC CTC CTC AAC TAT TAC ATC CTT AAC ACC TTC TAC CCC AAG 1344
 424 Leu Glu Ala Leu Leu Leu Asn Tyr Tyr Ile Leu Asn Thr Phe Tyr Pro Lys  439

1345 TTC AAT GAT AAG TTG GCC GAA GGG CTG GCC CTT CCC CTT CCT CTG AAG CGT 1392
 440 Phe Asn Asp Lys Leu Ala Glu Gly Leu Ala Phe Pro Leu Pro Leu Lys Arg  455

1393 GTT CAG CTC TAC GAC CTT TAT GGG CTG CAG ATC CAT AAG GAC TTC CTG TTC 1440
 456 Val Gln Leu Tyr Asp Leu Tyr Gly Leu Gln Ile His Lys Asp Phe Leu Phe  471

1441 TTG GGT GCC AAT GTC CAA TAC ATG AGA GTT TGA CAA GAA AGA TGA 1488
 472 Leu Gly Ala Asn Val Gln Tyr Met Arg Val Val ***                 482

1489 AGC TTG CTC GAG                                                 1500
      Xhol
```

| FIGURE 5A |
| FIGURE 5B |
| FIGURE 5C |
| FIGURE 5D |
| FIGURE 5E |
| FIGURE 5F |

| | Mouse LBP | Rabbit LBP | Human LBP | Human BPI | Bovine BPI |
|---|---|---|---|---|---|

FIG. 5B

```
              110                                        120                                         130
Rabbit LBP    K Q S N F D L Y V K G L T I S V H L L V L G S E - S S *
Human  LBP    Q G S N F D V S V K E G I S S N D L L K L L G S - S S *
Human  BPI    S G N F D F D L L V I E G M S I S A D G L L G N P T S *
Bovine BPI    G - - F D L D P A - - G I I L S G L A G L - P A - S * 150

* D F N S V L V * K G L T I S V H L L V L G S E - S S *
              * D F S N V L V * K E G I S S N D L L K L L G S - S S *
              * D F N F D L L * V I E G M S I S A D G L L G N P T S *
              * D F D - - G L * I L S G L A G L - P A - S *

Rabbit LBP    G G R P T V T T C T S S * S S C C S - D G G - E - D K S
Human  LBP    G G R P T T T A C S S * S S C C S - D D H G I A N Q - D
Human  BPI    G G K P T T T C C T T - S S C C S * D H G I - N T - S K
Bovine BPI    * G G G G * * T T T T * * T T T T * * S S S S *           160
                                                    170
Rabbit LBP    L E E W L L L L - W G L W L F R H V E L D I M - - S G -
Human  LBP    L G G L L L L - G W L F Q H V V E D M - I S K S -
Human  BPI    L V G L L W L - V W L F L H R V H V - R I - - G S -
Bovine BPI    L L L L * * * L L L L *

Rabbit LBP    R E E L - Q M I - Q T - E K N S A V T S S H L K K R L F L A R K A L A S S S -
Human  LBP    E E E - V Q N - I - Q T R L F R K H R K Q K N S E S S R -
Human  BPI    E E V - I V V - Z - K I - L F F L L L R R K R - Q K R N S S -
Bovine BPI    * V V V * * Q Q Q * * - L L L * * - N N Q Q -           180
                                                    190
Rabbit LBP    * E A V T S S H L * Q L Q P Y L * F Q T L P V T T * T Q I D *
Human  LBP    K Q T S S D L P Q L P Y L F Q T L P V T T K E D
Human  BPI    K N T S S K L P Y L F Q T L P V M T K I D
Bovine BPI    * S S S K L * Q L Q P Y F * - F Q - L P V T - * K L - L D *   25k/30k

FIG. 5C
```

Note: The above alignment is approximate; the figure shows a multiple sequence alignment of Rabbit LBP, Human LBP, Human BPI, and Bovine BPI from residues ~110 to ~190.

```
      10         20         30         40         50         60
MGALARALPS ILLALLLTST PEALGANPGL VARITDKGLQ YAAQEGLLAL QSELLRITLP
      70         80         90        100        110        120
DFTGDLRIPH VGRGRYEFHS LNIHSCELLH SALRPVPGQG LSLSISDSSI RVQGRWKVRK
     130        140        150        160        170        180
SFFKLQGSFD VSVKGISISV NLLIGSESSG RPTVTASSCS SDIADVEVDM SGDLGWLLNL
     190        200        210        220    25/30  230        240
FHNQIESKFQ KVLESRICEM IQKSVSSDLQ PYLQTLPVTT EIDSVAGINY GLVAPPATTA
     250        260        270        280        290        300
ETLDVQMKGE FYSENHHNPP PFAPPVMEFP AAHDRMVYLG LSDYFFNTAG LVYQEAGVLK
     310        320        330        340        350        360
MTLRDDMIPK ESKFRLTTKF FGTFLPEVAK KFPNMKIQIH VSASTPPHLS VQPTGLTFYP
     370        380        390        400        410        420
AVDVQALAVL PNSSLASLFL IGMHTTGSME VSAESNRLVG ELKLDRLLLE LKHSNIGPFP
     430        440        450        460        470        479
VELLQDIMNY IVPILVLPRV NEKLQKGFPL PTPARVQLYN VVLQPHQNFL LFGADVVYK*  -C
```

FIG. 6

5mg/kg compound injected i.v. at t=0

SEQUENCE LISTING

<160> NUMBER OF SEQ ID NOS: 17

<210> SEQ ID NO 1
<211> LENGTH: 1500
<212> TYPE: DNA
<213> ORGANISM: human
<220> FEATURE:
<221> NAME/KEY: CDS
<222> LOCATION: (28)..(1470)
<221> NAME/KEY: mat_peptide
<222> LOCATION: (103)..(1470)
<223> OTHER INFORMATION: Note:  human LBP-b DNA and amino acid sequence
      (Figure 1 and 4); Figure 1 has His at position -20

<400> SEQUENCE: 1

```
gctagcccac tgcactggga atctagg atg ggg gcc ttg gcc aga gcc ctg ccg      54
                              Met Gly Ala Leu Ala Arg Ala Leu Pro
                                -25                 -20 tcc ata ctg ctg gca ttg ctg ctt acg tcc acc cca gag gct ctg ggt       102
Ser Ile Leu Leu Ala Leu Leu Leu Thr Ser Thr Pro Glu Ala Leu Gly
       -15                 -10                  -5                -1 gcc aac ccc ggc ttg gtc gcc agg atc acc gac aag gga ctg cag tat       150
Ala Asn Pro Gly Leu Val Ala Arg Ile Thr Asp Lys Gly Leu Gln Tyr
  1               5                  10                  15 gcg gcc cag gag ggg cta ttg gct ctg cag agt gag ctg ctc agg atc       198
Ala Ala Gln Glu Gly Leu Leu Ala Leu Gln Ser Glu Leu Leu Arg Ile
             20                  25                  30 acg ctg cct gac ttc acc ggg gac ttg agg atc ccc cac gtc ggc cgt       246
Thr Leu Pro Asp Phe Thr Gly Asp Leu Arg Ile Pro His Val Gly Arg
         35                  40                  45 ggg cgc tat gag ttc cac agc ctg aac atc cac agc tgt gag ctg ctt       294
Gly Arg Tyr Glu Phe His Ser Leu Asn Ile His Ser Cys Glu Leu Leu
 50                  55                  60 cac tct gcg ctg agg cct gtc cct ggc cag ggc ctg agt ctc agc atc       342
His Ser Ala Leu Arg Pro Val Pro Gly Gln Gly Leu Ser Leu Ser Ile
 65                  70                  75                  80 tcc gac tcc tcc atc cgg gtc cag ggc agg tgg aag gtg cgc aag tca       390
Ser Asp Ser Ser Ile Arg Val Gln Gly Arg Trp Lys Val Arg Lys Ser
                 85                  90                  95 ttc ttc aaa cta cag ggc tcc ttt gat gtc agt gtc aag ggc atc agc       438
Phe Phe Lys Leu Gln Gly Ser Phe Asp Val Ser Val Lys Gly Ile Ser
             100                 105                 110 att tcg gtc aac ctc ctg ttg ggc agc gag tcc tcc ggg agg ccc aca       486
Ile Ser Val Asn Leu Leu Leu Gly Ser Glu Ser Ser Gly Arg Pro Thr
         115                 120                 125 gtt act gcc tcc agc tgc agc agt gac atc gct gac gtg gag gtg gac       534
Val Thr Ala Ser Ser Cys Ser Ser Asp Ile Ala Asp Val Glu Val Asp
130                 135                 140 atg tcg gga gac ttc ggg tgg ctg ttg aac ctc ttc cac aac cag att       582
Met Ser Gly Asp Phe Gly Trp Leu Leu Asn Leu Phe His Asn Gln Ile
145                 150                 155                 160 gag tcc aag ttc cag aaa gta ctg gag agc agg att tgc gaa atg atc       630
Glu Ser Lys Phe Gln Lys Val Leu Glu Ser Arg Ile Cys Glu Met Ile
                 165                 170                 175 cag aaa tcg gtg tcc tcc gat cta cag cct tat ctc caa act ctg cca       678
Gln Lys Ser Val Ser Ser Asp Leu Gln Pro Tyr Leu Gln Thr Leu Pro
             180                 185                 190 gtt aca aca gag att gac agt ttc gcc gac att gat tat agc tta gtg       726
Val Thr Thr Glu Ile Asp Ser Phe Ala Asp Ile Asp Tyr Ser Leu Val
         195                 200                 205
```

```
gaa gcc cct cgg gca aca gcc cag atg ctg gag gtg atg ttt aag ggt      774
Glu Ala Pro Arg Ala Thr Ala Gln Met Leu Glu Val Met Phe Lys Gly
    210                 215                 220 gaa atc ttt cat cgt aac cac cgt tct cca gtt acc ctc ctt gct gca      822
Glu Ile Phe His Arg Asn His Arg Ser Pro Val Thr Leu Leu Ala Ala
225                 230                 235                 240 gtc atg agc ctt cct gag gaa cac aac aaa atg gtc tac ttt gcc atc      870
Val Met Ser Leu Pro Glu Glu His Asn Lys Met Val Tyr Phe Ala Ile
                245                 250                 255 tcg gat tat gtc ttc aac acg gcc agc ctg gtt tat cat gag gaa gga      918
Ser Asp Tyr Val Phe Asn Thr Ala Ser Leu Val Tyr His Glu Glu Gly
            260                 265                 270 tat ctg aac ttc tcc atc aca gat gac atg ata ccg cct gac tct aat      966
Tyr Leu Asn Phe Ser Ile Thr Asp Asp Met Ile Pro Pro Asp Ser Asn
        275                 280                 285 atc cga ctg acc acc aag tcc ttc cga ccc ttc gtc cca cgg tta gcc     1014
Ile Arg Leu Thr Thr Lys Ser Phe Arg Pro Phe Val Pro Arg Leu Ala
    290                 295                 300 agg ctc tac ccc aac atg aac ctg gaa ctc cag gga tca gtg ccc tct     1062
Arg Leu Tyr Pro Asn Met Asn Leu Glu Leu Gln Gly Ser Val Pro Ser
305                 310                 315                 320 gct ccg ctc ctg aac ttc agc cct ggg aat ctg tct gtg gac ccc tat     1110
Ala Pro Leu Leu Asn Phe Ser Pro Gly Asn Leu Ser Val Asp Pro Tyr
                325                 330                 335 atg gag ata gat gcc ttt gtg ctc ctc ccc agc tcc agc aag gag cct     1158
Met Glu Ile Asp Ala Phe Val Leu Leu Pro Ser Ser Ser Lys Glu Pro
            340                 345                 350 gtc ttc cgg ctc agt gtg gcc act aat gtg tcc gcc acc ttg acc ttc     1206
Val Phe Arg Leu Ser Val Ala Thr Asn Val Ser Ala Thr Leu Thr Phe
        355                 360                 365 aat acc agc aag atc act ggg ttc ctg aag cca gga aag gta aaa gtg     1254
Asn Thr Ser Lys Ile Thr Gly Phe Leu Lys Pro Gly Lys Val Lys Val
    370                 375                 380 gaa ctg aaa gaa tcc aaa gtt gga cta ttc aat gca gag ctg ttg gaa     1302
Glu Leu Lys Glu Ser Lys Val Gly Leu Phe Asn Ala Glu Leu Leu Glu
385                 390                 395                 400 gcg ctc ctc aac tat tac atc ctt aac acc ttc tac ccc aag ttc aat     1350
Ala Leu Leu Asn Tyr Tyr Ile Leu Asn Thr Phe Tyr Pro Lys Phe Asn
                405                 410                 415 gat aag ttg gcc gaa ggc ttc ccc ctt cct ctg ctg aag cgt gtt cag     1398
Asp Lys Leu Ala Glu Gly Phe Pro Leu Pro Leu Leu Lys Arg Val Gln
            420                 425                 430 ctc tac gac ctt ggg ctg cag atc cat aag gac ttc ctg ttc ttg ggt     1446
Leu Tyr Asp Leu Gly Leu Gln Ile His Lys Asp Phe Leu Phe Leu Gly
        435                 440                 445 gcc aat gtc caa tac atg aga gtt tgaggacaag aaagatgaag cttgctcgag    1500
Ala Asn Val Gln Tyr Met Arg Val
    450                 455

<210> SEQ ID NO 2
<211> LENGTH: 481
<212> TYPE: PRT
<213> ORGANISM: human
<223> OTHER INFORMATION: Note:  human LBP-b DNA and amino acid sequence

<400> SEQUENCE: 2

Met Gly Ala Leu Ala Arg Ala Leu Pro Ser Ile Leu Leu Ala Leu Leu
-25                 -20                 -15                 -10

Leu Thr Ser Thr Pro Glu Ala Leu Gly Ala Asn Pro Gly Leu Val Ala
            -5                  -1  1                   5
```

-continued

```
Arg Ile Thr Asp Lys Gly Leu Gln Tyr Ala Ala Gln Glu Gly Leu Leu
         10                  15                  20

Ala Leu Gln Ser Glu Leu Leu Arg Ile Thr Leu Pro Asp Phe Thr Gly
         25                  30                  35

Asp Leu Arg Ile Pro His Val Gly Arg Gly Arg Tyr Glu Phe His Ser
 40                  45                  50                  55

Leu Asn Ile His Ser Cys Glu Leu Leu His Ser Ala Leu Arg Pro Val
                 60                  65                  70

Pro Gly Gln Gly Leu Ser Leu Ser Ile Ser Asp Ser Ser Ile Arg Val
             75                  80                  85

Gln Gly Arg Trp Lys Val Arg Lys Ser Phe Phe Lys Leu Gln Gly Ser
         90                  95                 100

Phe Asp Val Ser Val Lys Gly Ile Ser Ile Ser Val Asn Leu Leu Leu
    105                 110                 115

Gly Ser Glu Ser Ser Gly Arg Pro Thr Val Thr Ala Ser Ser Cys Ser
120                 125                 130                 135

Ser Asp Ile Ala Asp Val Glu Val Asp Met Ser Gly Asp Phe Gly Trp
                140                 145                 150

Leu Leu Asn Leu Phe His Asn Gln Ile Glu Ser Lys Phe Gln Lys Val
            155                 160                 165

Leu Glu Ser Arg Ile Cys Glu Met Ile Gln Lys Ser Val Ser Ser Asp
        170                 175                 180

Leu Gln Pro Tyr Leu Gln Thr Leu Pro Val Thr Thr Glu Ile Asp Ser
    185                 190                 195

Phe Ala Asp Ile Asp Tyr Ser Leu Val Glu Ala Pro Arg Ala Thr Ala
200                 205                 210                 215

Gln Met Leu Glu Val Met Phe Lys Gly Glu Ile Phe His Arg Asn His
                220                 225                 230

Arg Ser Pro Val Thr Leu Leu Ala Ala Val Met Ser Leu Pro Glu Glu
            235                 240                 245

His Asn Lys Met Val Tyr Phe Ala Ile Ser Asp Tyr Val Phe Asn Thr
        250                 255                 260

Ala Ser Leu Val Tyr His Glu Glu Gly Tyr Leu Asn Phe Ser Ile Thr
    265                 270                 275

Asp Asp Met Ile Pro Pro Asp Ser Asn Ile Arg Leu Thr Thr Lys Ser
280                 285                 290                 295

Phe Arg Pro Phe Val Pro Arg Leu Ala Arg Leu Tyr Pro Asn Met Asn
                300                 305                 310

Leu Glu Leu Gln Gly Ser Val Pro Ser Ala Pro Leu Leu Asn Phe Ser
            315                 320                 325

Pro Gly Asn Leu Ser Val Asp Pro Tyr Met Glu Ile Asp Ala Phe Val
        330                 335                 340

Leu Leu Pro Ser Ser Lys Glu Pro Val Phe Arg Leu Ser Val Ala
    345                 350                 355

Thr Asn Val Ser Ala Thr Leu Thr Phe Asn Thr Ser Lys Ile Thr Gly
360                 365                 370                 375

Phe Leu Lys Pro Gly Lys Val Lys Val Glu Leu Lys Glu Ser Lys Val
                380                 385                 390

Gly Leu Phe Asn Ala Glu Leu Leu Glu Ala Leu Leu Asn Tyr Tyr Ile
            395                 400                 405

Leu Asn Thr Phe Tyr Pro Lys Phe Asn Asp Lys Leu Ala Glu Gly Phe
        410                 415                 420

Pro Leu Pro Leu Leu Lys Arg Val Gln Leu Tyr Asp Leu Gly Leu Gln
```

-continued

```
            425                 430                 435
Ile His Lys Asp Phe Leu Phe Leu Gly Ala Asn Val Gln Tyr Met Arg
440                 445                 450                 455

Val

<210> SEQ ID NO 3
<211> LENGTH: 1813
<212> TYPE: DNA
<213> ORGANISM: human
<220> FEATURE:
<221> NAME/KEY: CDS
<222> LOCATION: (31)..(1491)
<221> NAME/KEY: mat_peptide
<222> LOCATION: (124)..(1491)
<223> OTHER INFORMATION: BPI cDNA and amino acid sequence (Figure 3)

<400> SEQUENCE: 3
caggccttga ggttttggca gctctggagg atg aga gag aac atg gcc agg ggc       54
                                Met Arg Glu Asn Met Ala Arg Gly
                                -30                 -25 cct tgc aac gcg ccg aga tgg gtg tcc ctg atg gtg ctc gtc gcc ata      102
Pro Cys Asn Ala Pro Arg Trp Val Ser Leu Met Val Leu Val Ala Ile
        -20                 -15                 -10 ggc acc gcc gtg aca gcg gcc gtc aac cct ggc gtc gtg gtc agg atc      150
Gly Thr Ala Val Thr Ala Ala Val Asn Pro Gly Val Val Val Arg Ile
    -5                  -1   1                   5 tcc cag aag ggc ctg gac tac gcc agc cag cag ggg acg gcc gct ctg      198
Ser Gln Lys Gly Leu Asp Tyr Ala Ser Gln Gln Gly Thr Ala Ala Leu
 10                  15                  20                  25 cag aag gag ctg aag agg atc aag att cct gac tac tca gac agc ttt      246
Gln Lys Glu Leu Lys Arg Ile Lys Ile Pro Asp Tyr Ser Asp Ser Phe
                 30                  35                  40 aag atc aag cat ctt ggg aag ggg cat tat agc ttc tac agc atg gac      294
Lys Ile Lys His Leu Gly Lys Gly His Tyr Ser Phe Tyr Ser Met Asp
             45                  50                  55 atc cgt gaa ttc cag ctt ccc agt tcc cag ata agc atg gtg ccc aat      342
Ile Arg Glu Phe Gln Leu Pro Ser Ser Gln Ile Ser Met Val Pro Asn
         60                  65                  70 gtg ggc ctt aag ttc tcc atc agc aac gcc aat atc aag atc agc ggg      390
Val Gly Leu Lys Phe Ser Ile Ser Asn Ala Asn Ile Lys Ile Ser Gly
     75                  80                  85 aaa tgg aag gca caa aag aga ttc tta aaa atg agc ggc aat ttt gac      438
Lys Trp Lys Ala Gln Lys Arg Phe Leu Lys Met Ser Gly Asn Phe Asp
 90                  95                 100                 105 ctg agc ata gaa ggc atg tcc att tcg gct gat ctg aag ctg ggc agt      486
Leu Ser Ile Glu Gly Met Ser Ile Ser Ala Asp Leu Lys Leu Gly Ser
                110                 115                 120 aac ccc acg tca ggc aag ccc acc atc acc tgc tcc agc tgc agc agc      534
Asn Pro Thr Ser Gly Lys Pro Thr Ile Thr Cys Ser Ser Cys Ser Ser
            125                 130                 135 cac atc aac agt gtc cac gtg cac atc tca aag agc aaa gtc ggg tgg      582
His Ile Asn Ser Val His Val His Ile Ser Lys Ser Lys Val Gly Trp
        140                 145                 150 ctg atc caa ctc ttc cac aaa aaa att gag tct gcg ctt cga aac aag      630
Leu Ile Gln Leu Phe His Lys Lys Ile Glu Ser Ala Leu Arg Asn Lys
155                 160                 165 atg aac agc cag gtc tgc gag aaa gtg acc aat tct gta tcc tcc aag      678
Met Asn Ser Gln Val Cys Glu Lys Val Thr Asn Ser Val Ser Ser Lys
170                 175                 180                 185 ctg caa cct tat ttc cag act ctg cca gta atg acc aaa ata gat tct      726
Leu Gln Pro Tyr Phe Gln Thr Leu Pro Val Met Thr Lys Ile Asp Ser
```

|  |  |  |  |  |  |  |  |  |  |  |  |  |  |  |  |
|---|---|---|---|---|---|---|---|---|---|---|---|---|---|---|---|
|  |  |  |  | 190 |  |  |  |  | 195 |  |  |  |  | 200 |  |
| gtg | gct | gga | atc | aac | tat | ggt | ctg | gtg | gca | cct | cca | gca | acc | acg | gct |
| Val | Ala | Gly | Ile | Asn | Tyr | Gly | Leu | Val | Ala | Pro | Pro | Ala | Thr | Thr | Ala |
|  |  |  | 205 |  |  |  |  | 210 |  |  |  |  | 215 |  |  |

774 gag acc ctg gat gta cag atg aag ggg gag ttt tac agt gag aac cac     822
Glu Thr Leu Asp Val Gln Met Lys Gly Glu Phe Tyr Ser Glu Asn His
        220                 225                 230 cac aat cca cct ccc ttt gct cca cca gtg atg gag ttt ccc gct gcc     870
His Asn Pro Pro Pro Phe Ala Pro Pro Val Met Glu Phe Pro Ala Ala
        235                 240                 245 cat gac cgc atg gta tac ctg ggc ctc tca gac tac ttc ttc aac aca     918
His Asp Arg Met Val Tyr Leu Gly Leu Ser Asp Tyr Phe Phe Asn Thr
250                 255                 260                 265 gcc ggg ctt gta tac caa gag gct ggg gtc ttg aag atg acc ctt aga     966
Ala Gly Leu Val Tyr Gln Glu Ala Gly Val Leu Lys Met Thr Leu Arg
                270                 275                 280 gat gac atg att cca aag gag tcc aaa ttt cga ctg aca acc aag ttc    1014
Asp Asp Met Ile Pro Lys Glu Ser Lys Phe Arg Leu Thr Thr Lys Phe
            285                 290                 295 ttt gga acc ttc cta cct gag gtg gcc aag aag ttt ccc aac atg aag    1062
Phe Gly Thr Phe Leu Pro Glu Val Ala Lys Lys Phe Pro Asn Met Lys
        300                 305                 310 ata cag atc cat gtc tca gcc tcc acc ccg cca cac ctg tct gtg cag    1110
Ile Gln Ile His Val Ser Ala Ser Thr Pro Pro His Leu Ser Val Gln
        315                 320                 325 ccc acc ggc ctt acc ttc tac cct gcc gtg gat gtc cag gcc ctt gcc    1158
Pro Thr Gly Leu Thr Phe Tyr Pro Ala Val Asp Val Gln Ala Leu Ala
330                 335                 340                 345 gtc ctc ccc aac tcc tcc ctg gct tcc ctc ttc ctg att ggc atg cac    1206
Val Leu Pro Asn Ser Ser Leu Ala Ser Leu Phe Leu Ile Gly Met His
                350                 355                 360 aca act ggt tcc atg gag gtc agc gcc gag tcc aac agg ctt gtt gga    1254
Thr Thr Gly Ser Met Glu Val Ser Ala Glu Ser Asn Arg Leu Val Gly
                365                 370                 375 gag ctc aag ctg gat agg ctg ctc ctg gaa ctg aag cac tca aat att    1302
Glu Leu Lys Leu Asp Arg Leu Leu Leu Glu Leu Lys His Ser Asn Ile
        380                 385                 390 ggc ccc ttc ccg gtt gaa ttg ctg cag gat atc atg aac tac att gta    1350
Gly Pro Phe Pro Val Glu Leu Leu Gln Asp Ile Met Asn Tyr Ile Val
        395                 400                 405 ccc att ctt gtg ctg ccc agg gtt aac gag aaa cta cag aaa ggc ttc    1398
Pro Ile Leu Val Leu Pro Arg Val Asn Glu Lys Leu Gln Lys Gly Phe
410                 415                 420                 425 cct ctc ccg acg ccg gcc aga gtc cag ctc tac aac gta gtg ctt cag    1446
Pro Leu Pro Thr Pro Ala Arg Val Gln Leu Tyr Asn Val Val Leu Gln
                430                 435                 440 cct cac cag aac ttc ctg ctg ttc ggt gca gac gtt gtc tat aaa        1491
Pro His Gln Asn Phe Leu Leu Phe Gly Ala Asp Val Val Tyr Lys
        445                 450                 455 tgaaggcacc agggtgccg gggctgtca gccgcacctg ttcctgatgg gctgtggggc    1551
accggctgcc tttccccagg gaatcctctc cagatcttaa ccaagagccc cttgcaaact    1611
tcttcgactc agattcagaa atgatctaaa cacgaggaaa cattattcat tggaaaagtg    1671
catggtgtgt attttaggga ttatgagctt ctttcaaggg ctaaggctgc agagatattt    1731
cctccaggaa tcgtgtttca attgtaacca agaaatttcc atttgtgctt catgaaaaaa    1791
aacttctggt tttttttcatg tg                                            1813

```
<210> SEQ ID NO 4
<211> LENGTH: 487
<212> TYPE: PRT
<213> ORGANISM: human
<223> OTHER INFORMATION: BPI cDNA and amino acid sequence (Figure 3)

<400> SEQUENCE: 4

Met Arg Glu Asn Met Ala Arg Gly Pro Cys Asn Ala Pro Arg Trp Val
    -30                 -25                 -20

Ser Leu Met Val Leu Val Ala Ile Gly Thr Ala Val Thr Ala Ala Val
-15                 -10                  -5                  -1   1

Asn Pro Gly Val Val Arg Ile Ser Gln Lys Gly Leu Asp Tyr Ala
                 5                  10                  15

Ser Gln Gly Thr Ala Ala Leu Gln Lys Glu Leu Lys Arg Ile Lys
            20                  25                  30

Ile Pro Asp Tyr Ser Asp Ser Phe Lys Ile Lys His Leu Gly Lys Gly
        35                  40                  45

His Tyr Ser Phe Tyr Ser Met Asp Ile Arg Glu Phe Gln Leu Pro Ser
50                  55                  60                  65

Ser Gln Ile Ser Met Val Pro Asn Val Gly Leu Lys Phe Ser Ile Ser
                70                  75                  80

Asn Ala Asn Ile Lys Ile Ser Gly Lys Trp Lys Ala Gln Lys Arg Phe
                85                  90                  95

Leu Lys Met Ser Gly Asn Phe Asp Leu Ser Ile Glu Gly Met Ser Ile
                100                 105                 110

Ser Ala Asp Leu Lys Leu Gly Ser Asn Pro Thr Ser Gly Lys Pro Thr
            115                 120                 125

Ile Thr Cys Ser Ser Cys Ser Ser His Ile Asn Ser Val His Val His
130                 135                 140                 145

Ile Ser Lys Ser Lys Val Gly Trp Leu Ile Gln Leu Phe His Lys Lys
                150                 155                 160

Ile Glu Ser Ala Leu Arg Asn Lys Met Asn Ser Gln Val Cys Glu Lys
                165                 170                 175

Val Thr Asn Ser Val Ser Ser Lys Leu Gln Pro Tyr Phe Gln Thr Leu
                180                 185                 190

Pro Val Met Thr Lys Ile Asp Ser Val Ala Gly Ile Asn Tyr Gly Leu
                195                 200                 205

Val Ala Pro Pro Ala Thr Thr Ala Glu Thr Leu Asp Val Gln Met Lys
210                 215                 220                 225

Gly Glu Phe Tyr Ser Glu Asn His His Asn Pro Pro Phe Ala Pro
                230                 235                 240

Pro Val Met Glu Phe Pro Ala Ala His Asp Arg Met Val Tyr Leu Gly
                245                 250                 255

Leu Ser Asp Tyr Phe Phe Asn Thr Ala Gly Leu Val Tyr Gln Glu Ala
            260                 265                 270

Gly Val Leu Lys Met Thr Leu Arg Asp Asp Met Ile Pro Lys Glu Ser
275                 280                 285

Lys Phe Arg Leu Thr Thr Lys Phe Phe Gly Thr Phe Leu Pro Glu Val
290                 295                 300                 305

Ala Lys Lys Phe Pro Asn Met Lys Ile Gln Ile His Val Ser Ala Ser
                310                 315                 320

Thr Pro Pro His Leu Ser Val Gln Pro Thr Gly Leu Thr Phe Tyr Pro
            325                 330                 335

Ala Val Asp Val Gln Ala Leu Ala Val Leu Pro Asn Ser Ser Leu Ala
            340                 345                 350
```

```
Ser Leu Phe Leu Ile Gly Met His Thr Thr Gly Ser Met Glu Val Ser
    355                 360                 365

Ala Glu Ser Asn Arg Leu Val Gly Glu Leu Lys Leu Asp Arg Leu Leu
370                 375                 380                 385

Leu Glu Leu Lys His Ser Asn Ile Gly Pro Phe Pro Val Glu Leu Leu
                390                 395                 400

Gln Asp Ile Met Asn Tyr Ile Val Pro Ile Leu Val Leu Pro Arg Val
            405                 410                 415

Asn Glu Lys Leu Gln Lys Gly Phe Pro Leu Pro Thr Pro Ala Arg Val
        420                 425                 430

Gln Leu Tyr Asn Val Val Leu Gln Pro His Gln Asn Phe Leu Leu Phe
    435                 440                 445

Gly Ala Asp Val Val Tyr Lys
450                 455

<210> SEQ ID NO 5
<211> LENGTH: 482
<212> TYPE: PRT
<213> ORGANISM: rabbit
<220> FEATURE:
<223> OTHER INFORMATION: rabbit LBP amino acid (Figure 5)
<221> NAME/KEY: SIGNAL
<222> LOCATION: (1)..(26)
<221> NAME/KEY: CHAIN
<222> LOCATION: (27)..(482)

<400> SEQUENCE: 5

Met Gly Thr Trp Ala Arg Ala Leu Leu Gly Ser Thr Leu Leu Ser Leu
  1               5                  10                  15

Leu Leu Ala Ala Ala Phe Gly Ala Leu Gly Thr Asn Pro Gly Leu Ile
                 20                  25                  30

Thr Arg Ile Thr Asp Lys Gly Leu Glu Tyr Ala Ala Arg Glu Gly Leu
             35                  40                  45

Leu Ala Leu Gln Arg Lys Leu Leu Glu Val Thr Leu Pro Asp Ser Asp
         50                  55                  60

Gly Asp Phe Arg Ile Lys His Phe Gly Arg Ala Gln Tyr Lys Phe Tyr
 65                  70                  75                  80

Ser Leu Lys Ile Pro Arg Phe Glu Leu Leu Arg Gly Thr Leu Arg Pro
                 85                  90                  95

Leu Pro Gly Gln Gly Leu Ser Leu Asp Ile Ser Asp Ala Tyr Ile His
                100                 105                 110

Val Arg Gly Ser Trp Lys Val Arg Lys Ala Phe Leu Arg Leu Lys Asn
            115                 120                 125

Ser Phe Asp Leu Tyr Val Lys Gly Leu Thr Ile Ser Val His Leu Val
        130                 135                 140

Leu Gly Ser Glu Ser Ser Gly Arg Pro Thr Val Thr Thr Ser Ser Cys
145                 150                 155                 160

Ser Ser Asp Ile Gln Asn Val Glu Leu Asp Ile Glu Gly Asp Leu Glu
                165                 170                 175

Glu Leu Leu Asn Leu Leu Gln Ser Gln Ile Asp Ala Arg Leu Arg Glu
                180                 185                 190

Val Leu Glu Ser Lys Ile Cys Arg Gln Ile Glu Glu Ala Val Thr Ala
            195                 200                 205

His Leu Gln Pro Tyr Leu Gln Thr Leu Pro Val Thr Thr Gln Ile Asp
        210                 215                 220

Ser Phe Ala Gly Ile Asp Tyr Ser Leu Met Glu Ala Pro Arg Ala Thr
```

-continued

```
                225                 230                 235                 240
Ala Gly Met Leu Asp Val Met Phe Lys Gly Glu Ile Phe Pro Leu Asp
                245                 250                 255
His Arg Ser Pro Val Asp Phe Leu Ala Pro Ala Met Asn Leu Pro Glu
                260                 265                 270
Ala His Ser Arg Met Val Tyr Phe Ser Ile Ser Asp Tyr Val Phe Asn
                275                 280                 285
Thr Ala Ser Leu Ala Tyr His Lys Ser Gly Tyr Trp Asn Phe Ser Ile
                290                 295                 300
Thr Asp Ala Met Val Pro Ala Asp Leu Asn Ile Arg Arg Thr Thr Lys
305                 310                 315                 320
Ser Phe Arg Pro Phe Val Pro Leu Leu Ala Asn Leu Tyr Pro Asn Met
                325                 330                 335
Asn Leu Glu Leu Gln Gly Thr Val Asn Ser Glu Gln Leu Val Asn Leu
                340                 345                 350
Ser Thr Glu Asn Leu Leu Glu Glu Pro Glu Met Asp Ile Glu Ala Leu
                355                 360                 365
Val Val Leu Pro Ser Ser Ala Arg Glu Pro Val Phe Arg Leu Gly Val
                370                 375                 380
Ala Thr Asn Val Ser Ala Thr Leu Thr Leu Asn Thr Arg Lys Ile Thr
385                 390                 395                 400
Gly Phe Leu Lys Pro Gly Arg Leu Gln Val Glu Leu Lys Glu Ser Lys
                405                 410                 415
Val Gly Gly Phe Asn Val Glu Leu Leu Glu Ala Leu Leu Asn Tyr Tyr
                420                 425                 430
Ile Leu Asn Asn Leu Tyr Pro Lys Val Asn Glu Lys Leu Ala His Arg
                435                 440                 445
Phe Pro Leu Pro Leu Arg His Ile Gln Leu Tyr Asp Leu Leu Leu
                450                 455                 460
Gln Thr His Glu Asn Phe Leu Val Gly Ala Asn Ile Gln Tyr Arg
465                 470                 475                 480
Arg Val

<210> SEQ ID NO 6
<211> LENGTH: 456
<212> TYPE: PRT
<213> ORGANISM: rabbit
<220> FEATURE:
<223> OTHER INFORMATION: rabbit LBP amino acid (Figure 5); mature
      protein sequence

<400> SEQUENCE: 6

Thr Asn Pro Gly Leu Ile Thr Arg Ile Thr Asp Lys Gly Leu Glu Tyr
  1                 5                  10                  15
Ala Ala Arg Glu Gly Leu Leu Ala Leu Gln Arg Lys Leu Leu Glu Val
                 20                  25                  30
Thr Leu Pro Asp Ser Asp Gly Asp Phe Arg Ile Lys His Phe Gly Arg
             35                  40                  45
Ala Gln Tyr Lys Phe Tyr Ser Leu Lys Ile Pro Arg Phe Glu Leu Leu
         50                  55                  60
Arg Gly Thr Leu Arg Pro Leu Pro Gly Gln Gly Leu Ser Leu Asp Ile
 65                  70                  75                  80
Ser Asp Ala Tyr Ile His Val Arg Gly Ser Trp Lys Val Arg Lys Ala
                 85                  90                  95
Phe Leu Arg Leu Lys Asn Ser Phe Asp Leu Tyr Val Lys Gly Leu Thr
```

|     |     |     |     | 100 |     |     |     |     | 105 |     |     |     |     | 110 |     |
| --- | --- | --- | --- | --- | --- | --- | --- | --- | --- | --- | --- | --- | --- | --- | --- |

Ile Ser Val His Leu Val Leu Gly Ser Glu Ser Gly Arg Pro Thr
    115                    120                125

Val Thr Thr Ser Ser Cys Ser Ser Asp Ile Gln Asn Val Glu Leu Asp
130                    135                140

Ile Glu Gly Asp Leu Glu Glu Leu Leu Asn Leu Leu Gln Ser Gln Ile
145                  150              155                160

Asp Ala Arg Leu Arg Glu Val Leu Glu Ser Lys Ile Cys Arg Gln Ile
                165              170                175

Glu Glu Ala Val Thr Ala His Leu Gln Pro Tyr Leu Gln Thr Leu Pro
                180              185                190

Val Thr Thr Gln Ile Asp Ser Phe Ala Gly Ile Asp Tyr Ser Leu Met
                195              200                205

Glu Ala Pro Arg Ala Thr Ala Gly Met Leu Asp Val Met Phe Lys Gly
            210              215              220

Glu Ile Phe Pro Leu Asp His Arg Ser Pro Val Asp Phe Leu Ala Pro
225                    230                235                240

Ala Met Asn Leu Pro Glu Ala His Ser Arg Met Val Tyr Phe Ser Ile
                245              250                255

Ser Asp Tyr Val Phe Asn Thr Ala Ser Leu Ala Tyr His Lys Ser Gly
            260              265              270

Tyr Trp Asn Phe Ser Ile Thr Asp Ala Met Val Pro Ala Asp Leu Asn
        275                280              285

Ile Arg Arg Thr Thr Lys Ser Phe Arg Pro Phe Val Pro Leu Leu Ala
        290                295              300

Asn Leu Tyr Pro Asn Met Asn Leu Glu Leu Gln Gly Thr Val Asn Ser
305                    310                315                320

Glu Gln Leu Val Asn Leu Ser Thr Glu Asn Leu Leu Glu Glu Pro Glu
                325              330                335

Met Asp Ile Glu Ala Leu Val Val Leu Pro Ser Ser Ala Arg Glu Pro
            340              345              350

Val Phe Arg Leu Gly Val Ala Thr Asn Val Ser Ala Thr Leu Thr Leu
        355                360              365

Asn Thr Arg Lys Ile Thr Gly Phe Leu Lys Pro Gly Arg Leu Gln Val
370                    375                380

Glu Leu Lys Glu Ser Lys Val Gly Gly Phe Asn Val Glu Leu Leu Glu
385                    390                395                400

Ala Leu Leu Asn Tyr Tyr Ile Leu Asn Asn Leu Tyr Pro Lys Val Asn
                405              410                415

Glu Lys Leu Ala His Arg Phe Pro Leu Pro Leu Leu Arg His Ile Gln
            420              425              430

Leu Tyr Asp Leu Leu Leu Gln Thr His Glu Asn Phe Leu Leu Val Gly
                435              440              445

Ala Asn Ile Gln Tyr Arg Arg Val
450                    455

```
<210> SEQ ID NO 7
<211> LENGTH: 481
<212> TYPE: PRT
<213> ORGANISM: human
<220> FEATURE:
<223> OTHER INFORMATION: human LBP-a amino acid (Schumann et al.)
      (Figure 1)
<221> NAME/KEY: SIGNAL
<222> LOCATION: (1)..(25)
<221> NAME/KEY: CHAIN
```

<222> LOCATION: (26)..(481)
<223> OTHER INFORMATION: To align with corres. a.a. positions in LBP-b
      sequence, Xaa is inserted at a.a. position corres.
      to 267, 268, 269 & 270 to mark the gap of 4 a.a.
      not present in human LBP-a as shown in Fig. 1

<400> SEQUENCE: 7

```
Met Gly Ala Leu Ala His Ala Leu Pro Ser Ile Leu Ala Leu Leu
 1               5                  10                  15

Leu Thr Ser Thr Pro Glu Ala Leu Gly Ala Asn Pro Gly Leu Val Ala
                 20                  25                  30

Arg Ile Thr Asp Lys Gly Leu Gln Tyr Ala Ala Gln Glu Gly Leu Leu
                 35                  40                  45

Ala Leu Gln Ser Glu Leu Leu Arg Ile Thr Leu Pro Asp Phe Thr Gly
 50                  55                  60

Asp Leu Arg Ile Pro His Val Gly Arg Gly Arg Tyr Glu Phe His Ser
 65                  70                  75                  80

Leu Asn Ile His Ser Cys Glu Leu Leu His Ser Ala Leu Arg Pro Val
                 85                  90                  95

Pro Gly Gln Gly Leu Ser Leu Ser Ile Ser Asp Ser Ser Ile Arg Val
                100                 105                 110

Gln Gly Arg Trp Lys Val Arg Lys Ser Phe Phe Lys Leu Gln Gly Ser
                115                 120                 125

Phe Asp Val Ser Val Lys Gly Ile Ser Ile Ser Val Asn Leu Leu Leu
130                 135                 140

Gly Ser Glu Ser Ser Gly Arg Pro Thr Gly Cys Tyr Leu Ser Cys Ser
145                 150                 155                 160

Ser Asp Ile Ala Asp Val Glu Val Asp Met Ser Gly Asp Ser Gly Trp
                165                 170                 175

Leu Leu Asn Leu Phe His Asn Gln Ile Glu Ser Lys Phe Gln Lys Val
                180                 185                 190

Leu Glu Ser Arg Ile Cys Glu Met Ile Gln Lys Ser Val Ser Ser Asp
                195                 200                 205

Leu Gln Pro Tyr Leu Gln Thr Leu Pro Val Thr Thr Glu Ile Asp Ser
210                 215                 220

Phe Ala Asp Ile Asp Tyr Ser Leu Val Glu Ala Pro Arg Ala Thr Ala
225                 230                 235                 240

Gln Met Leu Glu Val Met Phe Lys Gly Glu Ile Phe His Arg Asn His
                245                 250                 255

Arg Ser Pro Val Thr Leu Leu Ala Ala Xaa Xaa Xaa Xaa Glu Glu
                260                 265                 270

His Asn Lys Met Val Tyr Phe Ala Ile Ser Asp Tyr Val Phe Asn Thr
                275                 280                 285

Ala Ser Leu Val Tyr His Glu Glu Gly Tyr Leu Asn Phe Ser Ile Thr
290                 295                 300

Asp Asp Met Ile Pro Pro Asp Ser Asn Ile Arg Leu Thr Thr Lys Ser
305                 310                 315                 320

Phe Arg Pro Phe Val Pro Arg Leu Ala Arg Leu Tyr Pro Asn Met Asn
                325                 330                 335

Leu Glu Leu Gln Gly Ser Val Pro Ser Ala Pro Leu Leu Asn Phe Ser
                340                 345                 350

Pro Gly Asn Leu Ser Val Asp Pro Tyr Met Glu Ile Asp Ala Phe Val
                355                 360                 365

Leu Leu Pro Ser Ser Ser Lys Glu Pro Val Phe Arg Leu Ser Val Ala
                370                 375                 380
```

```
Thr Asn Val Ser Ala Thr Leu Thr Phe Asn Thr Ser Lys Ile Thr Gly
385                 390                 395                 400

Phe Leu Lys Pro Gly Lys Val Lys Val Glu Leu Lys Glu Ser Lys Val
                405                 410                 415

Gly Leu Phe Asn Ala Glu Leu Leu Glu Ala Leu Leu Asn Tyr Tyr Ile
                420                 425                 430

Leu Asn Thr Leu Tyr Pro Lys Phe Asn Asp Lys Leu Ala Glu Gly Phe
                435                 440                 445

Pro Leu Pro Leu Lys Arg Val Gln Leu Tyr Asp Leu Gly Leu Gln
                450                 455                 460

Ile His Lys Asp Phe Leu Phe Leu Gly Ala Asn Val Gln Tyr Met Arg
465                 470                 475                 480

Val
```

```
<210> SEQ ID NO 8
<211> LENGTH: 456
<212> TYPE: PRT
<213> ORGANISM: human
<220> FEATURE:
<223> OTHER INFORMATION: human LBP-a amino acid (Schumann et al.)
      (Figure 1); mature protein sequence
<223> OTHER INFORMATION: To align with corres. a.a. positions in LBP-b
      sequence, Xaa is inserted at a.a. position corres.
      to 242, 243, 244 & 245 to mark the gap of 4 a.a.
      not present in human LBP-a as shown in Fig. 1

<400> SEQUENCE: 8

Ala Asn Pro Gly Leu Val Ala Arg Ile Thr Asp Lys Gly Leu Gln Tyr
1               5                   10                  15

Ala Ala Gln Glu Gly Leu Leu Ala Leu Gln Ser Glu Leu Leu Arg Ile
                20                  25                  30

Thr Leu Pro Asp Phe Thr Gly Asp Leu Arg Ile Pro His Val Gly Arg
                35                  40                  45

Gly Arg Tyr Glu Phe His Ser Leu Asn Ile His Ser Cys Glu Leu Leu
    50                  55                  60

His Ser Ala Leu Arg Pro Val Pro Gly Gln Gly Leu Ser Leu Ser Ile
65                  70                  75                  80

Ser Asp Ser Ser Ile Arg Val Gln Gly Arg Trp Lys Val Arg Lys Ser
                85                  90                  95

Phe Phe Lys Leu Gln Gly Ser Phe Asp Val Ser Val Lys Gly Ile Ser
                100                 105                 110

Ile Ser Val Asn Leu Leu Leu Gly Ser Glu Ser Ser Gly Arg Pro Thr
                115                 120                 125

Gly Cys Tyr Leu Ser Cys Ser Ser Asp Ile Ala Asp Val Glu Val Asp
    130                 135                 140

Met Ser Gly Asp Ser Gly Trp Leu Leu Asn Leu Phe His Asn Gln Ile
145                 150                 155                 160

Glu Ser Lys Phe Gln Lys Val Leu Glu Ser Arg Ile Cys Glu Met Ile
                165                 170                 175

Gln Lys Ser Val Ser Ser Asp Leu Gln Pro Tyr Leu Gln Thr Leu Pro
                180                 185                 190

Val Thr Thr Glu Ile Asp Ser Phe Ala Asp Ile Asp Tyr Ser Leu Val
                195                 200                 205

Glu Ala Pro Arg Ala Thr Ala Gln Met Leu Glu Val Met Phe Lys Gly
    210                 215                 220

Glu Ile Phe His Arg Asn His Arg Ser Pro Val Thr Leu Leu Ala Ala
```

```
225                 230                 235                 240
Ala Xaa Xaa Xaa Xaa Glu Glu His Asn Lys Met Val Tyr Phe Ala Ile
                245                 250                 255

Ser Asp Tyr Val Phe Asn Thr Ala Ser Leu Val Tyr His Glu Glu Gly
            260                 265                 270

Tyr Leu Asn Phe Ser Ile Thr Asp Asp Met Ile Pro Pro Asp Ser Asn
        275                 280                 285

Ile Arg Leu Thr Thr Lys Ser Phe Arg Pro Phe Val Pro Arg Leu Ala
    290                 295                 300

Arg Leu Tyr Pro Asn Met Asn Leu Glu Leu Gln Gly Ser Val Pro Ser
305                 310                 315                 320

Ala Pro Leu Leu Asn Phe Ser Pro Gly Asn Leu Ser Val Asp Pro Tyr
                325                 330                 335

Met Glu Ile Asp Ala Phe Val Leu Leu Pro Ser Ser Ser Lys Glu Pro
            340                 345                 350

Val Phe Arg Leu Ser Val Ala Thr Asn Val Ser Ala Thr Leu Thr Phe
        355                 360                 365

Asn Thr Ser Lys Ile Thr Gly Phe Leu Lys Pro Gly Lys Val Lys Val
    370                 375                 380

Glu Leu Lys Glu Ser Lys Val Gly Leu Phe Asn Ala Glu Leu Leu Glu
385                 390                 395                 400

Ala Leu Leu Asn Tyr Tyr Ile Leu Asn Thr Leu Tyr Pro Lys Phe Asn
                405                 410                 415

Asp Lys Leu Ala Glu Gly Phe Pro Leu Pro Leu Leu Lys Arg Val Gln
            420                 425                 430

Leu Tyr Asp Leu Gly Leu Gln Ile His Lys Asp Phe Leu Phe Leu Gly
        435                 440                 445

Ala Asn Val Gln Tyr Met Arg Val
    450                 455

<210> SEQ ID NO 9
<211> LENGTH: 84
<212> TYPE: PRT
<213> ORGANISM: mouse
<220> FEATURE:
<223> OTHER INFORMATION: mouse LBP amino acid (Figure 5); partial
      sequence with signal sequence
<221> NAME/KEY: SIGNAL
<222> LOCATION: (1)..(18)
<221> NAME/KEY: CHAIN
<222> LOCATION: (19)..(84)

<400> SEQUENCE: 9

Leu Pro Ser Thr Leu Gly Leu Leu Phe Leu Ser Ile Gln Gly Thr
  1               5                  10                  15

Gly Gly Val Asn Pro Gly Val Val Ala Arg Ile Thr Asp Lys Gly Leu
            20                  25                  30

Ala Tyr Ala Ala Lys Glu Gly Leu Val Ala Leu Gln Arg Glu Leu Tyr
        35                  40                  45

Arg Ile Thr Leu Pro Asp Phe Ser Gly Asp Phe Lys Ile Lys Ala Val
    50                  55                  60

Gly Arg Gly Gln Tyr Glu Phe His Ser Leu Glu Ile Gln Asn Cys Glu
65                  70                  75                  80

Leu Arg Gly Ser

<210> SEQ ID NO 10
<211> LENGTH: 66
```

```
<212> TYPE: PRT
<213> ORGANISM: mouse
<220> FEATURE:
<223> OTHER INFORMATION: mouse LBP amino acid (Figure 5); partial
      sequence

<400> SEQUENCE: 10
```

Val Asn Pro Gly Val Val Ala Arg Ile Thr Asp Lys Gly Leu Ala Tyr
 1               5                  10                  15

Ala Ala Lys Glu Gly Leu Val Ala Leu Gln Arg Glu Leu Tyr Arg Ile
            20                  25                  30

Thr Leu Pro Asp Phe Ser Gly Asp Phe Lys Ile Lys Ala Val Gly Arg
        35                  40                  45

Gly Gln Tyr Glu Phe His Ser Leu Glu Ile Gln Asn Cys Glu Leu Arg
    50                  55                  60

Gly Ser
 65

```
<210> SEQ ID NO 11
<211> LENGTH: 481
<212> TYPE: PRT
<213> ORGANISM: human
<220> FEATURE:
<223> OTHER INFORMATION: human LBP amino acid (Figure 5)
<221> NAME/KEY: SIGNAL
<222> LOCATION: (1)..(25)
<221> NAME/KEY: CHAIN
<222> LOCATION: (26)..(481)

<400> SEQUENCE: 11
```

Met Gly Ala Leu Ala His Ala Leu Pro Ser Ile Leu Ala Leu Leu
 1               5                  10                  15

Leu Thr Ser Thr Pro Glu Ala Leu Gly Ala Asn Pro Gly Leu Val Ala
            20                  25                  30

Arg Ile Thr Asp Lys Gly Leu Gln Tyr Ala Ala Gln Glu Gly Leu Leu
        35                  40                  45

Ala Leu Gln Ser Glu Leu Leu Arg Ile Thr Leu Pro Asp Phe Thr Gly
    50                  55                  60

Asp Leu Arg Ile Pro His Val Gly Arg Gly Arg Tyr Glu Phe His Ser
 65                  70                  75                  80

Leu Asn Ile His Ser Cys Glu Leu Leu His Ser Ala Leu Arg Pro Val
                85                  90                  95

Pro Gly Gln Gly Leu Ser Leu Ser Ile Ser Asp Ser Ser Ile Arg Val
            100                 105                 110

Gln Gly Arg Trp Lys Val Arg Lys Ser Phe Phe Lys Leu Gln Gly Ser
        115                 120                 125

Phe Asp Val Ser Val Lys Gly Ile Ser Ile Ser Val Asn Leu Leu Leu
    130                 135                 140

Gly Ser Glu Ser Ser Gly Arg Pro Thr Val Thr Ala Ser Ser Cys Ser
145                 150                 155                 160

Ser Asp Ile Ala Asp Val Glu Val Asp Met Ser Gly Asp Leu Gly Trp
                165                 170                 175

Leu Leu Asn Leu Phe His Asn Gln Ile Glu Ser Lys Phe Gln Lys Val
            180                 185                 190

Leu Glu Ser Arg Ile Cys Glu Met Ile Gln Lys Ser Val Ser Ser Asp
        195                 200                 205

Leu Gln Pro Tyr Leu Gln Thr Leu Pro Val Thr Thr Glu Ile Asp Ser
    210                 215                 220

```
Phe Ala Asp Ile Asp Tyr Ser Leu Val Glu Ala Pro Arg Ala Thr Ala
225                 230                 235                 240

Gln Met Leu Glu Val Met Phe Lys Gly Glu Ile Phe His Arg Asn His
                245                 250                 255

Arg Ser Pro Val Thr Leu Leu Ala Ala Val Met Ser Leu Pro Glu Glu
                260                 265                 270

His Asn Lys Met Val Tyr Phe Ala Ile Ser Asp Tyr Val Phe Asn Thr
            275                 280                 285

Ala Ser Leu Val Tyr His Glu Glu Gly Tyr Leu Asn Phe Ser Ile Thr
290                 295                 300

Asp Asp Met Ile Pro Pro Asp Ser Asn Ile Arg Leu Thr Thr Lys Ser
305                 310                 315                 320

Phe Arg Pro Phe Val Pro Arg Leu Ala Arg Leu Tyr Pro Asn Met Asn
                325                 330                 335

Leu Glu Leu Gln Gly Ser Val Pro Ser Ala Pro Leu Leu Asn Phe Ser
                340                 345                 350

Pro Gly Asn Leu Ser Val Asp Pro Tyr Met Glu Ile Asp Ala Phe Val
                355                 360                 365

Leu Leu Pro Ser Ser Ser Lys Glu Pro Val Phe Arg Leu Ser Val Ala
370                 375                 380

Thr Asn Val Ser Ala Thr Leu Thr Phe Asn Thr Ser Lys Ile Thr Gly
385                 390                 395                 400

Phe Leu Lys Pro Gly Lys Val Lys Val Glu Leu Lys Glu Ser Lys Val
                405                 410                 415

Gly Leu Phe Asn Ala Glu Leu Leu Glu Ala Leu Leu Asn Tyr Tyr Ile
                420                 425                 430

Leu Asn Thr Phe Tyr Pro Lys Phe Asn Asp Lys Leu Ala Glu Gly Phe
                435                 440                 445

Pro Leu Pro Leu Leu Lys Arg Val Gln Leu Tyr Asp Leu Gly Leu Gln
                450                 455                 460

Ile His Lys Asp Phe Leu Phe Leu Gly Ala Asn Val Gln Tyr Met Arg
465                 470                 475                 480

Val

<210> SEQ ID NO 12
<211> LENGTH: 456
<212> TYPE: PRT
<213> ORGANISM: human
<220> FEATURE:
<223> OTHER INFORMATION: human LBP amino acid (Figure 5); mature protein
      sequence

<400> SEQUENCE: 12

Ala Asn Pro Gly Leu Val Ala Arg Ile Thr Asp Lys Gly Leu Gln Tyr
1               5                   10                  15

Ala Ala Gln Glu Gly Leu Leu Ala Leu Gln Ser Glu Leu Leu Arg Ile
                20                  25                  30

Thr Leu Pro Asp Phe Thr Gly Asp Leu Arg Ile Pro His Val Gly Arg
            35                  40                  45

Gly Arg Tyr Glu Phe His Ser Leu Asn Ile His Ser Cys Glu Leu Leu
    50                  55                  60

His Ser Ala Leu Arg Pro Val Pro Gly Gln Gly Leu Ser Leu Ser Ile
65                  70                  75                  80

Ser Asp Ser Ser Ile Arg Val Gln Gly Arg Trp Lys Val Arg Lys Ser
                85                  90                  95
```

```
Phe Phe Lys Leu Gln Gly Ser Phe Asp Val Ser Val Lys Gly Ile Ser
            100                 105                 110

Ile Ser Val Asn Leu Leu Gly Ser Glu Ser Ser Gly Arg Pro Thr
        115                 120                 125

Val Thr Ala Ser Ser Cys Ser Ser Asp Ile Ala Asp Val Glu Val Asp
    130                 135                 140

Met Ser Gly Asp Leu Gly Trp Leu Leu Asn Leu Phe His Asn Gln Ile
145                 150                 155                 160

Glu Ser Lys Phe Gln Lys Val Leu Glu Ser Arg Ile Cys Glu Met Ile
                165                 170                 175

Gln Lys Ser Val Ser Ser Asp Leu Gln Pro Tyr Leu Gln Thr Leu Pro
            180                 185                 190

Val Thr Thr Glu Ile Asp Ser Phe Ala Asp Ile Asp Tyr Ser Leu Val
        195                 200                 205

Glu Ala Pro Arg Ala Thr Ala Gln Met Leu Glu Val Met Phe Lys Gly
    210                 215                 220

Glu Ile Phe His Arg Asn His Arg Ser Pro Val Thr Leu Leu Ala Ala
225                 230                 235                 240

Val Met Ser Leu Pro Glu His Asn Lys Met Val Tyr Phe Ala Ile
                245                 250                 255

Ser Asp Tyr Val Phe Asn Thr Ala Ser Leu Val Tyr His Glu Glu Gly
            260                 265                 270

Tyr Leu Asn Phe Ser Ile Thr Asp Asp Met Ile Pro Pro Asp Ser Asn
        275                 280                 285

Ile Arg Leu Thr Thr Lys Ser Phe Arg Pro Phe Val Pro Arg Leu Ala
    290                 295                 300

Arg Leu Tyr Pro Asn Met Asn Leu Glu Leu Gln Gly Ser Val Pro Ser
305                 310                 315                 320

Ala Pro Leu Leu Asn Phe Ser Pro Gly Asn Leu Ser Val Asp Pro Tyr
                325                 330                 335

Met Glu Ile Asp Ala Phe Val Leu Leu Pro Ser Ser Ser Lys Glu Pro
            340                 345                 350

Val Phe Arg Leu Ser Val Ala Thr Asn Val Ser Ala Thr Leu Thr Phe
        355                 360                 365

Asn Thr Ser Lys Ile Thr Gly Phe Leu Lys Pro Gly Lys Val Lys Val
    370                 375                 380

Glu Leu Lys Glu Ser Lys Val Gly Leu Phe Asn Ala Glu Leu Leu Glu
385                 390                 395                 400

Ala Leu Leu Asn Tyr Tyr Ile Leu Asn Thr Phe Tyr Pro Lys Phe Asn
                405                 410                 415

Asp Lys Leu Ala Glu Gly Phe Pro Leu Pro Leu Leu Lys Arg Val Gln
            420                 425                 430

Leu Tyr Asp Leu Gly Leu Gln Ile His Lys Asp Phe Leu Phe Leu Gly
        435                 440                 445

Ala Asn Val Gln Tyr Met Arg Val
    450                 455

<210> SEQ ID NO 13
<211> LENGTH: 483
<212> TYPE: PRT
<213> ORGANISM: bovine
<220> FEATURE:
<223> OTHER INFORMATION: bovine BPI amino acid (Figure 5)
<221> NAME/KEY: SIGNAL
<222> LOCATION: (1)..(26)
<221> NAME/KEY: CHAIN
```

<222> LOCATION: (27)..(483)

<400> SEQUENCE: 13

```
Met Ala Arg Gly Pro Asp Thr Ala Arg Trp Ala Thr Leu Val Val
 1               5                  10                  15

Leu Ala Ala Leu Gly Thr Ala Val Thr Thr Asn Pro Gly Ile Val
             20                  25                  30

Ala Arg Ile Ile Gln Lys Gly Leu Asp Tyr Ala Cys Gln Gln Gly Val
         35                  40                  45

Leu Thr Leu Gln Lys Glu Leu Glu Lys Ile Thr Ile Pro Asn Phe Ser
     50                  55                  60

Gly Asn Phe Lys Ile Lys Tyr Leu Gly Lys Gly Gln Tyr Ser Phe Phe
 65                  70                  75                  80

Ser Met Val Ile Gln Gly Phe Asn Leu Pro Asn Ser Gln Ile Arg Pro
                 85                  90                  95

Leu Pro Asp Lys Gly Leu Asp Leu Ser Ile Arg Asp Ala Ser Ile Lys
            100                 105                 110

Ile Arg Gly Lys Trp Lys Ala Arg Lys Asn Phe Ile Lys Leu Gly Gly
        115                 120                 125

Asn Phe Asp Leu Ser Val Glu Gly Ile Ser Ile Leu Ala Gly Leu Asn
130                 135                 140

Leu Gly Tyr Asp Pro Ala Ser Gly His Ser Thr Val Thr Cys Ser Ser
145                 150                 155                 160

Cys Ser Ser Gly Ile Asn Thr Val Arg Ile Met Ile Ser Gly Ser Ser
                165                 170                 175

Leu Gly Trp Leu Ile Gln Leu Phe Arg Lys Arg Ile Glu Ser Leu Leu
            180                 185                 190

Gln Lys Ser Met Thr Arg Lys Ile Cys Glu Val Val Thr Ser Thr Val
        195                 200                 205

Ser Ser Lys Leu Gln Pro Tyr Phe Gln Thr Leu Pro Val Thr Thr Lys
    210                 215                 220

Leu Asp Lys Val Ala Gly Val Asp Tyr Ser Leu Val Ala Pro Pro Arg
225                 230                 235                 240

Ala Thr Ala Asn Asn Leu Asp Trp Leu Leu Lys Gly Glu Phe Phe Ser
                245                 250                 255

Leu Ala His Arg Ser Pro Pro Phe Ala Pro Ala Leu Ala Phe
            260                 265                 270

Ala Ser Asp His Asp Arg Met Val Tyr Leu Gly Ile Ser Asp Tyr Phe
        275                 280                 285

Phe Asn Thr Ala Gly Phe Val Tyr Gln Lys Ala Gly Ala Leu Asn Leu
290                 295                 300

Thr Leu Arg Asp Asp Met Ile Pro Lys Glu Ser Lys Phe Arg Leu Thr
305                 310                 315                 320

Thr Lys Phe Phe Gly Ile Leu Ile Pro Gln Val Ala Lys Met Phe Pro
                325                 330                 335

Pro Met Gln Met Gln Leu Phe Ile Trp Ala Ser Leu Pro Pro Lys Leu
            340                 345                 350

Thr Met Lys Pro Ser Ser Leu Asp Leu Ile Phe Val Leu Asp Thr Gln
        355                 360                 365

Ala Phe Ala Ile Leu Pro Asn Ser Ser Leu Asp Pro Leu Phe Leu Leu
370                 375                 380

Glu Met Asn Leu Asn Leu Ser Val Val Gly Ala Lys Ser Asp Arg
385                 390                 395                 400
```

-continued

```
Leu Ile Gly Glu Leu Arg Leu Asp Lys Leu Leu Glu Leu Lys His
                405                 410                 415

Ser Asp Ile Gly Pro Phe Ser Val Glu Ser Leu Gln Ser Val Ile Asn
                420                 425                 430

Tyr Val Met Pro Thr Ile Val Leu Pro Val Ile Asn Lys Lys Leu Gln
                435                 440                 445

Lys Gly Phe Pro Leu Pro Leu Pro Ala Tyr Ile Glu Leu Phe Asn Leu
450                 455                 460

Thr Leu Gln Pro Tyr Gln Asp Phe Leu Leu Phe Gly Ala Asp Val Gln
465                 470                 475                 480

Tyr Ser Asp

<210> SEQ ID NO 14
<211> LENGTH: 457
<212> TYPE: PRT
<213> ORGANISM: bovine
<220> FEATURE:
<223> OTHER INFORMATION: bovine BPI amino acid (Figure 5); mature
      protein sequence

<400> SEQUENCE: 14

Thr Asn Pro Gly Ile Val Ala Arg Ile Ile Gln Lys Gly Leu Asp Tyr
  1               5                  10                  15

Ala Cys Gln Gln Gly Val Leu Thr Leu Gln Lys Glu Leu Glu Lys Ile
                 20                  25                  30

Thr Ile Pro Asn Phe Ser Gly Asn Phe Lys Ile Lys Tyr Leu Gly Lys
             35                  40                  45

Gly Gln Tyr Ser Phe Phe Ser Met Val Ile Gln Gly Phe Asn Leu Pro
     50                  55                  60

Asn Ser Gln Ile Arg Pro Leu Pro Asp Lys Gly Leu Asp Leu Ser Ile
 65                  70                  75                  80

Arg Asp Ala Ser Ile Lys Ile Arg Gly Lys Trp Lys Ala Arg Lys Asn
                 85                  90                  95

Phe Ile Lys Leu Gly Gly Asn Phe Asp Leu Ser Val Glu Gly Ile Ser
                100                 105                 110

Ile Leu Ala Gly Leu Asn Leu Gly Tyr Asp Pro Ala Ser Gly His Ser
            115                 120                 125

Thr Val Thr Cys Ser Ser Cys Ser Ser Gly Ile Asn Thr Val Arg Ile
        130                 135                 140

Met Ile Ser Gly Ser Ser Leu Gly Trp Leu Ile Gln Leu Phe Arg Lys
145                 150                 155                 160

Arg Ile Glu Ser Leu Leu Gln Lys Ser Met Thr Arg Lys Ile Cys Glu
                165                 170                 175

Val Val Thr Ser Thr Val Ser Ser Lys Leu Gln Pro Tyr Phe Gln Thr
                180                 185                 190

Leu Pro Val Thr Thr Lys Leu Asp Lys Val Ala Gly Val Asp Tyr Ser
            195                 200                 205

Leu Val Ala Pro Pro Arg Ala Thr Ala Asn Asn Leu Asp Trp Leu Leu
        210                 215                 220

Lys Gly Glu Phe Phe Ser Leu Ala His Arg Ser Pro Pro Phe Ala
225                 230                 235                 240

Pro Pro Ala Leu Ala Phe Ala Ser Asp His Asp Arg Met Val Tyr Leu
                245                 250                 255

Gly Ile Ser Asp Tyr Phe Asn Thr Ala Gly Phe Val Tyr Gln Lys
                260                 265                 270
```

```
Ala Gly Ala Leu Asn Leu Thr Leu Arg Asp Asp Met Ile Pro Lys Glu
        275                 280                 285

Ser Lys Phe Arg Leu Thr Thr Lys Phe Phe Gly Ile Leu Ile Pro Gln
        290                 295                 300

Val Ala Lys Met Phe Pro Met Gln Met Gln Leu Phe Ile Trp Ala
305             310                 315                 320

Ser Leu Pro Pro Lys Leu Thr Met Lys Pro Ser Ser Leu Asp Leu Ile
                325                 330                 335

Phe Val Leu Asp Thr Gln Ala Phe Ala Ile Leu Pro Asn Ser Ser Leu
            340                 345                 350

Asp Pro Leu Phe Leu Leu Glu Met Asn Leu Asn Leu Ser Val Val Val
        355                 360                 365

Gly Ala Lys Ser Asp Arg Leu Ile Gly Glu Leu Arg Leu Asp Lys Leu
        370                 375                 380

Leu Leu Glu Leu Lys His Ser Asp Ile Gly Pro Phe Ser Val Glu Ser
385                 390                 395                 400

Leu Gln Ser Val Ile Asn Tyr Val Met Pro Thr Ile Val Leu Pro Val
                405                 410                 415

Ile Asn Lys Lys Leu Gln Lys Gly Phe Pro Leu Pro Leu Pro Ala Tyr
                420                 425                 430

Ile Glu Leu Phe Asn Leu Thr Leu Gln Pro Tyr Gln Asp Phe Leu Leu
        435                 440                 445

Phe Gly Ala Asp Val Gln Tyr Ser Asp
        450                 455

<210> SEQ ID NO 15
<211> LENGTH: 487
<212> TYPE: PRT
<213> ORGANISM: human
<220> FEATURE:
<223> OTHER INFORMATION: human BPI amino acid (Figure 5)
<221> NAME/KEY: SIGNAL
<222> LOCATION: (1)..(31)
<221> NAME/KEY: CHAIN
<222> LOCATION: (32)..(487)

<400> SEQUENCE: 15

Met Arg Glu Asn Met Ala Arg Gly Pro Cys Asn Ala Pro Arg Trp Val
  1               5                  10                  15

Ser Leu Met Val Leu Val Ala Ile Gly Thr Ala Val Thr Ala Ala Val
                20                  25                  30

Asn Pro Gly Val Val Val Arg Ile Ser Gln Lys Gly Leu Asp Tyr Ala
            35                  40                  45

Ser Gln Gln Gly Thr Ala Ala Leu Gln Lys Glu Leu Lys Arg Ile Lys
        50                  55                  60

Ile Pro Asp Tyr Ser Asp Ser Phe Lys Ile Lys His Leu Gly Lys Gly
 65                  70                  75                  80

His Tyr Ser Phe Tyr Ser Met Asp Ile Arg Glu Phe Gln Leu Pro Ser
                 85                  90                  95

Ser Gln Ile Ser Met Val Pro Asn Val Gly Leu Lys Phe Ser Ile Ser
                100                 105                 110

Asn Ala Asn Ile Lys Ile Ser Gly Lys Trp Lys Ala Gln Lys Arg Phe
            115                 120                 125

Leu Lys Met Ser Gly Asn Phe Asp Leu Ser Ile Glu Gly Met Ser Ile
        130                 135                 140

Ser Ala Asp Leu Lys Leu Gly Ser Asn Pro Thr Ser Gly Lys Pro Thr
145                 150                 155                 160
```

```
Ile Thr Cys Ser Ser Cys Ser Ser His Ile Asn Ser Val His Val His
                165                 170                 175

Ile Ser Lys Ser Lys Val Gly Trp Leu Ile Gln Leu Phe His Lys Lys
            180                 185                 190

Ile Glu Ser Ala Leu Arg Asn Lys Met Asn Ser Gln Val Cys Glu Lys
        195                 200                 205

Val Thr Asn Ser Val Ser Ser Lys Leu Gln Pro Tyr Phe Gln Thr Leu
    210                 215                 220

Pro Val Met Thr Lys Ile Asp Ser Val Ala Gly Ile Asn Tyr Gly Leu
225                 230                 235                 240

Val Ala Pro Pro Ala Thr Thr Ala Glu Thr Leu Asp Val Gln Met Lys
                245                 250                 255

Gly Glu Phe Tyr Ser Glu Asn His His Asn Pro Pro Phe Ala Pro
            260                 265                 270

Pro Val Met Glu Phe Pro Ala Ala His Asp Arg Met Val Tyr Leu Gly
                275                 280                 285

Leu Ser Asp Tyr Phe Phe Asn Thr Ala Gly Leu Val Tyr Gln Glu Ala
        290                 295                 300

Gly Val Leu Lys Met Thr Leu Arg Asp Asp Met Ile Pro Lys Glu Ser
305                 310                 315                 320

Lys Phe Arg Leu Thr Thr Lys Phe Phe Gly Thr Phe Leu Pro Glu Val
                325                 330                 335

Ala Lys Lys Phe Pro Asn Met Lys Ile Gln Ile His Val Ser Ala Ser
            340                 345                 350

Thr Pro Pro His Leu Ser Val Gln Pro Thr Gly Leu Thr Phe Tyr Pro
        355                 360                 365

Ala Val Asp Val Gln Ala Phe Ala Val Leu Pro Asn Ser Ser Leu Ala
    370                 375                 380

Ser Leu Phe Leu Ile Gly Met His Thr Thr Gly Ser Met Glu Val Ser
385                 390                 395                 400

Ala Glu Ser Asn Arg Leu Val Gly Glu Leu Lys Leu Asp Arg Leu Leu
                405                 410                 415

Leu Glu Leu Lys His Ser Asn Ile Gly Pro Phe Pro Val Glu Leu Leu
            420                 425                 430

Gln Asp Ile Met Asn Tyr Ile Val Pro Ile Leu Val Leu Pro Arg Val
        435                 440                 445

Asn Glu Lys Leu Gln Lys Gly Phe Pro Leu Pro Thr Pro Ala Arg Val
    450                 455                 460

Gln Leu Tyr Asn Val Val Leu Gln Pro His Gln Asn Phe Leu Leu Phe
465                 470                 475                 480

Gly Ala Asp Val Val Tyr Lys
                485

<210> SEQ ID NO 16
<211> LENGTH: 456
<212> TYPE: PRT
<213> ORGANISM: human
<220> FEATURE:
<223> OTHER INFORMATION: human BPI amino acid (Figure 5); mature protein
      sequence

<400> SEQUENCE: 16

Val Asn Pro Gly Val Val Arg Ile Ser Gln Lys Gly Leu Asp Tyr
  1               5                  10                  15

Ala Ser Gln Gln Gly Thr Ala Ala Leu Gln Lys Glu Leu Lys Arg Ile
```

-continued

```
              20                  25                  30
Lys Ile Pro Asp Tyr Ser Asp Ser Phe Lys Ile Lys His Leu Gly Lys
             35                  40                  45

Gly His Tyr Ser Phe Tyr Ser Met Asp Ile Arg Glu Phe Gln Leu Pro
     50                  55                  60

Ser Ser Gln Ile Ser Met Val Pro Asn Val Gly Leu Lys Phe Ser Ile
 65                  70                  75                  80

Ser Asn Ala Asn Ile Lys Ile Ser Gly Lys Trp Lys Ala Gln Lys Arg
                 85                  90                  95

Phe Leu Lys Met Ser Gly Asn Phe Asp Leu Ser Ile Glu Gly Met Ser
                100                 105                 110

Ile Ser Ala Asp Leu Lys Leu Gly Ser Asn Pro Thr Ser Gly Lys Pro
            115                 120                 125

Thr Ile Thr Cys Ser Ser Cys Ser Ser His Ile Asn Ser Val His Val
        130                 135                 140

His Ile Ser Lys Ser Lys Val Gly Trp Leu Ile Gln Leu Phe His Lys
145                 150                 155                 160

Lys Ile Glu Ser Ala Leu Arg Asn Lys Met Asn Ser Gln Val Cys Glu
                165                 170                 175

Lys Val Thr Asn Ser Val Ser Ser Lys Leu Gln Pro Tyr Phe Gln Thr
            180                 185                 190

Leu Pro Val Met Thr Lys Ile Asp Ser Val Ala Gly Ile Asn Tyr Gly
        195                 200                 205

Leu Val Ala Pro Pro Ala Thr Thr Ala Glu Thr Leu Asp Val Gln Met
    210                 215                 220

Lys Gly Glu Phe Tyr Ser Glu Asn His His Asn Pro Pro Phe Ala
225                 230                 235                 240

Pro Pro Val Met Glu Phe Pro Ala Ala His Asp Arg Met Val Tyr Leu
                245                 250                 255

Gly Leu Ser Asp Tyr Phe Phe Asn Thr Ala Gly Leu Val Tyr Gln Glu
            260                 265                 270

Ala Gly Val Leu Lys Met Thr Leu Arg Asp Asp Met Ile Pro Lys Glu
        275                 280                 285

Ser Lys Phe Arg Leu Thr Thr Lys Phe Phe Gly Thr Phe Leu Pro Glu
    290                 295                 300

Val Ala Lys Lys Phe Pro Asn Met Lys Ile Gln Ile His Val Ser Ala
305                 310                 315                 320

Ser Thr Pro Pro His Leu Ser Val Gln Pro Thr Gly Leu Thr Phe Tyr
                325                 330                 335

Pro Ala Val Asp Val Gln Ala Phe Ala Val Leu Pro Asn Ser Ser Leu
            340                 345                 350

Ala Ser Leu Phe Leu Ile Gly Met His Thr Thr Gly Ser Met Glu Val
        355                 360                 365

Ser Ala Glu Ser Asn Arg Leu Val Gly Glu Leu Lys Leu Asp Arg Leu
    370                 375                 380

Leu Leu Glu Leu Lys His Ser Asn Ile Gly Pro Phe Pro Val Glu Leu
385                 390                 395                 400

Leu Gln Asp Ile Met Asn Tyr Ile Val Pro Ile Leu Val Leu Pro Arg
                405                 410                 415

Val Asn Glu Lys Leu Gln Lys Gly Phe Pro Leu Pro Thr Pro Ala Arg
            420                 425                 430

Val Gln Leu Tyr Asn Val Val Leu Gln Pro His Gln Asn Phe Leu Leu
        435                 440                 445
```

```
Phe Gly Ala Asp Val Val Tyr Lys
    450                 455

<210> SEQ ID NO 17
<211> LENGTH: 479
<212> TYPE: PRT
<213> ORGANISM: LBP-BPI
<220> FEATURE:
<223> OTHER INFORMATION: LBP 1-197-BPI 200-456 (NYC118)

<400> SEQUENCE: 17

Met Gly Ala Leu Ala Arg Ala Leu Pro Ser Ile Leu Ala Leu Leu
  1               5                  10                  15

Leu Thr Ser Thr Pro Glu Ala Leu Gly Ala Asn Pro Gly Leu Val Ala
                 20                  25                  30

Arg Ile Thr Asp Lys Gly Leu Gln Tyr Ala Ala Gln Glu Gly Leu Leu
             35                  40                  45

Ala Leu Gln Ser Glu Leu Leu Arg Ile Thr Leu Pro Asp Phe Thr Gly
 50                  55                           60

Asp Leu Arg Ile Pro His Val Gly Arg Gly Arg Tyr Glu Phe His Ser
 65                   70                  75                  80

Leu Asn Ile His Ser Cys Glu Leu Leu His Ser Ala Leu Arg Pro Val
                 85                  90                  95

Pro Gly Gln Gly Leu Ser Leu Ser Ile Ser Asp Ser Ser Ile Arg Val
                100                 105                 110

Gln Gly Arg Trp Lys Val Arg Lys Ser Phe Phe Lys Leu Gln Gly Ser
            115                 120                 125

Phe Asp Val Ser Val Lys Gly Ile Ser Ile Ser Val Asn Leu Leu Leu
130                 135                 140

Gly Ser Glu Ser Ser Gly Arg Pro Thr Val Thr Ala Ser Ser Cys Ser
145                 150                 155                 160

Ser Asp Ile Ala Asp Val Glu Val Asp Met Ser Gly Asp Leu Gly Trp
                165                 170                 175

Leu Leu Asn Leu Phe His Asn Gln Ile Glu Ser Lys Phe Gln Lys Val
                180                 185                 190

Leu Glu Ser Arg Ile Cys Glu Met Ile Gln Lys Ser Val Ser Ser Asp
            195                 200                 205

Leu Gln Pro Tyr Leu Gln Thr Leu Pro Val Thr Thr Glu Ile Asp Ser
210                 215                 220

Val Ala Gly Ile Asn Tyr Gly Leu Val Ala Pro Pro Ala Thr Thr Ala
225                 230                 235                 240

Glu Thr Leu Asp Val Gln Met Lys Gly Glu Phe Tyr Ser Glu Asn His
                245                 250                 255

His Asn Pro Pro Pro Phe Ala Pro Pro Val Met Glu Phe Pro Ala Ala
                260                 265                 270

His Asp Arg Met Val Tyr Leu Gly Leu Ser Asp Tyr Phe Phe Asn Thr
            275                 280                 285

Ala Gly Leu Val Tyr Gln Glu Ala Gly Val Leu Lys Met Thr Leu Arg
290                 295                 300

Asp Asp Met Ile Pro Lys Glu Ser Lys Phe Arg Leu Thr Thr Lys Phe
305                 310                 315                 320

Phe Gly Thr Phe Leu Pro Glu Val Ala Lys Lys Phe Pro Asn Met Lys
                325                 330                 335

Ile Gln Ile His Val Ser Ala Ser Thr Pro Pro His Leu Ser Val Gln
                340                 345                 350
```

-continued

```
Pro Thr Gly Leu Thr Phe Tyr Pro Ala Val Asp Val Gln Ala Leu Ala
        355                 360                 365

Val Leu Pro Asn Ser Ser Leu Ala Ser Leu Phe Leu Ile Gly Met His
    370                 375                 380

Thr Thr Gly Ser Met Glu Val Ser Ala Glu Ser Asn Arg Leu Val Gly
385                 390                 395                 400

Glu Leu Lys Leu Asp Arg Leu Leu Leu Glu Leu Lys His Ser Asn Ile
            405                 410                 415

Gly Pro Phe Pro Val Glu Leu Leu Gln Asp Ile Met Asn Tyr Ile Val
            420                 425                 430

Pro Ile Leu Val Leu Pro Arg Val Asn Glu Lys Leu Gln Lys Gly Phe
        435                 440                 445

Pro Leu Pro Thr Pro Ala Arg Val Gln Leu Tyr Asn Val Val Leu Gln
    450                 455                 460

Pro His Gln Asn Phe Leu Leu Phe Gly Ala Asp Val Val Tyr Lys
465                 470                 475
```

RECOMBINANT ENDOTOXIN-NEUTRALIZING PROTEINS

CROSS REFERENCE TO RELATED APPLICATIONS

This application is a continuation-in-part of:

1) U.S. application Ser. No. 07/915,720, filed Jul. 22, 1992, now U.S. Pat. No. 5,770,694, which is the U.S. national phase application of PCT International application no. PCT/US91/05758, filed Aug. 13, 1991, which was filed in the PCT designating the U.S. as a continuation-in-part of U.S. application Ser. No. 07/681,551, filed Apr. 5, 1991, now U.S. Pat. No. 5,171,739, issued Dec. 15, 1992, which is a continuation-in-part of U.S. application Ser. No. 07/567,016, filed Aug. 13, 1990, now abandoned, which is a continuation-in-part of U.S. application Ser. No. 07/468,696, filed Jan. 22, 1990, now U.S. Pat. No. 5,089,274, issued Feb. 18, 1992, which is a continuation-in-part of U.S. application Ser. No. 07/310,842, filed Feb. 14, 1989, now abandoned; and 2) PCT International application no. PCT/US94/04709, filed Apr. 29, 1994, which was filed in the PCT designating the U.S. as a continuation-in-part of U.S. application Ser. No. 08/165,717, filed Dec. 10, 1993, now abandoned which is a continuation-in-part of U.S. patent application Ser. No. 08/056,292, filed Apr. 30, 1993, now abandoned which is a continuation-in-part of U.S. application Ser. No. 07/567,016, filed Aug. 13, 1990, now abandoned, which is a continuation-in-part of U.S. application Ser. No. 07/468,696, filed Jan. 22, 1990, now U.S. Pat. No. 5,089,274, issued Feb. 18, 1992, which is a continuation-in-part of U.S. application Ser. No. 07/310,842, filed Feb. 14, 1989, now abandoned. These applications are each incorporated herein by reference and are applications to which we claim priority under 35 U.S.C. §120 or §365(c).

FIELD OF THE INVENTION

This invention relates generally to the field of recombinant, endotoxin-neutralizing proteins, particularly to recombinant proteins which bind endotoxin and block endotoxin-mediated activation of biological systems.

BACKGROUND OF THE INVENTION

Gram-negative infections are a major cause of morbidity and mortality, especially in hospitalized and immunocompromised patients. [Duma, *Am. J. of Med.*, 78 (Suppl. 6A):154–164 (1985); and Kreger et al., *Am. J. Med.*, 68:344–355 (1980)]. Although available generally effective in inhibiting growth of Gram-negative bacteria, they do not neutralize the pathophysiological effects associated with endotoxins. Endotoxin is a heat stable bacterial toxin composed of lipopolysaccharides (LPS) released from the outer membrane of Gram-negative bacteria upon lysis [Shenep et al., *J. Infect. Dis.*, 150(3):380–388 (1984)], and is a potent stimulator of the inflammatory response. Endotoxemia occurs when endotoxin enters the bloodstream resulting in a dramatic systemic inflammatory response.

Many detrimental in vivo effects of LPS result from soluble mediators released by inflammatory cells. [Morrison et al., *Am. J. Pathol.*, 93(2):527–617 (1978)]. Monocytes and neutrophils, which ingest and kill microorganisms, play a key role in this process. Monocytes and neutrophils respond to endotoxin in vivo by releasing soluble proteins with microbicidal, proteolytic, opsonic, pyrogenic, complement-activating and tissue-damaging effects. These factors mediate many of the pathophysiological effects of endotoxin. For example, tumor necrosis factor (TNF), a cytokine released by endotoxin-stimulated monocytes, causes fever, shock, and alterations in glucose metabolism and is a potent stimulator of neutrophils. Other cytokines such as IL-1, IL-6, and IL-8 also mediate many of the pathophysiologic effects of LPS, as well as other pathways involving endothelial cell activation by tissue factor, kininogen, nitric oxide and complement.

Endotoxin-associated disorders result from extra-gastrointestinal exposure to LPS, e.g. administration of LPS-contaminated fluids, or Gram-negative infections. Endotoxin-associated disorders can also result when the natural epithelial barrier is injured and the normal Gram-negative flora breach this barrier. For example, endotoxin-associated disorders can occur (a) when there is ischemia of the gastrointestinal tract (e.g., following hemorrhagic shock or during certain surgical procedures), or (b) when systemic or local inflammation causes increased permeability of the gut to endotoxin or Gram-negative organisms. The presence of endotoxin and the resulting inflammatory response may result, for example, in endotoxemia, systemic inflammatory response syndrome (SIRS), sepsis syndrome, septic shock, disseminated intravascular coagulation (DIC), adult respiratory distress syndrome (ARDS), cardiac dysfunction, organ failure, liver failure (hepatobiliary dysfunction), brain failure (CNS dysfunction), renal failure, multi-organ failure and shock.

Examples of diseases which can be associated with Gram-negative bacterial infections or endotoxemia include bacterial meningitis, neonatal sepsis, cystic fibrosis, inflammatory bowel disease and liver cirrhosis, Gram-negative pneumonia, Gram-negative abdominal abscess, hemorrhagic shock and disseminated intravascular coagulation. Subjects who are leukopenic or neutropenic, including subjects treated with chemotherapy or immunocompromised subjects (for example with AIDS), are particularly susceptible to bacterial infection and the subsequent effects of endotoxin.

Several therapeutic compounds have been developed to inhibit the toxic effects of endotoxin, including antibacterial LPS-binding agents and anti-LPS antibodies, although each has met with limitations. For example, Polymyxin B (PMB) is a basic polypeptide antibiotic which binds to Lipid A, the most toxic and biologically active component of endotoxin. PMB inhibits endotoxin-mediated activation of neutrophil granule release in vitro and is a potential therapeutic agent for Gram-negative infections. However, because of its systemic toxicity, this antibiotic has limited therapeutic use, and is generally used topically. Combination therapy using antibiotics and high doses of methylprednisolone sodium succinate (MPSS) showed more promise as this regimen prevented death in an experimental animal model of Gram-negative sepsis. However, a clinical study using MPSS with antibiotics in treatment of patients having clinical signs of systemic sepsis showed that mortality rates were not significantly different between the treatment and placebo groups [Bone et al., *N. Engl. J. Med.* 317:653 (1987)].

Antibodies that bind endotoxin have been used in the treatment of endotoxemia. For example, hyperimmune human antisera against *E. coli* J5 reduced mortality by 50% in patients with Gram-negative bacteremia and shock [Ziegler et al., *N. Engl. J. Med.* 307:1225 (1982)]. However, attempts to treat Gram-negative sepsis by administration of anti-LPS monoclonal antibodies met with little or no success [Ziegler et al., *N. Engl. J. Med.* 324:429 (1991); Greenman et al., *JAMA* 266:1097 (1991); Baumgartner et al., *N. Engl. J. Med.* 325:279 (1991)].

Another approach to treating endotoxemia involves the use of cytokine blockers, such as IL-1 receptor antagonists and anti-TNF antibodies, as well as the soluble forms of the IL-1 and TNF receptors. However, any given cytokine blocker blocks only the cytokine for which it is specific, and fails to prevent the action of other cytokines. Furthermore, blocking cytokines may have other deleterious effects.

Two soluble endotoxin-binding proteins, lipopolysaccharide binding protein (LBP) and bactericidal/permeability-increasing (BPI), play opposing roles in vivo in the physiological response to endotoxin. LBP is a soluble LPS receptor found in serum which binds LPS with high affinity via interaction with the Lipid A moiety [Tobias et al. (1986) J. Exp. Med. 164:777–793; Tobias et al. (1989) J. Biol. Chem. 264:10867–10871]. LBP-LPS complexes stimulate monocyte activation through interaction with the CD14 receptor on the surface of monocytes, resulting in production of cytokines such as TNF and IL-1 [Wright et al. (1989) J. Exp. Med. 170:1231–1241; Wright et al. (1990) Science 249:1431]. Thus, LBP acts as a transfer protein in LPS-mediated stimulation of cytokine release. Moreover, LBP increases LPS activity in that a lower concentration of LPS is required to stimulate monocytes in the presence of LBP than in its absence.

In direct contrast to LBP, BPI binds and neutralizes endotoxin, preventing inflammatory cell activation. BPI, also known as CAP57 and BP [Shafer et al., Infect. Immun. 45:29 (1984); Hovde et al., Infect. Immun. 54:142 (1986)] is also bactericidal by virtue of its interaction with the Lipid A moiety of LPS in the bacterial cell wall. BPI binds LPS, disrupts LPS structure and the cell wall, and increases bacterial membrane permeability, resulting in cell death [Weiss et al., J. Biol. Chem, 253:2664–2672 (1978); Weiss et al., Infection and Immunity 38:1149–1153 (1982)]. BPI retains its in vitro bactericidal activity after protease cleavage, suggesting that BPI fragments retain activity [Ooi et al., Clinical Research 33(2):567A (1985)]. This observation was confirmed by Ooi et al., who showed that an N-terminal 25 kD fragment of BPI exhibited both the in vitro bactericidal and permeability increasing activities [Ooi et al., J. Biol. Chem. 262:14891 (1987)].

Molecular Structures of BPI and LBP

The genes encoding BPI and LBP have been cloned [Gray et al. (1989) J. Biol. Chem. 264:9505–9509; Schumann et al., Science 249:1429–1431 (1990)]. BPI and LBP are immunologically cross-reactive, contain a hydrophobic leader sequence, and share significant amino acid sequence homology over the entire length of the molecules, with an overall amino acid sequence identity of 44% [Tobias et al., J. Biol. Chem. 263:13479–13481 (1988); Schumann et al. supra]. BPI and LBP each contains three cysteine residues. BPI contains two glycosylation sites; LBP contains five potential glycosylation sites.

BPI is characterized by two distinct domains, an N-terminal domain and a C-terminal domain, which are separated by a proline-rich hinge region. The N-terminal domain of BPI has strong LPS-neutralizing activity, while the C-terminal domain of BPI has modest LPS-neutralizing activity. LBP can also be divided into N- and C-terminal domains, with the C-terminal domain being implicated in binding of LPS to macrophages and their subsequent activation.

The N- and C-terminal domains of BPI have a striking charge asymmetry that is not shared by LBP. The N-terminal domain of BPI, which is rich in positively charged lysine residues, imparts a predicted pI>10 to the full-length molecule. In contrast, the C-terminal domain of BPI is only slightly negatively charged. LBP, which is a neutral protein, has no bactericidal activity [Tobias et al., J. Biol. Chem. 263:13479 (1988)]. This suggests that the bactericidal activity of BPI results from its overall cationicity.

Table 1 provides a comparison of BPI and LBP structure and function.

TABLE 1

Comparison of BPI and LBP Structure and Function

| | BPI | LBP |
| --- | --- | --- |
| Synthesis | | |
| Site of synthesis | Neutrophil | Liver |
| Blood concentration | 1–10 ng/ml | 1–10 µg/ml |
| STRUCTURE | | |
| Molecular mass | 55 kD | 60 kD |
| Glycosylation sites | 2 | 5 |
| Cysteine | 3 | 3 |
| EFFECTS ON LPS MEDIATED: | | |
| neutrophil activation | Inhibits | Stimulates |
| monocyte activation | Inhibits | Stimulates |
| TNF release | Inhibits | Stimulates |
| IL-1 release | Inhibits | Stimulates |
| IL-6 release | Inhibits | Stimulates |

*Four cysteines were reported by Schumann et al. [Science 249: 1429–1431 (1990)]. Subsequent DNA sequence analysis by the present inventors determined that Schumann's sequence was erroneous and that LBP contains only three cysteine residues (see FIG. 1).

Therapeutic intervention to block the inflammatory effects of LPS would ameliorate the morbidity and mortality associated with endotoxemia and septic shock. Unfortunately, although BPI binds LPS with high affinity, it has an extremely short half-life in vivo, thus limiting its use in therapy. Native LBP has a longer half-life but, upon binding of LPS, elicits a brisk monocyte reaction which can facilitate release of deleterious quantities of cytokines.

Early and specific diagnosis of endotoxin-associated disorders is essential in the identification of patients who have or who are at risk of developing such disorders.

Precise identification of a site of Gram-negative infection in a patient would assist the clinician in the design and targeting of antibacterial therapy.

An ideal anti-endotoxin drug candidate and/or LPS detection reagent would have a longer half-life and effective, high-affinity endotoxin binding/inactivation without monocyte stimulation. There is a clear need in the field for specific diagnostic and therapeutic agents which neutralizes the effects of endotoxin and has an acceptably long half-life in vivo. The present invention addresses these problems.

SUMMARY OF THE INVENTION

Recombinant proteins are genetically engineered to bind lipopolysaccharide (LPS) such that the endotoxin is inactivated, thus preventing the endotoxin from inducing the immunological cascade of events associated with endotoxin-related disorders (e.g., activation of monocytes, tumor necrosis factor (TNF) production).

In general, the invention features a recombinant endotoxin-neutralizing polypeptide (RENP) characterized by (i) an amino acid sequence, (ii) a sequence and structure that facilitate specific binding to lipopolysaccharide, (iii) provides endotoxin-neutralizing activity upon LPS binding, and (iv) a half-life that is enhanced relative to the half-life of BPI. Preferably, the RENP is composed of an amino acid sequence similar to, but not identical to, an amino acid sequence of BPI, LBP, or both. Preferably, the RENP contains an LPS-binding domain derived from the amino acid sequence of BPI, LBP, or both. Preferred RENPs are fusion proteins which bind LPS with the high affinity of BPI, but do not contain the BPI amino acid sequences associated with BPI's short half-life.

Preferably, the RENPs are covalently bound to a molecule which further enhances the half-life of the polypeptide. For example, the half-life enhancing molecule can be an immunoglobulin fragment, a half-life determining portion of LBP or LBP derivative, or polyethylene glycol. In related aspects, the invention features DNA encoding an RENP of the invention, vectors and transformed cells containing DNA encoding an RENP, a method for producing RENPs, and detectably labeled RENPs.

A primary object of the invention is to provide an RENP which binds and inactivates endotoxin, and has a half-life suitable for administration to a patient.

Another object of the invention is to provide a pharmaceutical composition containing a therapeutically effective amount of an RENP for use in treatment of endotoxin-related disorders.

Still another object of the invention is to provide endotoxin-neutralizing proteins for use in the detection of LPS. The RENPs can be bound to a label which can be detected or can be bound to a support for use in LPS-detection assays. LPS can be detected in vivo to identify a site of infection in a subject or can be used in an in vitro assay to qualitatively or quantitatively detect LPS in a sample.

Another object of the invention is to provide endotoxin-neutralizing proteins that can be used to produce endotoxin-free solutions and tools for use in, for example, various medical applications.

An advantage of the present invention is that the endotoxin-neutralizing proteins have a half-life in serum which is enhanced relative to the half-life of naturally-occurring LPS-binding proteins, and bind LPS without triggering a significant, undesirable immune response.

Another advantage of the invention is that the RENPs can be administered to a patient immediately upon identification of a symptom of an endotoxin-associated disorder.

Another advantage is that the endotoxin-neutralizing proteins can be administered prophylactically to a patient at risk of endotoxic shock or other LPS-mediated condition.

An advantage of the invention is that various RENPs having binding specificity for LPS for detection of LPS either in vivo or in vitro.

Another advantage of the invention is that the RENPs can be attached to a variety of detectable labels.

Yet another advantage of the invention is that the RENPs can be bound to a molecule which can interact with or which can be a portion of a solid support.

These and other objects, advantages and features of the present invention will become apparent to those persons skilled in the art upon reading the details of the vectors, cell lines and methodology as more fully set forth below.

BRIEF DESCRIPTION OF THE DRAWINGS

FIGS. 1A–1D are a comparison of the amino acid sequences of human LBP as described, by Schumann et al. (LBPa) (SEQ ID NOS:7 and 8) and as used (LBPb) (SEQ ID NO:2).

FIGS. 3A–3D show the nucleotide (SEQ ID NO:3) and amino acid sequences of BPI (SEQ ID NOS:3 and 4).

FIGS. 4A–4C show the nucleotide and amino acid sequences of LIBP (SEQ ID NOS:1 and 2).

Figure 5B:
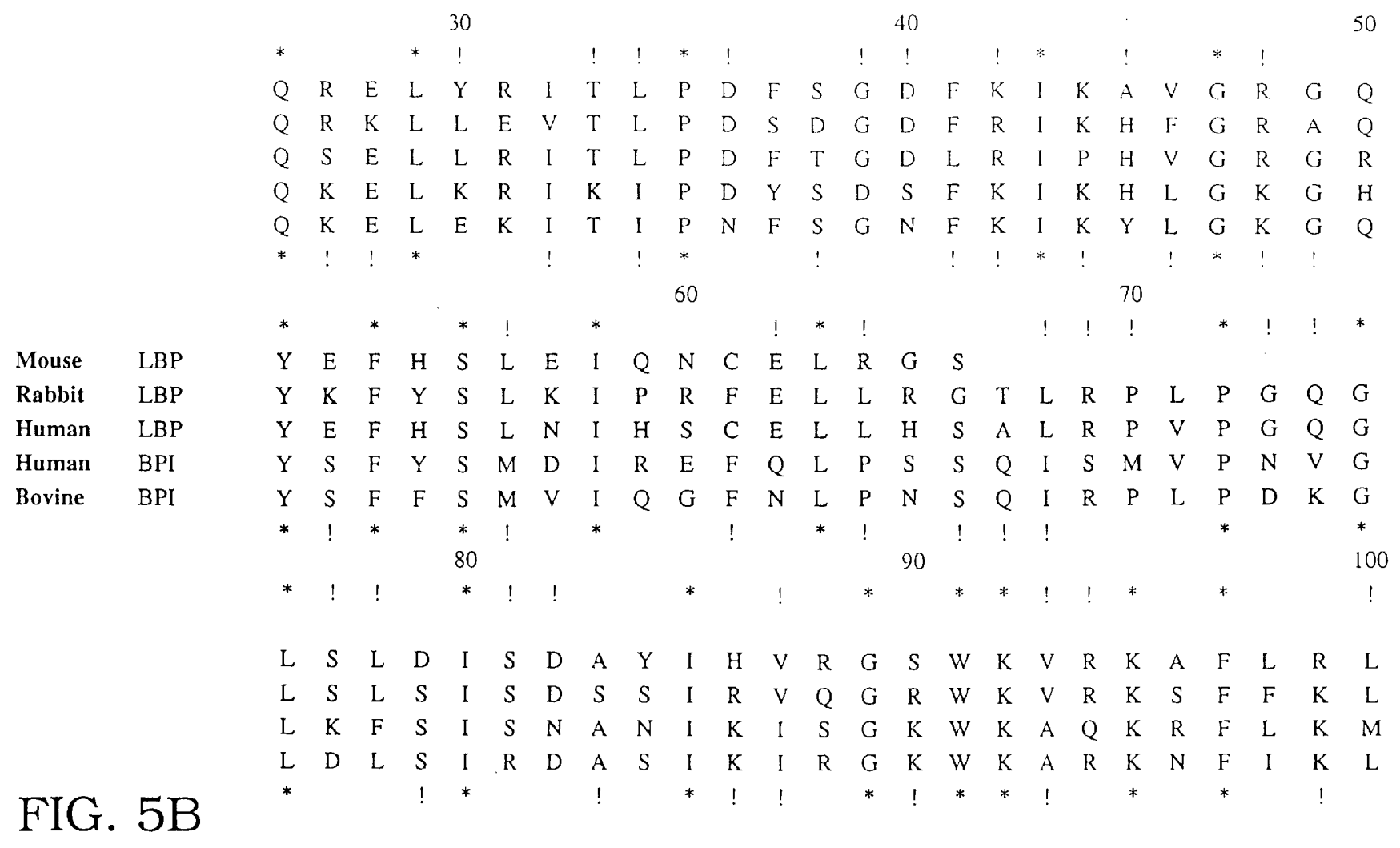
Figure 5D:
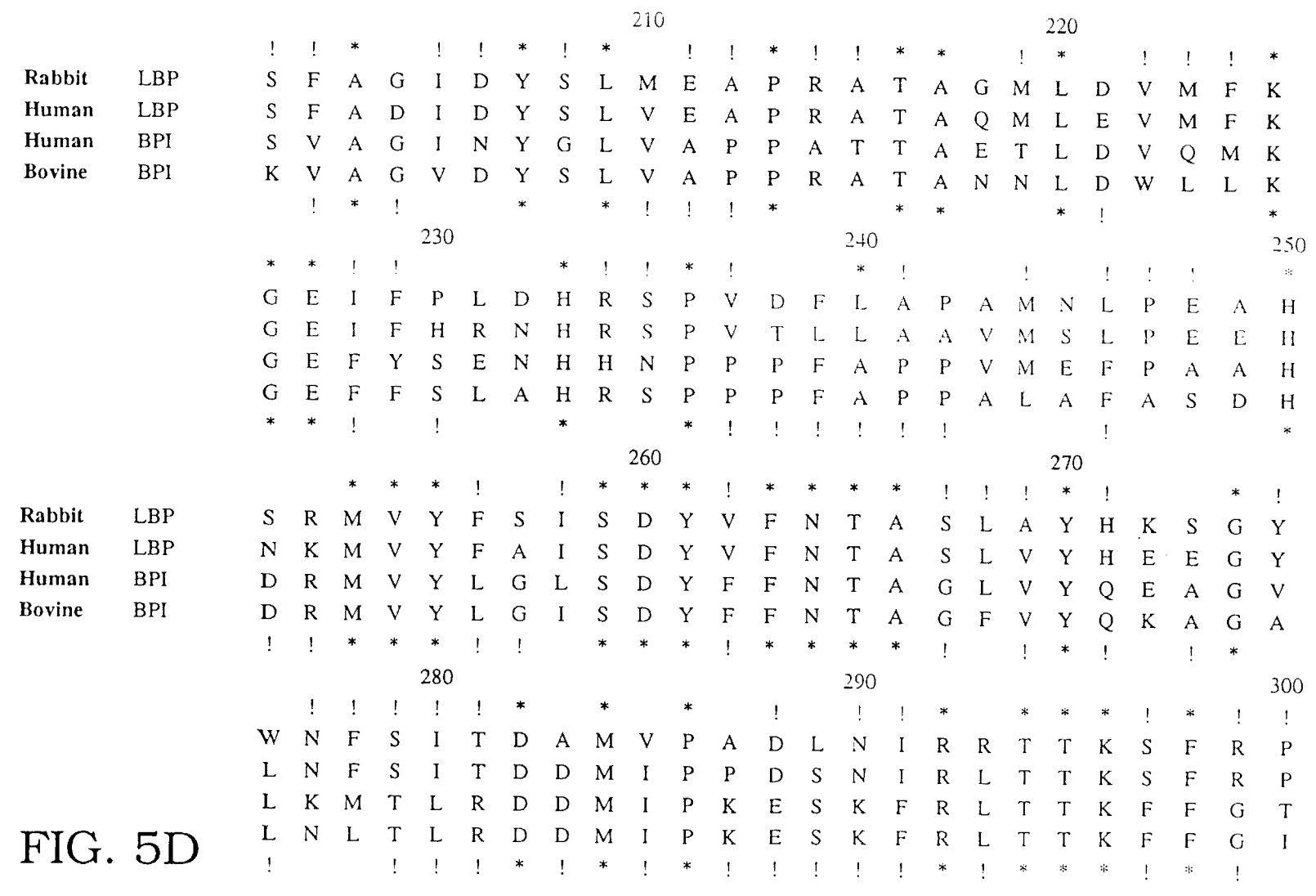
Figure 5E:
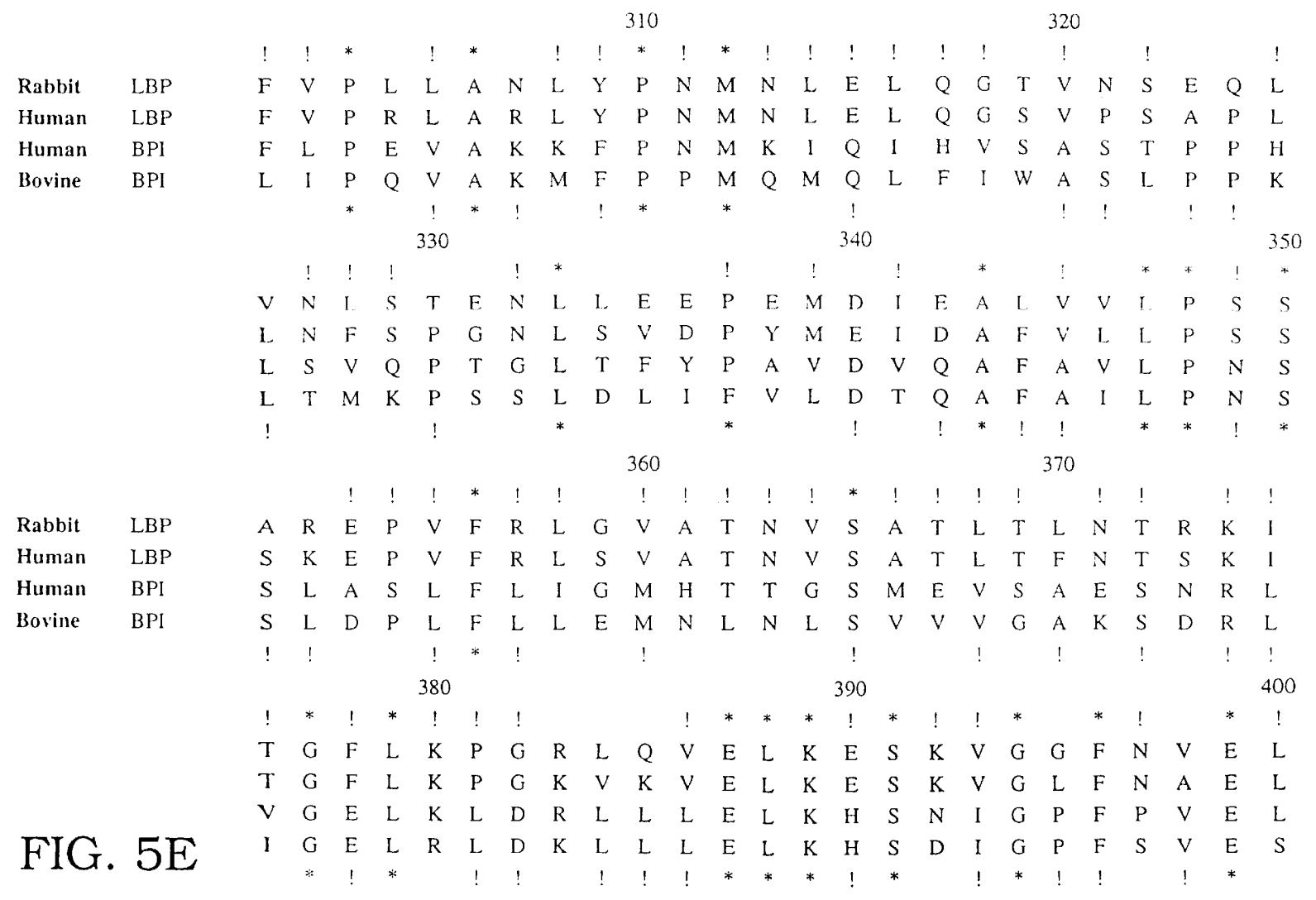
Figure 5F:
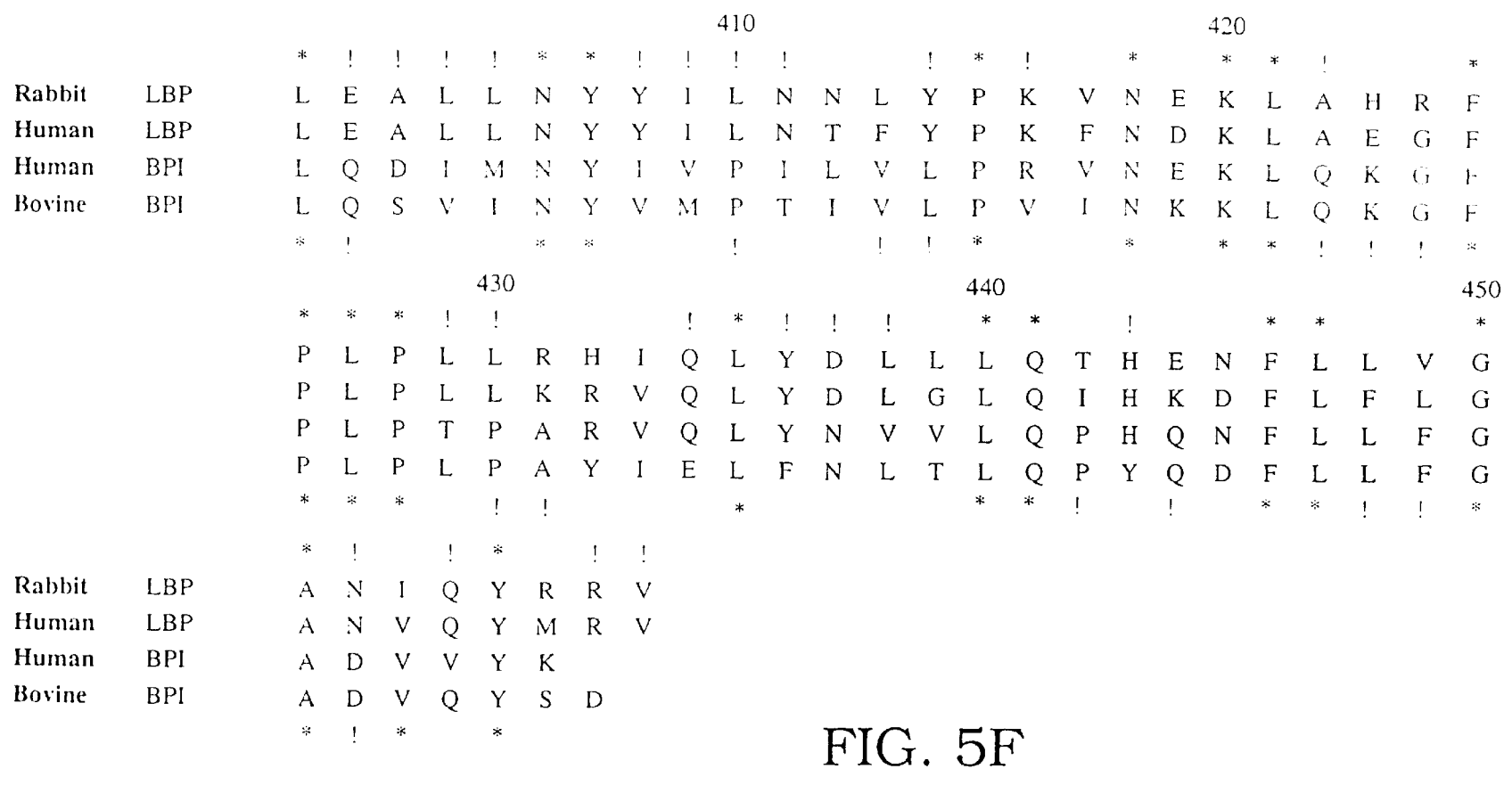

FIGS. 5A–5F are comparison of the amino acid sequences of BPI and LBP from various species (bovine BPI—SEQ ID NOS:13 and 14; human BPI—SEQ ID NOS:15 and 16; rabbit LBP—SEQ ID NOS:5 and 6; mouse LBP—SEQ ID NOS:9 and 10; human LBP—SEQ ID NOS:11 and 12).

FIG. 6 shows the amino acid sequence of $L_{1-197}B_{200-456}$ (NCY118 SEQ ID NO:17).

DESCRIPTION OF THE PREFERRED EMBODIMENTS

Figure 2:
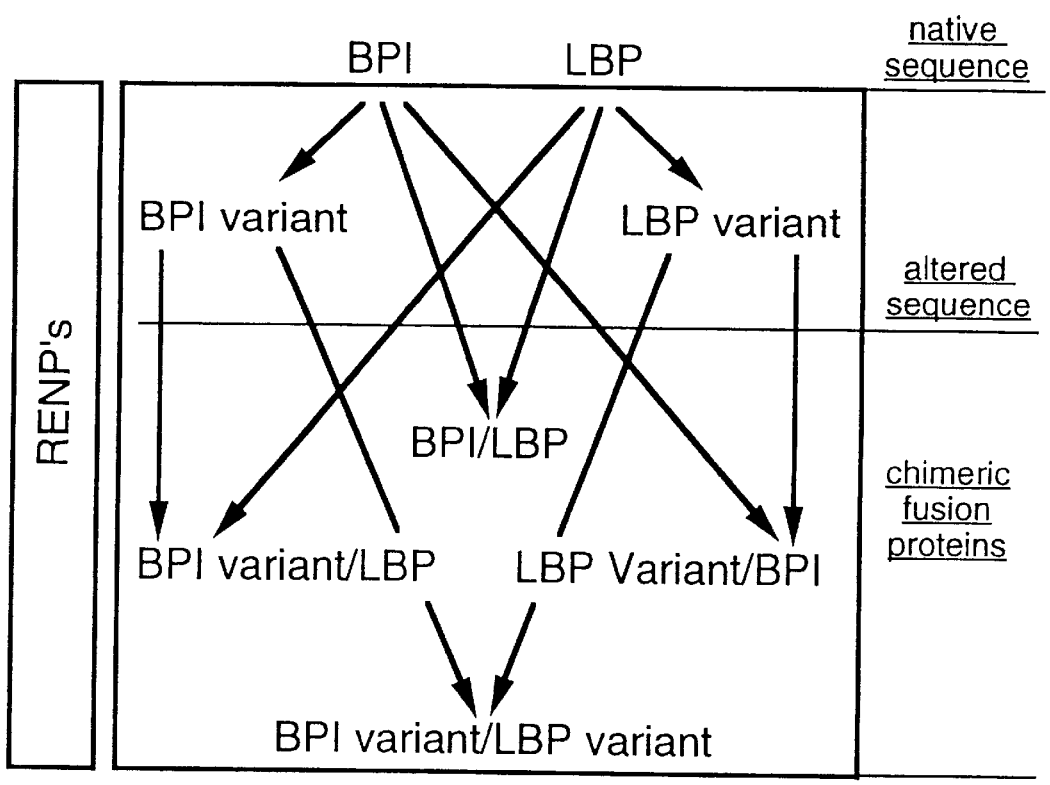
FIG. 2 is a schematic diagram showing the various combinations of BPI, LBP, BPI variants, and/or LBP variants which can be used to generate an RENPs of the invention.

Before the present recombinant endotoxin-neutralizing proteins, methods for providing therapy to a patient suffering from an endotoxin-related disorder, and compositions and method for diagnosis of a condition associated with LPS are described, it is to be understood that this invention is not limited to the particular methodology, protocols, cell lines, vectors and reagents described as such may, of course, vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a", "and", and "the" include plural referents unless the context clearly dictates otherwise. Thus, for example, reference to "a recombinant endotoxin-neutralizing protein" includes a plurality of such proteins and reference to "the DNA encoding the recombinant endotoxin-neutralizing protein" includes reference to one or more transformation vectors and equivalents thereof known to those skilled in the art, and so forth.

Unless defined otherwise, all technical and scientific terms used herein have the same meaning as commonly understood to one of ordinary skill in the art to which this invention belongs. Although any methods, devices and materials similar or equivalent to those described herein can be used in the practice or testing of the invention, the preferred methods, devices and materials are now described.

All publications mentioned herein are incorporated herein by reference for the purpose of describing and disclosing the cell lines, vectors, and methodologies which are described in the publications which might be used in connection with the presently described invention.

DEFINITIONS

By "lipopolysaccharide" or "ILPS" is meant a compound composed of a heteropolysaccharide (which contains somatic O antigen) covalently bound to a phospholipid moiety (lipid A). LPS is a major component of the cell wall of Gram-negative bacteria.

By "endotoxin" is meant a heat-stable toxin associated with the outer membranes of certain Gram-negative bacteria, including the enterobacteria, brucellae, neisseriae, and vibrios. Endotoxin, normally released upon disruption of the bacterial cells, is composed of lipopolysaccharide molecules (LPS) and any associated proteins. The phospholipid moiety of LPS, lipid A, is associated with LPS toxicity. When injected in large quantities endotoxin produces hemorrhagic shock and severe diarrhea; smaller amounts cause fever, altered resistance to bacterial infection, leukopenia followed by leukocytosis, and numerous other biologic effects. Endotoxin is a type of "bacterial pyrogen," which is any fever-raising bacterial product. The terms "endotoxin," "ILPS," and "lipopolysaccharide" as used herein are essentially synonymous.

By "recombinant endotoxin-neutralizing polypeptide", "RENP" or "recombinant LPS-neutralizing polypeptide" is meant a protein which has been genetically engineered and contains an LPS-binding domain. Preferably, such recombinant LPS-binding proteins bind endotoxin, have a relatively long half-life in serum (e.g., compared to bactericidal/permeability increasing (BPI) protein), and elicit no or relatively little of the undesirable inflammatory side effects associated with endotoxin and/or binding of LPS to particular naturally occurring endotoxin-binding proteins (e.g., lipopolysaccharide binding (LBP) protein). "RENPs" of the invention do not occur naturally and are distinct from those endotoxin-binding proteins that do occur in nature, specifically BPI and LBP.

By "LPS-binding domain" is meant an amino acid sequence which confers specific and selective LPS binding upon a polypeptide.

By "high affinity LPS binding" is meant an LPS binding affinity greater than the LPS binding affinity of LBP, preferably about the same or greater than the LPS binding affinity of BPI.

By "endotoxin-neutralizing activity" is meant a biological activity associated with inhibition of the toxic effects of lipopolysaccharide, e.g., by binding LPS and preventing interaction of LPS with proteins and/or receptors which mediate an undesirable immunological response associated with endotoxin in a mammalian host.

By "recombinant" or "genetically engineered" is meant a DNA sequence, or a polypeptide encoded thereby, generated using nucleic acid manipulation techniques (e.g., cloning, PCR, and/or fusion protein techniques). "Recombinant" or "genetically engineered" DNA, and thus the proteins encoded by such DNAs, do not occur in nature.

By "half-life" is meant the time required for a living tissue, organ, or organism to eliminate one-half of a substance introduced into it.

By "molecule which enhances the half-life" or "half-life enhancing molecule" is meant chemical moiety (e.g., bound via a chemical modification) which enhances the biological half-life of a polypeptide with which it is associated relative to the biological half-life of the parent polypeptide. Chemical moieties include an amino acid sequence or protein. For example, where a polyethylene glycol (PEG) moiety is covalently bound to a protein so as to increase the half-life of the protein relative to the un-PEGylated parent protein, the PEG moiety is the "molecule which enhances the half-life" of the protein.

By "half-life determining portion" of a polypeptide is meant an amino acid sequence which is associated with the biological half-life of the polypeptide.

By "bactericidal/permeability increasing protein" or "BPI" is meant a naturally occurring or recombinantly expressed protein having the DNA and amino acid sequences shown in FIGS. 3A–3D.

By "lipopolysaccharide binding protein" or "LBP" is meant a naturally occurring or recombinantly expressed protein having the DNA and amino acid sequences shown in FIGS. 1A–1D and FIGS. 4A–4C.

By "BPI variant" is meant a protein having an amino acid sequence similar to, but not identical to, the amino acid sequence of BPI. "BPI variants" (a) bind LPS, (b) competitively bind LPS in the presence of BPI or LBP, and (c) inhibit the LPS-mediated production of TNFα by human monocytes. In general, "BPI variants" contain the amino acid sequence of BPI but with at least one of: 1) an amino acid substitution; 2) an amino acid deletion; or 3) an amino acid addition, relative to the BPI amino acid sequence.

By "LBP variant" is meant a protein having an amino acid sequence similar to, but not identical to, the amino acid sequence of LBP. "LBP variants" (a) bind LPS, (b) competitively bind LPS in the presence of BPI or LBP, and (c) inhibits production of TNFαby human monocytes. In general, "LBP variants" contain the amino acid sequence of LBP but with at least one of: 1) an amino acid substitution; 2) an amino acid deletion; or 3) an amino acid addition, relative to the LPB amino acid sequence.

By "detectable label" is meant any molecule recognized in the art as a means for identifying and/or detecting a protein to which the detectable label is bound. Exemplary "detectable labels" include radionucleotides, fluorescent moieties, biotin, and antigenic molecules (e.g., a polypeptide which is specifically bound by an anti-polypeptide antibody). "Detectable labels" include a portion of a chimeric protein where a portion of the chimeric protein can be detected by, for example, binding of a detectably labeled antibody or other detectably labeled molecule which specifically binds the chimeric protein portion.

By "support" is meant a surface to which LPS or an RENP of the invention can be bound and immobilized. Exemplary supports include various biological polymers and non-biological polymers.

By "condition associated with endotoxin", "endotoxin associated disorder", or "endotoxin-related disorder" is meant any condition associated with extra-gastrointestinal (e.g., mucosal, blood-borne, closed space) lipopolysaccharide, e.g., a condition associated with bacteremia or introduction of lipopolysaccharide into the blood stream or onto an extra-gastrointestinal mucosal surface (e.g., the lung). Such disorders include, but are not limited to, endotoxin-related shock, endotoxin-related disseminated intravascular coagulation, endotoxin-related anemia, endotoxin-related thrombocytopenia, endotoxin-related adult respiratory distress syndrome, endotoxin-related renal failure, endotoxin-related liver disease or hepatitis, systemic immune response syndrome (SIRS) resulting from Gram-negative infection, Gram-negative neonatal sepsis, Gram-negative meningitis, Gram-negative pneumonia, neutropenia and/or leucopenia resulting from Gram-negative infection, hemodynamic shock and endotoxin-related pyresis.

By "transformation" is meant a permanent genetic change induced in a cell following incorporation of new DNA (i.e., DNA exogenous to the cell). Where the cell is a mammalian cell, the permanent genetic change is generally achieved by introduction of the DNA into the genome of the cell.

By "transformed cell" is meant a cell into which (or into an ancestor of which) has been introduced, by means of recombinant DNA techniques, a DNA molecule encoding a protein of interest.

By "promoter" is meant a minimal DNA sequence sufficient to direct transcription. "Promoter" is also meant to encompass those promoter elements sufficient for promoter-dependent gene expression controllable for cell-type specific, tissue-specific or inducible by external signals or agents; such elements may be located in the 5' or 3' regions of the native gene.

By "operably linked" is meant that a DNA sequence and a regulatory sequence(s) are connected in such a way as to permit gene expression when the appropriate molecules (e.g., transcriptional activator proteins) are bound to the regulatory sequence[]s).

By "operatively inserted" is meant that the DNA of interest introduced into the cell is positioned adjacent a DNA sequence which directs transcription and translation of the introduced DNA (i.e., facilitates the production of, e.g., a polypeptide encoded by a DNA of interest).

By "mammalian subject" or "mammalian patient" is meant any mammal for which the therapy of the invention is desired, including human, bovine, equine, canine, and feline subjects.

The invention will now be described in further detail.

Nomenclature used to describe RENPs

In order to facilitate the discussion and description of the RENPs of the invention, each RENP is designated a specific formula to briefly describe the amino acid sequence of the protein, as well as the origin of specific portions of the protein. The portion of BPI in the recombinant protein is designated with the letter B, followed by an amino acid sequence numbering assignment corresponding to that shown in FIGS. 5A–5F for human BPI, wherein the mature N-terminus is designated as residue 1. The portion of LBP in certain LBP variants and chimeras is designated by the letter L, followed by an amino acid sequence numbering assignment corresponding to that shown in FIGS. 1A–1D for human LBP, wherein the mature N-terminus is designated as residue 1. To avoid confusion between the erroneous LBP amino acid sequence published by Schumann et al., supra (designated LBP-a) and the correct LBP amino acid sequence used in the RENPs of the invention ( designated LBP-b) and presented in FIGS. 1A–1D. The differences between the DNA and amino acid sequences for "LBP-a" and "LBP-b" are presented in Table 2A below.

As an example of RENP nomenclature, $L_{1-197}B_{200-456}$ (NCY118) contains amino acid residues 1-199 of LBP fused at the C-terminus of the LBP portion to the N-terminus of amino acid residues 200-456 of BPI. $L_{1-197}B_{200-456}$, shown in FIG. 6 has the N-terminal domain of LBP (having a putative endotoxin-binding domain) fused to the C-terminal domain of BPI (having a putative LPS-clearing domain).

In this application, single amino acid residue substitutions are noted in parentheses, wherein the original amino acid residue is indicated (using the standard one letter code for amino acids), followed by the substitute amino acid residue. For example, the BPI variant having an alanine residue substituted for the original serine residue at position 351 (which substitution removes a glycosylation signal) is designated $BPI_{(S351->A)}$. In another example, in $B_{(DS200->Dp)}$, a proline residue is substituted for the serine residue at position 200. In this latter example, the amino acid substitution produces a formic acid-cleavable site.

As another example, the RENP LBP-BPI chimera NCY103 is designated $L_{1-198(I43->V)}B_{201-456(D206->N)}$. In the recombinant protein, the original isoleucine residue at position 43 of the LBP portion is substituted with a valine residue, and the original asparagine residue at position 206 of the BPI portion is substituted with an aspartate residue. The C-terminus of the LBP amino acid sequence 1-198 having isoleucine substituted at position 43 is covalently bound to the N-terminus of the BPI amino acid sequence 201-456 having valine substituted at position 206.

The amino acid substitutions may be substitutions wherein an original amino acid residue at a given position is substituted with the residue at the corresponding position in a different protein. $BPI_{(Xn->Y)}$ is an example of such a substitution, wherein amino acid residue X at position n in BPI is substituted with residue Y which is found at position n in LBP (or rabbit or bovine LBP). "X" and "Y" denote amino acid positions in a primary amino acid sequence. "Y" as used in this context is not to be confused with the symbol "Y" denoting the amino acid residue tyrosine. $LBP_{(Xn->Y)}$ is another example of such a substitution, wherein amino acid residue X at position n in LBP is substituted with residue Y which is found at position n in BPI (or rabbit or bovine BPI).

Amino acid residue insertion changes are noted in parentheses, by indicating the amino acid residue after which the insertion occurs, followed by the amino acid residue after which the insertion occurs together with the inserted residue or residues. For example, $B_{(D200papain)}$ indicates that an amino acid sequence for cleavage of the BPI variant by papain is inserted after the aspartic acid at residue position 200.

TABLE 2A

Individual Sequence Differences Between Schumann et al. and LBP as Used Herein

| NUCLEIC ACID | | PROTEIN | |
|---|---|---|---|
| Alpha | Beta | Alpha | Beta |
| $A_{42}$ | $C_{42}$ | $G_{129}YCL_{132}$ | $V_{129}TAS_{132}$ |
| $C_{318}$ | $T_{318}$ | $S_{149}$ | $F_{149}$ |
| $G_{488}$ | (np) | $A_{241}$ | $V_{241}MSLP_{245}$ |
| (np) | $C_{499}$ | $L_{411}$ | $F_{411}$ |
| $T_{546}$ | $C_{546}$ | | |
| $C_{548}$ | $T_{548}$ | | |
| (np) | $T_{824}CATGAGCCTTC_{835}$ | | |
| $C_{1333}$ | $T_{1333}$ | | |

(np) = not present in the sequence

Table 2B describes some exemplary general classes of RENPs of the invention. In the formulas in Table 2B, n represents an amino acid residue position in the mature sequence of BPI or LBP, x represents an amino acid residue in a position which is C-terminal to n in the sequence of BPI or LBP, and y represents an amino acid residue in a position which is C-terminal to x in the sequence of BPI or LBP. The symbols n, x and y denote the amino acid residue positions as they occur in the mature sequence of the native protein, and not necessarily the positions as they occur in the variant protein.

TABLE 2B

Examples of RENPs

| | |
|---|---|
| BPI variant (N-terminal frag.) | $B_{1-n}$ |
| LBP variant (N-terminal frag.) | $L_{1-n}$ |
| BPI variant (C-terminal frag.) | $B_{n-456}$ |
| LBP variant (C-terminal frag.) | $L_{n-456}$ |
| BPI variant (internal frag.) | $B_{n-x}$ |
| LBP variant (internal frag.) | $L_{n-x}$ |
| LBP-BPI chimera | $L_{n-x}B_{(x+1)-y}$ |
| BPI-LBP chimera | $B_{n-x}L_{(x+1)-y}$ |
| LBP-BPI chimera | $L_{n-x}B_{(x+1)-456}$ |
| BPI-LBP chimera | $B_{n-x}L_{(x+1)-456}$ |
| LBP-BPI chimera | $L_{1-n}B_{(n+1)-x}$ |
| BPI-LBP chimera | $B_{1-n}L_{(n+1)-x}$ |
| LBP-BPI chimera | $L_{1-n}B_{(n+1)-456}$ |
| BPI-LBP chimera | $B_{1-n}L_{(n+1)-456}$ |
| LBP-BPI-LBP chimera | $L_{1-n}B_{(n+1)-x}L_{(x+1)-456}$ |
| BPI-LBP-BPI chimera | $B_{1-n}L_{(n+1)-x}B_{(x+1)-456}$ |

All of the constructs in Table 2B can also contain additional molecules which confer an enhanced half-life upon the RENP (e.g., the RENP can be covalently bound to a polyethylene glycol moiety, or a portion of an immunoglobulin protein or other amino acid sequence which confers a half-life increased relative to the unmodified protein). The general scheme for generation of RENPs is outlined in FIG. 2.

Production of RENPs

The RENPs of the invention minimally have characteristics associated with (i) specific and high affinity binding to lipopolysaccharide and (ii) endotoxin-neutralizing activity. In general, the amino acid sequence of RENPs is based upon an amino acid sequence of BPI, LBP, or both. However, the amino acid sequences of the RENPs are distinct from that of BPI and LBP, i.e. the RENPs contain amino acid substitutions, deletions, and/or additions relative to the amino acid sequence of BPI or LBP. Thus, the RENPs of the invention contain: 1) amino acid sequences of a naturally-occurring LPS-binding protein (i.e., LBP and/or BPI); and/or 2) amino acid sequences which do n occur within a single naturally-occurring LPS-binding protein (i.e., LBP or BPI). RENPs can thus be similar to, but not identical to, LBP or BPI. For example, the RENPs can be fragments of BPI and/or LBP, as the amino acid sequences of such RENPs are similar to, but not identical to, naturally occuring BPI or LBP. Moreover, the RENPs of the invention generally have biological properties distinct from and advantageous to either BPI or LBP. RENPs of the invention include BPI variants, LBP variants, and chimeric proteins composed of amino acid sequences derived from BPI, LBP, BPI variants, and/or LBP variants.

For example, RENPs can contain an amino acid sequence of BPI, where the BPI amino acid sequence 1) has been altered at a site of glycosylation (e.g., insertion or deletion of a glycosylation site); 2) contains a neutral or anionic amino acid substituted at a cationic residue of the BPI amino acid sequence (cationic substitution variants); 3) contains an amino acid substitution at a position normally occupied by cysteine in the BPI sequence (cysteine substitution variants); 4) contains an amino acid substitution where the substituted amino acid is the amino acid at the corresponding position in the LBP amino acid sequence; and/or 5) contains an insertion or deletion of one or more secondary structure-altering amino acid residues.

Exemplary BPI variants containing a glycosylation site alteration include BPI variants having an amino acid residue other than serine substituted for the serine residue fiat position 351 of the BPI amino acid sequence. BPI variants of this type are of the formula BPI(S351->X), wherein X is any amino acid other than serine. Preferably, the amino acid substituted at position 351 is alanine. Other BPI variants having a glycosylation site deleted can be generated by, for example, other amino acid substitutions within the glycosylation site.

Additional exemplary BPI variants contain a neutral or anionic amino acid substituted at a cationic residue of the BPI amino acid sequence (cationic substitution variants). For example, one or more of the nonconserved positively-charged residues in BPI (i.e., those residues not found at the corresponding positions in LBP) can be substituted with the corresponding residue or residues in LBP, thus rendering BPI less cationic. Preferably, the cationic substitution variant contains an amino acid substitution in at least one of BPI amino acid residue positions 27, 30, 33, 42, 44, 48, 59, 77, 86, 90, 96, 118, 127, 148, 150, 160, 161, 167, 169, 177, 185, or 198. The cationic substitution variant can contain multiple amino acid substitutions. For example, the cationic substitution variant can contain a neutral or anionic residues at 1) BPI amino acid residue positions 27, 30, 33, 42, 44, 48, and 59; 2) BPI amino acid residue positions 77, 86, 90, 96, 118, and 127; 3) BPI amino acid residue positions 148, 150, 160, 161, 167, 169, 177, 185, and 198; or 4) BPI amino acid residue positions 27, 30, 33, 42, 44, 48, 59, 77, 86, 90, 96, 118, 127, 148, 150, 160, 161, 167, 169, 177, 185, and 198.

Further example BPI variants contain an amino acid substitution at a position normally occupied by cysteine in the BPI sequence (cysteine mutant). The amino acid selected for substitution at this site can be the amino acid in the corresponding position in LBP. For example, a cysteine residue in BPI (which is not conserved in LBP) may be substituted with an alanine residue (the corresponding residue in LBP). Preferably, the amino acid substitution is at a cysteine residue at BPI amino acid residue position 132, 135, or 175. Preferably, alanine or serine is substituted for cysteine. More preferably, alanine is substituted for the cysteine at position 132 of BPI. Cysteine substitution mutants of BPI can prevent aggregation of the resulting RENPs during their production or use.

Another example of a BPI variant includes a BPI variant having an amino acid substitution where the substituted amino acid is the amino acid at the corresponding position in LBP. The amino acid at the corresponding position is determined by aligning the BPI and LBP amino acid sequences so as to maintain the highest level of amino acid sequence identity between the two sequences. For example, an RENP having the formula $B_{(Q329 \rightarrow S)}$ contains a substitution of the glutamine at BPI residue position 329 with the serine residue at the corresponding LBP residue position 327 (see FIGS. 5A–5F).

Additional exemplary BPI variants contain an insertion or deletion of one or more secondary structure-altering amino acid residues. For example, one or more of the nonconserved proline residues in BPI may be substituted with the corresponding non-proline residue in LBP.

Alternatively, or in addition to the amino acid sequence of BPI and/or a BPI variant, the RENPs can contain an amino acid sequence of LBP, where the LBP amino acid sequence 1) has been altered at a site of glycosylation (e.g., insertion or deletion of a glycosylation site); 2) contains a cationic amino acid substituted at a neutral or anionic amino acid of the LBP amino acid sequence (cationic replacement mutant); 3) contains an amino acid substitution where the substituted amino acid is the amino acid at the corresponding position in the BPI amino acid sequence; and/or 4) contains an insertion or deletion of one or more secondary structure-altering amino acid residues. The LBP DNA and amino acid sequence used in the construction of particular RENPs exemplified herein is the amino acid sequence of human LBP in FIGS. 5A–5B.

Exemplary LBP variants contain a cationic amino acid substituted at a neutral or anionic amino acid of the LBP amino acid sequence (cationic replacement variant). For example, one or more of the nonconserved amino acid residues in LBP (at a position which corresponds to a positively-charged residue in BPI) may be substituted with the corresponding positively-charged residue in BPI, and thus result in an LBP variant having an increased positive charge, thus enhancing binding to the negatively charged phosphate groups in LPS, and/or facilitating interaction with the negatively charged surfaces of Gram-negative bacteria. Positively-charged residues include, by way of example, lysine, arginine, and histidine. Preferably, the substituted cationic amino acid is at least one of LBP amino acid residue positions 77, 86, 96, 118, 126, 147, 148, 158, 159, 161, 165, 167, 175, 183, or 196. Cationic replacement variants can contain multiple amino acid residue substitutions at any combination of the amino acid residues recited above.

Other exemplary LBP variants include an LBP variant having an amino acid substitution where the substituted amino acid is the amino acid at the corresponding position in BPI. For example, $L_{(A401 \rightarrow D)}$ contains a substitution of the alanine residue of LBP at position 401 with the aspartic acid residue at the corresponding BPI residue position 403.

Further exemplary LBP variants contain an insertion or deletion of one or more one or more secondary structure-altering amino acid residues. For example, one or more of the nonconserved amino acid residues in LBP (at a position which corresponds to a proline in BPI) may be substituted with a proline residue. Preferably, such amino acid alterations alter the secondary structure of the resulting LBP variant so that it is more like the secondary structure of BPI.

Preferably, the RENPs of the invention contain at least one LPS-binding domain of BPI, LBP, a BPI variant, and/or a LBP variant. For example, the LPS-binding domain can be derived from BPI and/or LBP amino acid sequences 17-45, 65-99, and/or 141-167. Preferably, the RENP has an LPS binding affinity that is greater than the LPS binding affinity of LBP, more preferably an LPS binding affinity that is the same or greater than the LPS binding affinity of BPI. Preferably, the RENP has an LPS binding affinity that is about 25-fold to 50-fold, preferably about 50-fold to 100-fold, more preferably about 100-fold to 300-fold greater than the LPS binding affinity of LBP as determined by LPS binding or LPS binding competition assays. The LPS binding affinity of BPI is about 60-fold to 100-fold greater than the LPS binding affinity of LBP.

The RENPs can contain multiple LPS-binding domains derived from any of these LPS-binding proteins. For example, an RENP can be a multivalent chimeric protein (i.e., a fusion protein) composed of an LPS-binding domain of BPI covalently bound (i.e., as in a fusion protein) to an LPS-binding domain of LBP. As used herein, a chimera means a protein comprising all or a portion of a first protein fused to all or a portion of a second protein, which resulting fusion protein may in turn be fused to all or a portion of a third protein. Examples of chimeras include, by way of example, (a) a protein comprising a portion of LBP fused to a portion of BPI, (b) a protein comprising a portion of LBP fused to a portion of BPI which portion of BPI is in turn fused to a portion of an immunoglobulin protein, or (c) a protein comprising a portion of LBP fused to a portion of BPI, which is in turn fused to a portion of LBP. Each protein portion of the chimera may comprise a fragment of the protein, a point mutant of the protein (i.e., a variant), a deletion mutant of the protein, or a point and deletion mutant of the protein.

Examples of BPI fragments which can be incorporated into the RENPs of the invention include the BPI amino acid sequences 1-25, 1-85, 1-137, 1-135, 1-147, 1-159, 88-100, 148-161, 137-199, 44-159, 44-199, 135-199, 100-199, 162-199, 100-147. Examples of LBP fragments which can be incorporated into the RENPs of the invention include LBP amino acid sequences 1-43, 1-87, 26-135, 26-134, 86-99, 101-146, 101-197, 135-197, 137-197, 158-197, 160-197, and/or 147-159. The amino acid sequences of BPI and/or LBP can be combined in any order from N- to C-terminus to provide an RENP having sequences derived from BPI and/or LBP. For example, the RENPs can have the sequences $B_{1-137}L_{137-197}$, $L_{1-43}B_{44-199}$, $B_{1-159}L_{158-197}$, $B_{1-135}L_{135-197}$, $L_{1-43}B_{44-159}L_{158-197}$, $B_{1-25}L_{26-135}B_{137-199}$, $B_{1-25}L_{26-134}B_{135-199}$, $L_{1-87}B_{88-100}L_{101-146}B_{148-161}L_{160-197}$, $B_{1-85}L_{86-99}B_{100-199}$, $B_{1-147}L_{147-159}B_{162-199}$, $B_{1-85}L_{86-99}B_{100-147}L_{147-159}$ $B_{162-199}$, $L_{1-87}$ $B_{88-100}L_{101-197}$, or various combinations of other BPI and/or LBP fragments.

RENPs can share properties of both BPI and LBP. For example, fusing the N-terminal domain of LBP to the C-terminal domain of BPI results in an RENP which differs from LBP in that the chimera neutralizes endotoxin in whole blood and differs from BPI in that the chimera has a longer circulating half-life in vivo. Such RENPs have significant diagnostic and therapeutic potential. As per the nomenclature described above, RENPs designated BPI-LBP contain all or a part of the N-terminal domain of BPI fused to all or a part of the C-terminal domain of LBP. Likewise, RENPS designated LBP-BPI contain all or a part of the N-terminal domain of LBP fused to all or a part of the C-terminal domain of BPI.

Where the RENP contains amino acid sequences derived from both BPI and LBP, the RENP is preferably composed of a C-terminal fragment of BPI (or a BPI variant) and an N-terminal fragment of LBP (or an LBP variant). Preferably the C-terminal fragment of BPI (or a BPI variant) contains amino acid residues 60-456, 136-456, 199-456, 277-456, 300-456, 200-456, 136-361, 136-275, 200-275, or 200-361, more preferably 60-456, more preferably 199-359. The amino acid sequence of BPI from residue 199 to residue 359 contains a region required for neutralizing LPS, i.e., preventing LPS from stimulating an inflammatory response. Preferably, the N-terminal fragment of LBP (or an LBP variant) contains amino acid residues 1-59, 1-134, 1-164, 1-175, 1-274, 1-359, 1-134, or 1-197, more preferably 1-175. In addition to the specific amino acid sequences of BPI and LBP recited above, the RENP can also contain amino acid residues derived from the C-terminus of LBP (or an LBP variant), preferably LBP (or LBP variant) amino acid residues 360-456 or 274-456.

Polypeptides which bind LPS can be identified using any of several assays well known in the art such as the 1) chromogenic LAL competition assay, 2) binding to LPS immobilized on a surface, and 3) FITC-LPS assay for binding to macrophages. The ability of a polypeptide to neutralize endotoxin can also be determined using methods well known in the art. Endotoxin neutralization assays include assays to examine the ability of a polypeptide to 1) prevent LPS-induced TNF release in whole blood, 2) inhibit or prevent TNF production by THP-1 cells, 3) provide protection in a mouse endotoxin challenge assay, and 4) reduce or prevent LPS-induced cytokine release and/or mortality in an animal model. Each of these assays are described in detail in the examples section below. The results of the in vitro and in vivo assays used herein are accepted in the art. The results of these assays are predictive of relevant biological activity in vivo, e.g. in humans.

Preferably, the RENPs of the invention have a biological half-life (e.g., serum half-life) which is enhanced relative to the biological half-life of BPI. Preferably, the half-life of the RENP is enhanced relative to BPI such that the clearance time of the RENP is at least 1.5-fold to 10-fold, preferably about 10-fold to 50-fold, more preferably about 50-fold to 100-fold, even more preferably about 100-fold to 350-fold slower than the clearance rate of BPI. The clearance rate values representing these ranges are from about 8 ml/min to 1.5 ml/min, preferably 1.5 ml/min to 0.26 ml/min, more preferably 0.26 ml/min to 0.13 ml/min, even more preferably about 0.13 ml/min to 0.03 ml/min.

To enhance the RENP half-life, the RENP can be covalently bound to a molecule which enhances the half-life of the polypeptide. The half-life enhancing molecule can be any of a variety of half-life enhancing molecules. Exemplary half-life enhancing molecules include immunoglobulin fragments, a half-life determining portion of LBP, a half-life determining portion of an LBP variant, or polyethylene glycol (PEG), preferably a half-life determining portion of LBP or an LBP variant. Preferably, where the half-life enhancing molecule is a portion of LBP or an LBP variant, the half-life enhancing molecule is derived from the N-terminus of the LBP or LBP variant amino acid sequence, more preferably from amino acid residues 1-59, 1-134, 1-274, 1-359, 1-134, 1-164, 1-175, or 1-197, most preferably 1-164 or 1-175. Methods of attachment of PEG moieties to a protein (i.e., PEGylation) are well known in the art and are exemplified in U.S. Pat. Nos. 4,179,337; 5,166,322; 5,206,344; and PCT application Ser. No. PCT/US94/11624, published Apr. 28, 1995.

As used herein, an RENP-Ig chimeric protein is an RENP which (i) contains a portion of BPI or LBP (at least 10 amino acid residues in length of (a) BPI, or (b) BPI variant, or (c) LBP, and/or (d) LBP variant) fused at the C-terminus the N-terminus the Fc portion of an immunoglobulin molecule, and (ii) is capable of (a) binding to LPS, (b) competing with BPI or LBP for binding to LPS, and (c) inhibiting the production of TNFα by human monocytes. For example, the portion of the immunoglobulin molecule is derived from an IgG molecule, specifically from an IgG, heavy chain Fc domain. RENP-Ig chimera is a fusion protein composed predominantly of sequences derived from BPI, variant BPI, LBP and/or variant LBP. The term "LBP-BPI-IgG chimera" indicates that the RENP-Ig chimera contains amino acid sequences derived from both BPI (or a BPI variant) and LBP (or an LBP variant).

Identification of a half-life enhancing polypeptide sequence (e.g., a polypeptide derived from an immunoglobulin, LBP, or LBP variant) can be accomplished using methods well known in the art. For example, the test polypeptide with and without the half-life enhancing molecule bound to it are injected into an animal model to determine the effects of the putative half-life enhancing molecule. If the half-life of the polypeptide with the molecule is enhanced relative to the half-life of the polypeptide without the molecule, then the molecule is a half-life enhancing molecule suitable for use in the RENPs of the invention. For example, a putative half-life enhancing amino acid sequence is incorporated into a fusion protein with BPI. Both native BPI and the BPI fusion protein are injected into mice. If the BPI fusion protein has a half-life significantly greater than the half-life of native BPI, then the amino acid sequence in the BPI fusion has half-life enhancing characteristics, and thus can be incorporated into the RENPs of the invention.

Vectors and Constructs

Any nucleic acid vector can be used to express DNA encoding an RENP of the invention. The vectors containing the DNA sequence (or the corresponding RNA sequence) which may be used in accordance with the invention may be any prokaryotic or eukaryotic expression vector containing the DNA (e.g., cDNA) or the RNA sequence of interest. A variety of suitable vectors are publicly available and well known in the art. For example, a plasmid can be cleaved to provide linear DNA having ligatable termini. These termini are bound to exogenous DNA having complementary, like ligatable termini to provide a biologically functional recombinant DNA molecule having an intact replicon and a desired phenotypic property.

A variety of techniques are available for DNA recombination in which adjoining ends of separate DNA fragments are tailored to facilitate ligation. The vector is constructed using known techniques to obtain a transformed cell capable of expression of the RENP. The transformed cell is obtained by contacting a target cell with a RNA- or DNA-containing formulation permitting transfer and uptake of the RNA or DNA into the target cell. Such formulations include, for example, plasmids, viruses, liposomal formulations, or plasmids complexed with polycationic substances such as poly-L-lysine or DEAC-dextran, and targeting ligands. Transformed cells containing a construct encoding an RENP of the invention are also known in the art as "host vector systems". Vectors for use in the construction of constructs encoding the RENPs of the invention, as well as methods for molecular cloning, nucleic acid manipulation, and transformation of both eukaryotic and prokaryotic host cells are well known in the art (see, for example, Sambrook et al. *Molecular Cloning: A Laboratory Manual,* 2nd Ed., 1989, Cold Spring Harbor Laboratory Press, Cold Spring Harbor, NY; hereby incorporated by reference with respect to bacterial and eukaryotic vectors, and methods and compositions for molecular cloning, nucleic acid manipulation, and transformation techniques).

The constructs of the invention may include promoter sequences to enhance expression of the RENP-encoding DNA, as well as other sequences (e.g., enhancers) which facilitate or enhance DNA expression. In addition, the RENP-encoding constructs can contain other components such as a marker (e.g., an antibiotic resistance gene (such as an ampicillin resistance gene) or β-galactosidase) to aid in selection of cells containing and/or expressing the construct, an origin of replication for stable replication of the construct in a bacterial cell (preferably, a high copy number origin of replication), a nuclear localization signal, or other elements which facilitate production of the DNA construct, the protein encoded thereby, or both.

In general, the RENPs of the invention are constructed from a DNA sequence encoding BPI, a BPI variant, LBP, an LBP variant, as well as various half-life enhancing molecules known in the art such as immunoglobulin fragments. Both BPI and LBP have been cloned and their DNA and amino acid sequences determined (FIGS. 3A–3B and 4A–4B, respectively). The DNA and amino acid sequences of numerous immunoglobulins are known in the art. For example, the DNA sequence of IgG, $IgG_{2a}$, and $IgG_4$ are suitable for use to enhance the half-life of the RENPs of the invention.

Expression of Recombinant Endotoxin-neutralizing Polypeptides

Techniques for obtaining expression of exogenous DNA or RNA sequences in a host cell are known in the art (see, for example, Sambrook et al., supra; hereby incorporated by reference with respect to methods and compositions for eukaryotic and prokaryotic expression of a DNA encoding an RENP). Where the transformed cell is a prokaryotic host cell, the preferred host is *Escherichia coli*. Where the transformed cell is a eukaryotic host cell, preferably the host cell is a mammalian cell or a yeast cell. Preferably, the mammalian host cell is a Chinese Hamster Ovary (CHO) cell. Preferably, the yeast host cell is of the genus Pichia, more preferably a strain of *Pichia pastoris*.

For prokaryotic expression, the construct should contain at a minimum a bacterial origin of replication and a bacterial promoter operably linked to the RENP-encoding DNA. For eukaryotic expression, the construct should contain at a minimum a eukaryotic promoter operably linked to a DNA of interest, which is in turn operably linked to a polyadenylation sequence. The polyadenylation signal sequence may be selected from any of a variety of polyadenylation signal sequences known in the art. Preferably, the polyadenylation signal sequence is the SV40 early polyadenylation signal sequence. The eukaryotic construct may also include one or more introns, which can increase levels of expression of the DNA of interest, particularly where the DNA of interest is a cDNA (e.g., contains no introns of the naturally-occurring sequence). Any of a variety of introns known in the art may be used. Preferably, the intron is the human β-globin intron and inserted in the construct at a position 5' to the DNA of interest.

Purification of RENPs

Purification of the RENPs of the invention can be performed according to any of a variety of protein purification techniques known in the art including gel electrophoresis, immunoprecipitation, ion exchange chromatography, affinity chromatography, or combinations thereof (see, for example, *Guide to Protein Purification,* Deutscher, ed., Academic Press, Inc., San Diego, Calif., 1990). Preferably, purification of RENPs is accomplished by a combination of column chromatographic techniques. For example, RENPs can be purified using a four-step purification procedure using 1) a cation exchange column (e.g., CM Sepharose), 2) an anion exchange column (e.g., Fast Q Sepharose), 3) a second cation exchange column (e.g., CM Sepharose), and 4) a gel filtration sizing column (e.g., Sepharose CL6B).

Pharmaceutical Compositions

The RENPs of the invention can be formulated as an active ingredient in a pharmaceutical composition. In general, the pharmaceutical composition contains a therapeutically effective amount of an RENP and a pharmaceutically acceptable carrier. The pharmaceutical composition can contain one or more RENPS. The amount of RENP which constitutes a therapeutically effective amount will vary according to the time of administration (e.g., therapeutic or prophylactic administration), the disease or condition to be treated, the route of administration, and various patient-dependent factors such as age, weight, gender, and severity of disease. Specific therapeutically effective amounts appropriate for administration are readily determined by one of ordinary skill in the art (see, for example, *Remington's Pharmaceutical Sciences,* 18th ed., Gennaro, ed., Mack Publishing Company, Easton, Pa., 1990).

Pharmaceutically acceptable carriers suitable for use in the RENP-containing pharmaceutical compositions of the invention are well known to those skilled in the art. Selection of the pharmaceutically acceptable carrier will depend upon a variety of factors including the RENP to be administered, the route of administration, and the condition to be treated.

Pharmaceutically acceptable carriers suitable for use with the RENPs of the invention include, but are not limited to, 0.01–0.1 M and preferably 0.05 M succinate buffer or 0.8% saline. Additionally, such pharmaceutically acceptable carriers may be aqueous or non-aqueous solutions, suspensions, and emulsions. Further, pharmaceutically acceptable carriers may include detergents, phospholipids, fatty acids, or other lipid carriers. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's or fixed oils.

Pharmaceutically acceptable carriers for use with the RENPs of the invention include lipid carriers. A lipid carrier is any lipid-soluble substance which inhibits protein precipitation and in which the proteins of the subject invention are soluble. Lipid carriers can be in the form of sterile solutions or gels, or can be detergents or detergent-containing biological surfactants. Examples of nonionic detergents include polysorbate 80 (also known as TWEEN 80 or polyoxyethylenesorbitan monooleate). Examples of ionic detergents include, but are not limited to, alykltrimethylammonium bromide. Exemplary lipid carriers and methods for solubilizing BPI, and thus which can be used in pharmaceutical compositions containing an RENP of the invention, are described in U.S. Pat. No. 5,234,912, incorporated herein by reference.

Where the pharmaceutically acceptable carrier is a lipid carrier, the lipid carrier may be a liposome. A liposome is any phospholipid membrane-bound vesicle capable of containing a desired substance, such as BPI or BPI variant, in its hydrophilic interior. Intravenous vehicles include fluid and nutrient replenishers, electrolyte replenishers such as those based on Ringer's dextrose, and the like. Preservatives, other pharmaceutically active compounds, and other additives may also be present, such as, for example, antimicrobials, antioxidants, chelating agents, inert gases and the like.

Disease Conditions Amenable to Treatment with RENPs

Various disease conditions are amenable to treatment using the recombinant LPS-neutralizing proteins of the invention. In general, any condition of a mammalian subject (e.g., human, canine, feline, or bovine, preferably a human) which is associated with a toxic effect of endotoxin can be treated by administration of the RENPs of the invention. Endotoxin-related disorders amenable to treatment include, but are not limited to, endotoxin-related shock, endotoxin-related disseminated intravascular coagulation, endotoxin-related anemia, endotoxin-related thrombocytopenia, endotoxin-related adult respiratory distress syndrome, endotoxin-related renal failure, endotoxin-related liver disease or hepatitis, systemic immune response syndrome (SIRS) resulting from Gram-negative infection, Gram-negative neonatal sepsis, Gram-negative meningitis, Gram-negative pneumonia, neutropenia and/or leucopenia resulting from Gram-negative infection, hemodynamic shock and endotoxin-related pyresis. Endotoxin-related pyresis is associated with certain medical procedures, such as, for example, trans-urethral resection of the prostate, and gingival surgery. The presence of endotoxin may result from infection at any site with a Gram-negative organism, or conditions which may cause ischemia of the gastrointestinal tract, such as hemorrhage, or surgical procedures requiring extracorporal circulation. The important role of endotoxin in hemorrhage (with endogenous LPS translocation from the gut), trauma, and sepsis is well known. One skilled in the art can recognize additional conditions which can be treated using the therapy of the invention.

The recombinant, endotoxin-neutralizing proteins of the invention can also be administered to a patient prophylactically, e.g. to a patient at risk of an endotoxin-related disorder. For example, the RENPs can be administered to a patient who has a Gram-negative infection and is at risk of bacteremia, but who has not yet exhibited symptoms associated with the toxic effects of endotoxin. The RENPs can also be administered prior to surgery where the risk of introduction of endotoxin into the patient is substantial. One of ordinary skill in the art can readily recognize other instances in which prophylactic administration of a RENP is appropriate. The conditions which identify an individual as being at risk of an endotoxin-related disorder are well known in the art.

Administration of RENPs

The recombinant, LPS-binding protein of the invention may be administered using various methods well known in the art. U.S. Pat. Nos. 5,171,739; 5,308,834; and 5,334,584; each incorporated herein by reference, describe methods and compositions for administration of BPI, and thus can provide additional guidance for administration of the RENPs of the invention. For example, the recombinant, LPS-binding protein can be administered by injection or inhalation. Administration by injection can be an intravenous, intramuscular, or subcutaneous route, or by direct injection directly into a site of infection (e.g., tissue or body cavity). Preferably, injection is intravenous. Administration by inhalation is accomplished by delivery of the RENP to the lungs via an aerosol delivery system or via direct instillation. The aerosol may be nebulized. Various devices and methods for aerosol drug delivery are well known in the art. Methods for determining the appropriate route of administration and dosage are generally determined on a case-by-case basis by the attending physician. Such determinations are routine to one of ordinary skill in the art (see, for example, *Remington's Pharmaceutical Sciences*, 18th ed., Gennaro, ed., Mack Publishing Company, Easton, Pa., 1990).

Therapeutically effective amounts of an RENP can be determined according to methods well known to those skilled in the art. Specific dosages will vary according to a variety of factors, including the time of administration (e.g., therapeutic or prophylactic administration), the disease or condition to be treated, the route of administration, the RENP to be administered, and various patient-dependent factors such as age, weight, gender, and severity of disease. The specific dosage appropriate for administration is readily determined by one of ordinary skill in the art according to the factors discussed above (see, for example, *Remington's Pharmaceutical Sciences*, 18th ed., Gennaro, ed., Mack Publishing Company, Easton, Pa., 1990). In addition, the estimates for appropriate dosages in humans may be extrapolated from determinations of the in vitro LPS binding affinity of the RENP used, the amount of the RENP effective to inhibit cytokine production by mononuclear cells in vitro, the amount of RENP effective to provide protection to LPS challenge, and/or various other in vitro and in vivo assays indicative of the biological activity of the RENP.

In general, the amount of RENP administered is an amount effective to bind LPS and thereby inhibit the undesirable biological activities associated with LPS including monocyte and neutrophil activation, TNF production, cytokine production, and other biological phenomena triggered by LPS in endotoxin-related disorders. Preferably, the amount of RENP administered is an amount effective to bind LBP and inhibit LPS-mediated stimulation of neutrophils and mononuclear cells.

In therapeutic administration of the RENPs of the invention, an effective amount of an RENP is an amount effective to bind to LPS and thereby inhibit LPS-mediated stimulation of neutrophils and mononuclear cells in a subject having an endotoxin-related disorder. As used herein, "inhibit" means to inhibit at a level which is statistically significant and dose dependent. The terms "statistically significant" and "dose dependent" are well known to those skilled in the art. In general, an effective amount of an RENP in a pharmaceutical composition for treatment of a patient having an endotoxin-related disorder is an amount sufficient to deliver to the subject a recombinant protein of the subject invention at a concentration of between about 0.1 mg/kg of body weight and about 100 mg/kg of body weight, preferably between about 1 mg/kg of body weight and about 10 mg/kg of body weight. Preferably, the RENP(s) is administered by injection, infusion, or as an injected bolus so as to maintain a circulating RENP concentration of about 1-10 $\mu$g/ml. The preferred circulating RENP concentration can vary according to a variety of factors, including the LPS binding affinity of the specific RENP(s) administered.

As used herein, a prophylactically effective amount of an RENP in a pharmaceutical composition for the prevention of an endotoxin-related disorder is an amount effective to bind LPS and prevent LPS-mediated biological activity, e.g., LPS-mediated stimulation of monocytes and neutrophils. In general, a prophylactically effective amount of an RENP is an amount of a composition effective to deliver between about 0.1 mg/kg of body weight and about 100 mg/kg of body weight, preferably between about 1 mg/kg of body weight and about 10 mg/kg of body weight, to the patient at risk of an endotoxin-related disorder.

The invention also provides an article of manufacture comprising packaging material and a pharmaceutical composition contained within the packaging material. The packaging material includes a label which indicates that the pharmaceutical composition can be used for treating a subject suffering from an endotoxin-related disorder and/or for preventing an endotoxin-related disorder (e.g., inflammation) in a subject. The pharmaceutical composition contains a therapeutically effective and/or prophylactically effective amount of an RENP and a pharmaceutically acceptable carrier.

Assessment of Therapy

The efficacy of the therapeutic or prophylactic use of the RENPs of the invention can be determined by monitoring patient symptoms associated with an endotoxin-related disorder. Such symptoms, and methods for monitoring, are well known in the art. For example, where the RENP is used in the treatment of a patient having an endotoxin-related disorder, the effectiveness of the RENP therapy can be assessed by monitoring fever, blood pressure, cytokine levels, and/or LPS levels in the patient's blood stream. The presence of LPS in the blood stream can be assayed as described above. Where the patient is not responding, it may be desirable to increase the dosage of the RENP pharmaceutical composition or, where the patient is not responding favorably, discontinue the RENP regimen.

Detectably-labeled RENPs

Various detectable labels, as well as methods of attachment of such labels to a protein, are well known in the art. Detectable labels can be any molecule recognized in the art as a means for identifying and/or detecting a protein to which the detectable label is bound. Exemplary "detectable labels" include, but are not limited to radionucleotides, fluorescent moieties, biotin, and antigenic molecules (e.g., a polypeptide which can be specifically bound by an anti-polypeptide antibody). Thus, detectable labels include a portion of a chimeric protein (e.g., a fusion protein or genetically engineered protein) where a portion of the chimeric protein can be detected by, for example, binding of a detectably labeled antibody or other detectably labeled molecule which specifically binds the chimeric protein portion. For example, where the RENP contains a portion of the amino acid sequence of BPI, and an antibody which specifically binds that amino acid sequence of BPI in the context of the RENP is available, the BPI amino acid sequence is the detectable label.

Methods for attaching (e.g., covalently binding) a detectable label to a protein are well known in the art. For example, methods for preparation of $^{125}$I-labeled proteins, biotin-labeled proteins, and FITC-labeled proteins are well known. Methods for detectably labeling antibodies are also well known in the art. Methods for the production of antibodies for use in the subject invention (e.g., anti-BPI, anti-LBP, anti-BPI variant, anti-LBP variant, and anti-immunoglobulin fragment antibodies) are well known in the art (see, for example, *Antibodies: A Laboratory Manual,* Harlow and Lane, eds., Cold Spring Harbor Laboratory, Cold Spring Harbor, N.Y., 1988).

Detection of LPS in vitro

The detectably labeled RENPs of the invention can be used in various methods for the detection of LPS either in vitro or in vivo. Samples for which in vitro LPS detection is desirable include samples from a patient suspected of having a Gram-negative infection, and samples from a product for use in a medical application (e.g., a recombinant protein solution where the protein was expressed in *E. coli*). Patient samples include samples of any body fluid, preferably blood or urine. Samples may be pre-treated prior to testing by, for example, concentrating the sample, or centrifugation to remove cells and cellular debris.

In general, in vitro detection of LPS in a sample suspected of containing LPS (test sample) is performed by contacting the test sample with an RENP of the invention for a time sufficient for the formation of RENP-LPS complexes, and the RENP-LPS complexes detected. The RENP-LPS complexes can be detected by virtue of a detectable label attached to the RENP, or by the binding of an anti-LPS antibody. Binding of the anti-LPS antibody can subsequently be detected by virtue of a detectable label bound to the antibody, or by the binding of a detectably labeled anti-anti-LPS antibody to the RENP-LPS-antibody complex.

The in vitro assay can be performed in solution by mixing the sample with a solution containing RENP, separation of RENP-LPS complexes (e.g., by immunoprecipitation), and detection of the RENP-LPS complexes formed, e.g., by virtue of a detectable label bound to the RENP. Alternatively, the in vitro assay is performed with RENP bound to a support, e.g., a polymeric substrate such as a microtiter well or a latex bead. Methods for binding proteins to a support are well known in the art. For example, an anti-RENP antibody can be bound to the support and the RENP subsequently bound to the support via binding to the anti-RENP antibody. After binding of the RENP to the support, the sample is then contacted with the support-bound RENP and any LPS in the sample allowed to bind to the RENP. Unbound material is then washed away, and the RENP-LPS complexes detected by the binding of detectably labeled RENP or detectably labeled anti-LPS antibody.

The in vitro assay can also be performed as a competition binding assay. For example, a sample suspected of containing LPS (test sample) and a known amount of detectably labeled RENP are incubated together with a support having LPS bound to its surface. The test sample and the RENP may be preincubated prior to contact with the support-bound RENP. The level of detectably labeled RENP bound to the support in the test sample is compared to the level of detectably labeled RENP bound to the support in a negative control sample (detectably labeled RENP alone). A level of binding of detectably labeled RENP in the test sample which is lower than binding of detectably labeled RENP in the negative control sample is indicative of the presence of LPS in the sample.

In an alternative embodiment, the competition binding assay is performed with support-bound RENP. In this latter assay, detectably labeled LPS (e.g., radiolabeled LPS) is mixed with the test sample suspected of containing LPS, and the samples contacted with the support-bound RENP, and the amount of detectably labeled LPS bound to the support bound RENP detected. A level of detectably labeled LPS bound to the support in the test sample which is significantly lower than the amount of detectably labeled LPS in the negative control sample (radiolabeled LPS alone) is indicative of the presence of LPS in the test sample.

As is apparent from the description above, the in vitro LPS assays of the invention can be performed both qualitatively and quantitatively. For example, quantitative assays can be performed by comparing the results obtained with the test sample to results obtained with parallel samples containing known amounts of LPS. Quantitative in vitro assays are indicative of, for example, the severity of Gram-negative infection in a patient sample from whom the sample was obtained, or a degree of contamination where the test sample is a fluid for administration to a patient (e.g., where the assay is performed as a step in quality control). One of ordinary skill in the art will appreciate upon reading the above-described in vitro assays that numerous variations of these assays can be performed without departing from the spirit or the scope of the invention.

Detection of LPS in vivo

Detectably labeled RENPs of the invention, preferably RENPs having an increased LPS binding affinity relative to LBP, can be used as a diagnostic to identify a site of Gram-negative bacterial infection in a patient. For example, a detectably labeled RENP is administered to a patient suspected of having a Gram-negative infection. Preferably, the detectable label is a radionucleotide such as $^{123}$I, $^{124}$I, $^{125}$I, $^{129}$I, $^{131}$I, or other beta-emitting radionuclide which can be readily detected with either a hand-held gamma radiation detection device or by nuclear medicine scan. Alternatively, the detectable label is a fluorescent molecule or other visually detectable label which can be visualized during, for example, endoscopy. Detection can be facilitated by increasing the ratio of detectable label to RENP.

The detectably labeled RENP is administered to the patient in an amount sufficient for binding of the RENP to the suspected infection site and detection of the detectable label. The detectably labeled RENP can be administered by injection, preferably by either intravenous injection or by direct injection into the body cavity or tissue suspected of containing the infection site. In general, the amount of detectably labeled RENP administered will vary with according to numerous variables including the RENP and detectable label used, the location of the suspected site of infection, the route of administration, and various patient factors including size, weight, age, and suspected severity of the disease.

After administration, the detectably labeled RENP is allowed to circulate to reach the site of infection and/or incubate over the suspected site of infection. Bound detectably labeled RENP is detected using methods appropriate for the label used. For example, where the detectable label is a radionucleotide, bound RENP is detected using a radiation detecting device. Using this method, the site and the extent of a Gram-negative infection can be determined. Where desirable, the detectably labeled RENPs can be used to label a site or sites of infection which can then be imaged using any of a variety of imaging techniques known in the art (e.g., X-ray, CAT scan, MRI, or PET scan).

LPS Decontamination Using RENPs

The RENPs of the invention can also be used in the decontamination of a product prior to its medical application. For example, where a recombinant protein has been produced by expression in E. coli, a solution containing the recombinant protein can be applied to a support having bound RENP (e.g., an affinity column). LPS in the solution binds to the RENP bound to the support, and the LPS-free solution is collected. If necessary, the decontamination step can be repeated multiple times until an acceptably low amount of LPS (e.g. 0 to 0.001 ng/ml is detected in the solution. Such decontamination procedures using the RENPS of the invention can be used as a final step in quality control of, for example, recombinantly produced pharmaceuticals.

EXAMPLES

The following examples are put forth so as to provide those of ordinary skill in the art with a complete disclosure and description of how to carry out the invention and is not intended to limit the scope of what the inventors regard as their invention. Efforts have been made to ensure accuracy with respect to numbers used (e.g., amounts, temperatures, etc.), but some experimental error and deviation should be accounted for. Unless indicated otherwise, parts are parts by weight, molecular weight is weight average molecular weight, temperature is in degrees Centigrade, and pressure is at or near atmospheric.

Example 1: Construction of RENPs

Specific examples of RENPs are described in Table 3, and are additionally designated by a construct name (e.g., NCY103) or lot number of the protein stock.

TABLE 3

Examples of RENPs

| SEQUENCE | CONSTRUCT NAME OR LOT # | DESCRIPTION |
|---|---|---|
| BPI | NCY101 | Native sequence |
| $L_{1-197(132 \to V)}B_{200-456(N206 \to D)}$ | NCY103 | LBP-BPI chimera |
| $B_{1-199}L_{200-456}$ | NCY104 | BPI-LBP chimera |
| $B_{(S351 \to A)}$ | NCY105 | Glycosylation site deleted |
| $B_{(S8200 \to DP)}$ | NCY106 | Formic acid cleavage site |

TABLE 3-continued

Examples of RENPs

| SEQUENCE | CONSTRUCT NAME OR LOT # | DESCRIPTION |
|---|---|---|
| $L_{1-199}B_{200-456(8351\rightarrow A)}$ | NCY107 | inserted LBP-BPI chimera with glycosylation site deleted |
| $B_{1-199}$ | NCY108 | N-terminal domain of BPI |
| $B_{(1-190)}$ | Lot #159699 | N-terminal BPI fragment |
| $B_{(1-236)}$ | Lot #159695 | N-terminal BPI fragment |
| $B_{(1-212)}$ | Lot #159693 | N-terminal BPI fragment |
| $B_{1-199}Fc$ | NCY110 | N-terminal BPI-IgG chimera |
| $B_{200-456}$ | NCY112 | C-terminal fragment of BPI |
| $L_{1-59}B_{60-456}$ | NCY114 | LBP-BPI chimera |
| $L_{1-134}B_{135-456}$ | NCY115 | LBP-BPI chimera |
| $L_{1-275}B_{278-456}$ | NCY116 | LBP-BPI chimera |
| $L_{1-359}B_{360-456}$ | NCY117 | LBP-BPI chimera |
| $L_{(1-164)}B_{(200-456)}$ | Lot #164325 | LBP-BPI chimera |
| $L_{(1-175)}B_{(200-456)}$ | Lot #164326 | LBP-BPI chimera |
| $L_{1-197}B_{200-456}$ | NCY118 | LBP-BPI chimera |
| $B_{(F61\rightarrow C)}$ | NCY119 | Cysteine insertion |
| $B_{(C132\rightarrow A)}$ | NCY120 | Cysteine substitution |
| $B_{(C132\rightarrow S)}$ | NCY121 | Cysteine substitution |
| $B_{(C135\rightarrow S)}$ | NCY122 | Cysteine substitution |
| $B_{(C175\rightarrow S)}$ | NCY123 | Cysteine substitution |
| $B_{(C132\rightarrow A)(C135\rightarrow S)(C175\rightarrow S)}$ | NCY124 | Multiple cysteine substitution |
| $B_{(1-132\rightarrow A)(C135\rightarrow S)(C175\rightarrow S)}$ | NCY125 | Multiple cysteine substitution |
| $L_{(1-134)}B_{(136-361)}L_{(360-456)}$ | NCY133 | LBP-BPI chimera |
| $L_{(1-134)}B_{(136-275)}L_{(274-456)}$ | NCY134 | LBP-BPI chimera |
| $L_{(1-198)}B_{(202-275)}L_{(274-456)}$ | NCY135 | LBP-BPI chimera |
| $L_{(1-198)}B_{(202-361)}L_{(360-456)}$ | NCY136 | LBP-BPI chimera |
| $B_{(1-41)}L_{(42-199)}B_{(200-456)}$ | Lot #162303 | BPI-LBP-BPI chimera |
| $B_{(1-190)(C173\rightarrow A)}$ | Lot #162305 | N-terminal BPI fragment with cationic substitution |
| $B_{(K27\rightarrow S)(K30\rightarrow L)(K33\rightarrow T)(K42\rightarrow R)(K44\rightarrow P)(K48\rightarrow R)(R59\rightarrow H)}$ ($B_{CAT7}$) | NCY137 | Cationic Substit. (7) |
| $B_{(K77\rightarrow S)(K86\rightarrow R)(K90\rightarrow R)(R96\rightarrow S)(K118\rightarrow L)(K127\rightarrow R)}$ ($B_{CAT6}$) | NCY138 | Cationic Substit. (6) |
| $B_{(K148\rightarrow G)(K150\rightarrow D)(K160\rightarrow N)(K161\rightarrow Q)(R167\rightarrow Q)(K169\rightarrow V)(K177\rightarrow M)(K185\rightarrow D)(K198\rightarrow E)}$ ($B_{CAT9}$) | NCY139 | Cationic Substit. (9) |
| $B_{(K77\rightarrow S)(K86\rightarrow R)(K90\rightarrow R)(K96\rightarrow S)(K118\rightarrow L)(K127\rightarrow R)(K148\rightarrow G)(K150\rightarrow D)(K160\rightarrow N)(K161\rightarrow Q)(R167\rightarrow Q)(K169\rightarrow V)(K177\rightarrow M)(K185\rightarrow D)(K198\rightarrow E)}$ ($B_{CAT15}$) | NCY140 | Cationic Substit. (15) |
| $L_{(S77\rightarrow K)(R86\rightarrow K)(R90\rightarrow K)(S96\rightarrow K)(L118\rightarrow K)(R126\rightarrow K)}$ ($L_{CAT6}$) | NCY141 | Cationic Repl. (6) |
| $L_{(G147\rightarrow K)(D148\rightarrow K)(N158\rightarrow K)(Q159\rightarrow K)(Q165\rightarrow R)(V167\rightarrow K)(M175\rightarrow K)(D183\rightarrow K)(E196\rightarrow K)}$ ($L_{CAT9}$) | NCY142 | Cationic Repl. (9) |
| $L_{(S77\rightarrow K)(R86\rightarrow K)(R90-K)(S96\rightarrow K)(L118\rightarrow K)(R126\rightarrow K)(G147\rightarrow K)(D148\rightarrow K)(N158\rightarrow K)(Q159\rightarrow K)(Q165\rightarrow R)(V167\rightarrow K)(M175\rightarrow K)(D183\rightarrow K)(E196\rightarrow K)}$ ($L_{CAT15}$) | NCY143 | Cationic Repl. (15) |
| $L_{(1-198)}B_{(201-456)}Fc$ | NCY144 | LBP-BPI-IgG chimera |
| LBP | NCY102 | native sequence |
| $L_{1-199}$ | NCY109 | N-terminal LBP fragment |
| $L_{1-199}Fc$ | NCY111 | LBP-1g chimera |
| $L_{200-458}$ | NCY113 | C-terminal LBP fragment |
| $L_{(A132\rightarrow C)}$ | NCY126 | Cysteine insertion |
| $L_{(C61\rightarrow F)}$ | NCY127 | Cysteine substitution |
| $L_{(C61\rightarrow S)}$ | NCY128 | Cysteine substitution |
| $L_{(C135\rightarrow S)}$ | NCY129 | Cysteine substitution |
| $L_{(175\rightarrow S)}$ | NCY130 | Cysteine substitution |
| $L_{(C61\rightarrow F)(C135\rightarrow S)(C175\rightarrow S)}$ | NCY131 | Multiple cysteine substitution |
| $L_{(C61\rightarrow S)(C135\rightarrow S)(C175\rightarrow S)}$ | NCY132 | Multiple cysteine substitution |

The proteins encoded by the LBP and $L_{1-359}B_{360-456}$ constructs facilitated the LPS-mediated cellular response, indicating that LBP amino acid residues 275-359 are required for this LBP activity.

The cDNA sequences of BPI and LBP are shown in FIGS. 3A–3D and 4A–C, respectively, with each nucleotide designated numerically. DNA encoding the RENPs can be prepared using a variety of techniques well known in the art, including protein fusion techniques, site-directed mutagenesis, and PCR (see, for example, Sambrook et al., supra; Zoller, M. J., et al., Methods Enzymol. 154:329 (1987)). For example, in the construction of the RENP $L_{1-197}B_{200-456}$, the sequence "$ATAGAT_{723}$" and "$ATTGAC_{700}$" was chosen as a convenient site to insert a ClaI restriction site (ATCGAT) by which to recombine portions of both BPI (former) and LBP (latter). Oligonucleotide primers were designed which overlap this region but contain the ClaI sequence, and were synthesized on an ABI 380B synthesizer (Applied Biosystems Inc., Foster City, CA). Additional primers were designed to bind to the 5' and 3'- ends of both molecules, which primers contained NheI (5') and XhoI (3') restriction sites for insertion into the vector. These primers were used to amplify portions of the cDNA molecules encoding amino acid residues 1-199 (A) and 200-456 (B) of LBP and BPI by cyclic DNA amplification. The resulting DNA fragments were digested with the appropriate restriction enzymes and then purified by gel electrophoresis.

Example 2: Mammalian Expression

In order to produce BPI, LBP, or RENPs of the invention in mammalian cells, the cDNA sequences were inserted into a suitable plasmid vector. A suitable vector for such an application is pSE, which contains the origin of replication and early and late promoters of SV40, followed by multiple insert cloning sites, followed by the termination sequences from the hepatitis B surface antigen gene. An origin of bacterial DNA replication, and the genes encoding ampicillin resistance and dihydrofolate reductase were also included in the plasmid for production of large amounts of DNA using bacterial host cells. Similar vectors have been used to express other foreign genes (Simonsen et al., *Biologicals* 22:85 (1994). Another suitable vector, particularly for rapidly obtaining small quantities of RENPs was pCIP4 (Invitrogen Corp., San Diego, Calif.). pCEP4 contains a CMV promoter, followed by multiple insert cloning sites, followed by SV40 termination sequences. Also contained within the plasmid are an origin of bacterial DNA replication, and the genes encoding resistance to ampicillin and hygromycin B. With pCEP4 and pSE, the same insert cloning sites as pSE for easy insert shuttling between the vectors were used. Once introduced into mammalian cell hosts, this specialized plasmid replicates as an episome, allowing semistable amplification of introduced DNA sequences. The high gene copy number is maintained through the selective pressure of culture in the presence of hygromycin B.

A second expression system (EBV/293) was used to rapidly obtain small quantities of recombinant proteins of the subject invention when useful. This system was constructed to use the same insert cloning sites as pSE for easy insert shuttling, but utilized the Epstein-Barr virus promoter (EBV) to drive heterologous expression (pCEP4). Once introduced into mammalian cell hosts, this specialized plasmid replicates as an episome, allowing semistable amplification of introduced DNA sequences. The high gene copy number is maintained through the selective pressure of culture in the presence of hygromycin plus G418. Similar expression systems are commercially available (e.g., Invitrogen, Inc., San Diego, Calif.).

Vector DNA was prepared for acceptance of BPI CDNA by digestion with Nhe I and Xho I, and was subsequently dephosphorylated by treatment with alkaline phosphatase. The prepared fragments encoding BPI, LBP, or an RENP were ligated into pSE or pCEP4, and the resulting recombinant colonies were screened by agarose gel electrophoresis. Subsequently, the DNA sequences were confirmed by standard enzymatic sequencing methods (e.g., Sanger, 1974).

Expression plasmid DNA purified by either CsCl gradients with Plasmid or Midi Kits (Qiagen, Chatsworth, Calif.) was used to transform Chinese hamster ovary strain DUXB11 (pSE) and 293-EBNA cells (Invitrogen Corp., San Diego, Calif.) (pCEP4). Transfection was performed using lipofectin (Bethesda, Research Labs, Gaithersberg, Md.) by standard methods. The resulting transformed cells were selected in GHT minus medium (DUKXB11s) or in REM and 10% calf serum (293s). For the DUKXBlls, clones were selected and were passed through sequential rounds of culture in increasing concentrations of methotrexate in order to amplify the DHFR gene and associated heterologous genes. Supernatants from transfected cells, either mixed populations or clones derived from the mixed population, were assayed for RENPs by ELISA using antibodies specific for BPI, LBP, or immunoglobulin as appropriate.

Example 3: Yeast Expression

BPI and $L_{1-197}B_{200-456}$ were successfully expressed in the methylotrophic yeast Pichia pastoris. Pichia was chosen as a suitable expression system for BPI and RENPs due to its lack of LPS (endotoxin to which BPI and RENPs bind) and its ability to produce high levels of mammalian proteins.

Figure 18:
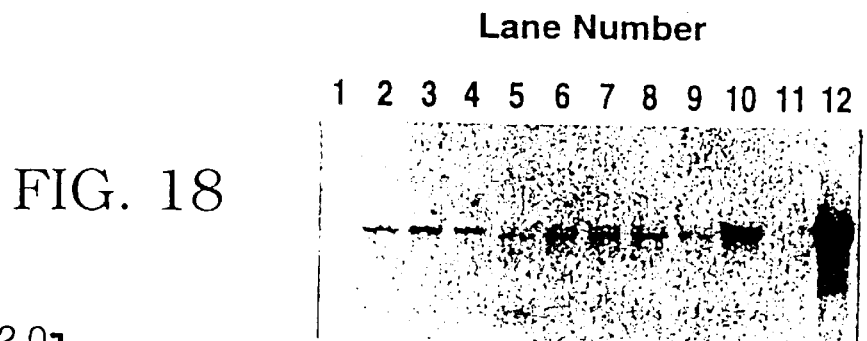
FIG. 18 is Western blot of BPI and $L_{1-197}B_{200-456}$ (NCY118) produced in Pichia pastoris.

Pichia pastoris strain GS115 (Invitrogen, San Diego, Calif.) was transformed with plasmids encoding BPI and $L_{1-197}B_{200-456}$, and transformed colonies were selected according to the procedures outlined by Invitrogen (A Manual of Methods for Expression of Recombinant Proteins in *Pichia pastoris*, Version 1.5, Invitrogen, San Diego, Calif.). For both BPI and $L_{1-197}B_{200-456}$, protein was secreted into the medium in a small-scale batch fermentation run. 116 ng/ml were secreted for the one BPI construct assayed, and 14, 11, and 10 ng/ml were secreted for the three constructs $L_{1-197}B_{200-456}$ constructs assayed. Secretion was assayed by enzyme-linked immunosorbant analysis (ELISA). The majority of protein for both constructs was not secreted, as shown by Western blot analysis with a polyclonal anti-BPI antibody (INVN 1-2) (prepared by conventional techniques by injecting rabbit with BPI) and alkaline phosphatase-conjugated goat anti-rabbit antibody. The Western blot is shown in FIG. 18.

Purified BPI from Chinese Hamster ovary cells (CHOs) was used as a positive control (lane 12). In lane 1 a sample from untransformed GS115 cells served as a negative control. The antibodies did not recognize any proteins from the untransformed GS115 cells. The next three lanes (2–4) were samples from colonies transformed with the construct for BPI and the last 6 lanes (5–10) were samples from colonies transformed with the construct for $L_{1-197}B_{200-456}$. The amount of intracellular BPI or $L_{1-197}B_{200-456}$ expressed in the batch fermentation run, based on the amount of standard BPI loaded, was roughly 100 µg/ml of medium for the BPI and $L_{1-197}B_{200-456}$ colonies.

Example 4: Protein Purification

BPI was purified from conditioned media using the following four-step purification. BPI was captured on CM Sepharose (Pharmacia LKB Biotechnology). The column was washed in 50 mM Tris pH 7.4, and protein was eluted with 50 mM Tris buffer pH 7.4+1 M NaCl. The eluate was diluted 10× with 50 mM Tris pH 8.5, run over Fast Q Sepharose, and the flow-through was collected. BPI was re-captured on CM Sepharose and again eluted as before. Buffer exchange into 10 mM Succinate +110 mM NaCl pH 6 was performed using Sepharose CL6B (Pharmacia LKB Biotechnology). Finally, Tween 20 was added to the formulated material to a final concentration of 0.05%.

LBP (NCY102) was captured from cell culture medium on Fast S Sepharose (Pharmacia). The column was washed with 50 mM Tris pH 7.4, and protein was eluted using 50 mM Tris pH 7.4+1 M NaCl. The eluate was diluted 10× in 50 mM Tris pH 8.5 and run over HiLoad Q Sepharose (Pharmacia). Protein was eluted with a 0-1 M NaCl gradient in 50 mM Tris pH 8.5. Appropriate fractions were pooled according to migration on SDS PAGE electrophoresis. LBP concentration was diluted to 4.0 mg/ml, and the pH was adjusted to 7.0 with 100 mM HCl.

$L_{1-197(I43->V)}B_{200-456(N206->D)}$ was purified from cell culture medium using the same method described for LBP.

$B_{1-199}L_{200-456}$ and $B_{(S351->A)}$ were purified using the same protocol as for BPI, except that the size exclusion step was omitted.

$L_{1-59}B_{60-456}$, $L_{1-134}B_{135-456}$ and $B_{CAT6}$ were captured on a Poros II HS cation exchange column (PerSeptive Biosystems, Cambridge, Mass.) at pH 7.4. The column was washed with 20 mM HEPES buffer at pH 7.5, and eluted with 20 mM HEPES pH 7.5 with 1 M NaCl. The eluate was diluted 5× in 20 mM HEPES pH 7.5 and applied to a Poros HQ anion exchange column (PerSeptive) with the flow-through applied directly to a POROS II HS column. The POROS II HS column was eluted with 3.3 mM acetate, 3.3 mM MES and 3.3 mM HEPES, pH 6.0 with a 0–1 M NaCl gradient.

$L_{1-359}B_{360-456}$ and $L_{(1-198)}B_{(201-456)}Fc$ were captured from conditioned medium at pH 7.4 on a Poros II HS column. The column was washed with 20 mM HEPES buffer at pH 7.5, and eluted with 20 mM HEPES pH 7.5+1 M NaCl. The eluate was diluted 10× with 20 nM HEPES pH 7.5, loaded on a second, smaller Poros II HS column, and eluted with 3.3 mM acetate, 3.3 mM MES and 3.3 mM HEPES, pH 6 with a 0–1 M NaCl gradient.

Example 5: BPI Activity Against *N. meninaitidis* and *N. gonorrhoeae*

BPI suppresses TNF release by human inflammatory cells in response to lipopolysaccharide (LPS) derived from a wide range of Gram-negative bacterial species. In order to test the activity of BPI against Gram-negative lipooligosaccharide (LOS) from the pathogenic bacteria *Neisseria meningitidis* and *N. gonorrhoeae*, non-viable bacteria were pre-treated with recombinant BPI and incubated with human whole blood for 4 hours at 37° C. Without BPI, *N. meningitidis* at 105 bacteria/ml stimulated the release of 2.93±0.53 ng/ml of TNF, while *N. gonorrhoeae* was a more potent stimulator of TNF release: $10_4$ bacteria/ml induced 8.23±0.32 ng/ml of TNF. In both cases, 10 μg/ml BPI completely inhibited TNF release. This indicates that BPI is able to bind and detoxify LOS of these organisms, as well as bind LPS. Thus, BPI can be useful as a therapeutic agent against LOS-mediated tissue damage associated with these pathogenic Neisseria species.

Example 6: $^{biotinylated}$BPI Binding Competition Assays

Competition assays for binding of LPS immobilized on microtiter plates was performed using a modified procedure described by Tobias et al., *J. Biol. Chem.* 264:10867 (1989). Briefly, Immulon 3 microtiter plates (96-well, Dynatech Biotechnology Products, Chantilly, Va.) were coated with 1 or 4 μg of *S. minnesota* R595 Re LPS (LIST Biological Labs, Inc., #304) in 50 mM borate pH 9.5-9.8+20-25 mM EDTA overnight at 37° C. Blank, non-LPS coated wells were included on each plate and binding to these wells was used to determine non-specific binding. Absorbance values from wells which were not pre-coated with LPS consistently gave optical density readings of less than 0.05. Plates were then washed extensively under running distilled deionized water, then dried at 37° C. Assay wells were blocked for 60 minutes at 37° C. with 1–2% very low endotoxin BSA (Sigma, St. Louis, Mo.) prepared in pyrogen-free Tris-buffered saline (50 mM Tris pH 7.4+150 mM NaCl). The wells were emptied, and biotinylated BPI was incubated in the presence or absence of unlabeled BPI or recombinant protein of the subject invention diluted in assay buffer (pyrogen-free TBS +1 mg/ml low endotoxin BSA, and 0.05% Tween-20) was. incubated in the LPS coated and uncoated wells for 2–3 hours at 37° C. in a total volume of 100 μl/well. After four washes in assay buffer, plates were developed with streptavidin conjugated to alkaline phosphatase (BioRad, Burlingame, Calif.) followed by 100 μl of PNP substrate solution (Sigma) freshly prepared from two 5 mg tablets dissolved in 10 ml substrate buffer. Substrate buffer is prepared with 24.5 mg MgCl2, 48 ml diethanolamine, brought up to 400 ml, pH adjusted to 9.8 and volume brought up to 500 ml. Absorbances were read at 405 nm on a Vmax kinetic microplate reader (Molecular Devices, Inc., Menlo Park, Calif.).

Figure 7:
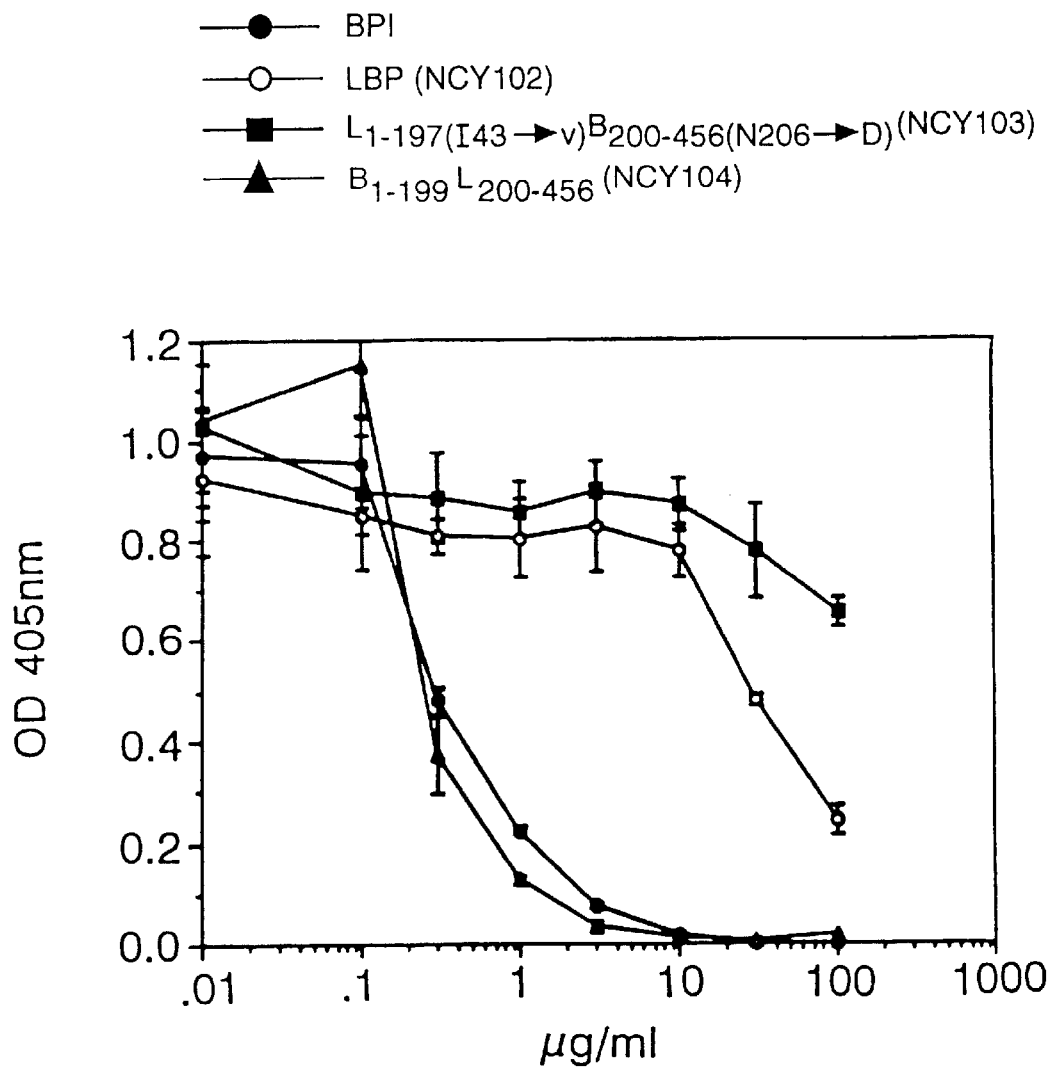
FIG. 7 is a graph showing the effects of BPI, LBP, $L_{1-197(I43->V)}B_{200-456(N206->D)}$ (NCY103) and $B_{1-199}L_{200-456}$ (NCY104) on $^{biotinylated}$ BPI binding to LPS.

The relative LPS binding affinities of BPI, LBP and RENPs were tested in the competitive binding assay described above using 10 ng/ml $^{biotinylated}$BPI. In these experiments, BPI inhibited bIoy BPI binding to LPS in a concentration-dependent manner (FIG. 7). Modest inhibition of $^{biotinylated}$BPI-binding was observed using NCY102 (LBP) and $L_{1-197(I43->V)}B_{200-456(N206->D)}$, suggesting that BPI has either a higher affinity for LPS bound to a surface or that LBP and $L_{1-197(I43->V)}B_{200-456(N206->D)}$ bind to a different site on LPS. $B_{1-199}L_{200-456}$, which contains the N-terminal domain of BPI, competed with $^{biotinylated}$BPI at similar concentrations as unlabeled BPI, suggesting a similar affinity and binding site.

Figure 13B:
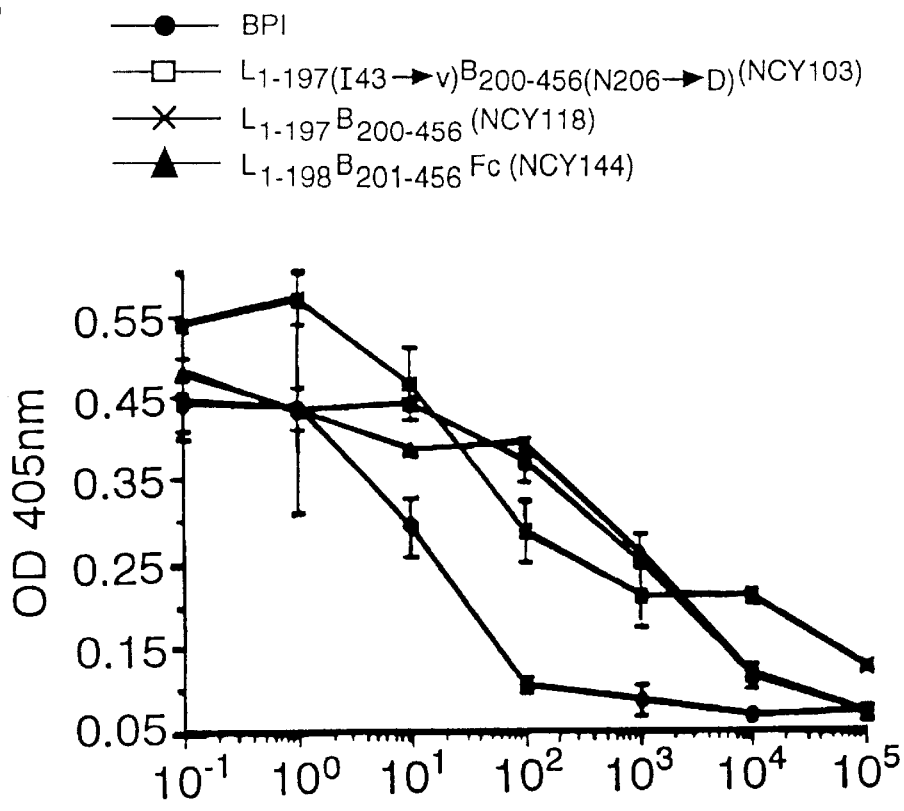
FIGS. 13A–13C are graphs showing the effects of BPI, $L_{1-197(I43->V)}B_{200-456(N206->D)}$ (NCY103), $L_{1-197}B_{200-456}$ (NCY118), $L_{1-198}B_{201-456}Fc$ (NCY144), $L_{1-59}B_{60-456}$ (NCY114), $L_{1-134}B_{135-456}$ (NCY115), $L_{1-359}B_{360-456}$ (NCY117), and $B_{CAT9}$ (NCY139) on biotinylated BPI binding to LPS.
Figure 13A:
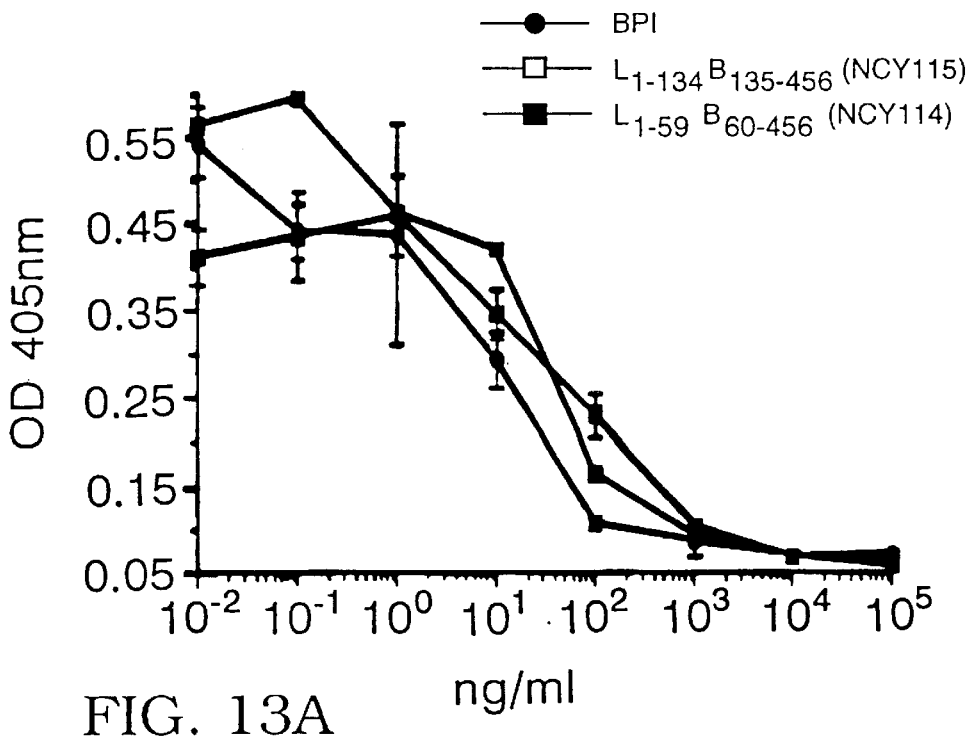

Competition between either $L_{1-197}B_{200-456}$ (NCY118) or $L_{1-197(I43->V)}B_{200-456(N206->D)}$ with biotinylated BPI occurred at similar concentrations, giving overlapping curves (FIG. 13A) indicating that the two amino acid differences between these two molecules [$L_{1-197}B_{200-456}$-> $L_{1-197(I43->V)}B_{200-456(N206->D)}$: (I43->V) and (N206->D)] had no effect on affinity for immobilized LPS. $L_{(1-198)}$ $B_{(201-456)}Fc$ (an IgG chimera consisting of $L_{1-197}B_{200-456}$ linked to human IgG1 Fc constant region of the immunoglobulin molecule) does not have an altered ability to compete with biotinylated BPI (FIG. 13A). $L_{1-59}B_{60-456}$ and $L_{1-134}B_{135-456}$ showed a similar affinity for LPS which affinity was very similar to that observed for BPI, suggesting that the region between amino acid residues 1-59 (or 1-134) probably plays a minimal role in LPS binding (FIG. 13B). Together with data showing the $B_{1-199}L_{200-456}$ competes effectively with BPI (FIG. 7), these results indicate that amino acid residues 134-199 are important structural components of the high-affinity LPS-binding domain of BPI.

Figure 13C:
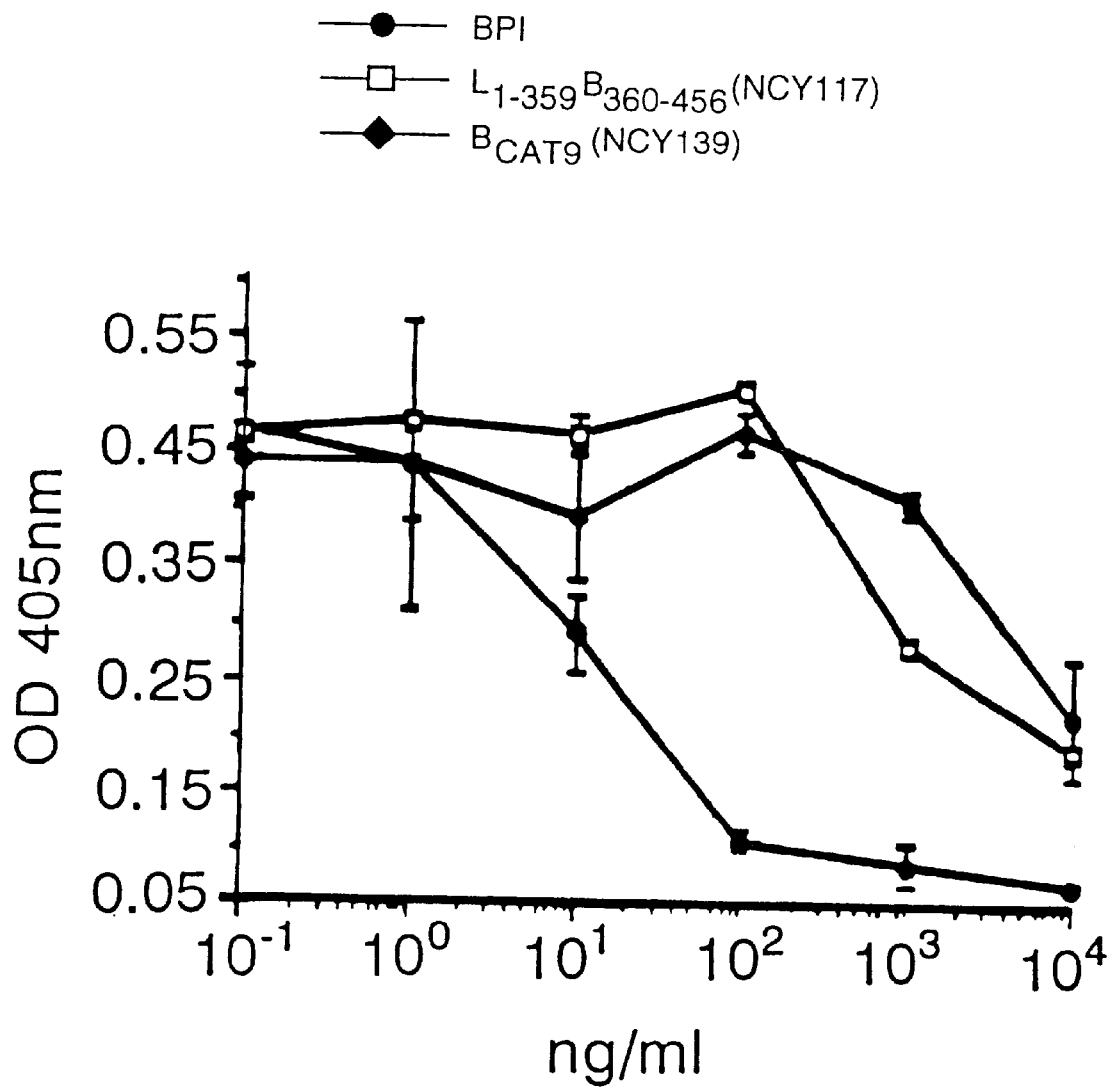

The importance of the region between amino acid residues 134 to 197 in LPS affinity was further demonstrated by the markedly reduced affinity of $B_{CAT9}$, a mutant in which all of the cationic amino acids of the BPI molecule (particularly the cationic residues of BPI amino acids 134-200) are replaced with the corresponding amino acid residues found in LBP. These changes resulted in a molecule with binding affinity for LPS which was more similar to that of LBP than BPI (FIG. 13C, and FIG. 7). Amino acid residues 360 to 456 of BPI are apparently not involved in LPS binding as demonstrated by the relative inability of $L_{1-359}B_{360-456}$ to displace biotinylated BPI from LPS (FIG. 13C). The apparent binding affinity of $L_{1-359}B_{360-456}$ for LPS is similar to that of LBP and $B_{CAT9}$, which affinity is approximately two orders of magnitude lower than the apparent affinity of BPI for LPS.

Thus, the domain of BPI which participates in binding to immobilized LPS is localized in the N-terminal half of the BPI molecule, since $B_{1-199}L_{200-456}$ has the greatest ability to displace native BPI from LPS coated onto microtiter plates. This domain of BPI has been more specifically localized to a region between amino acid residues 134-199.

Example 7: Chromogenic LAL Assay

Figure 8:
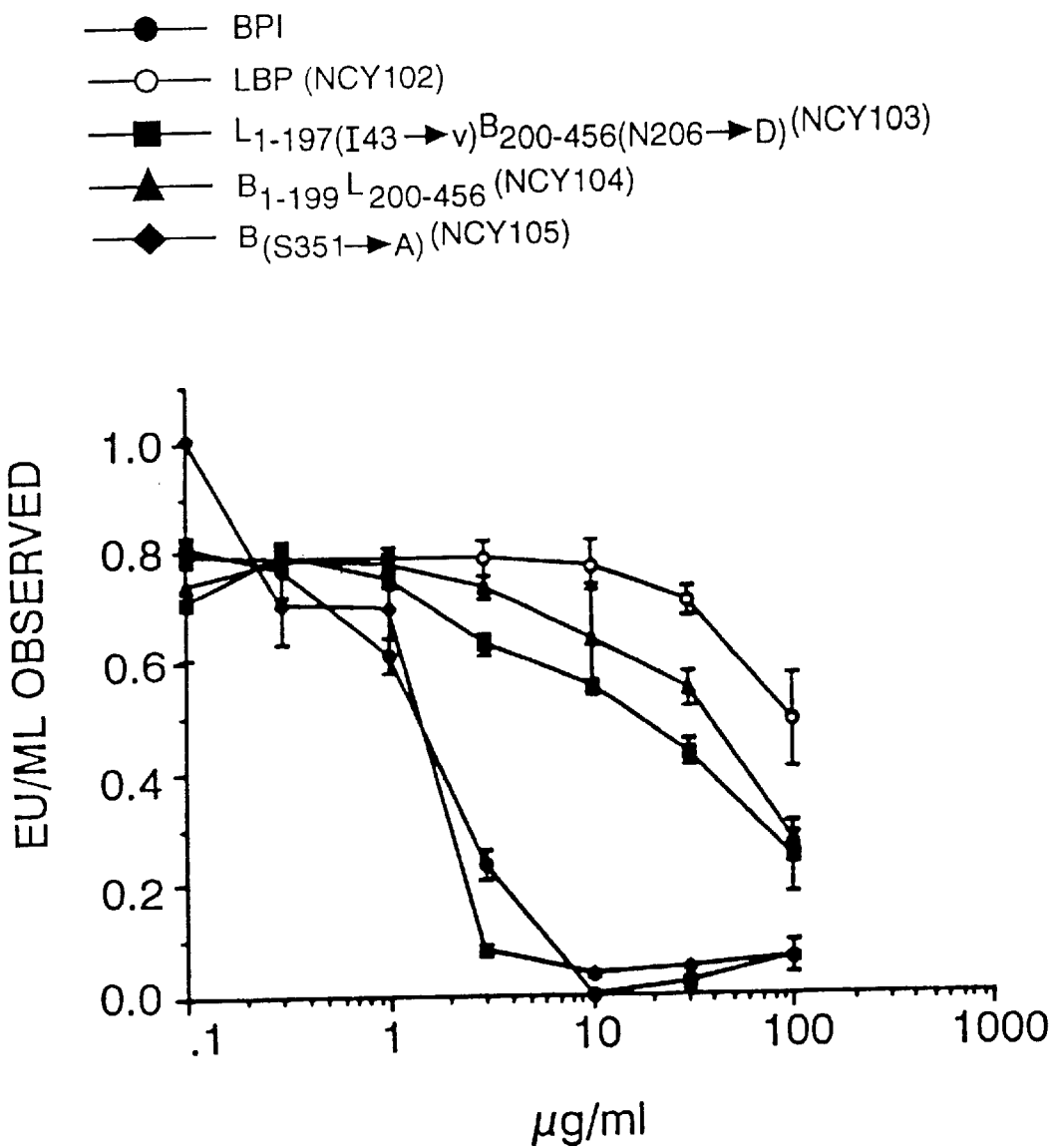
FIG. 8 is graph showing the effects of BPI, LBP, $L_{1-197(I43->V)}B_{200-456(N206->D)}$ (NCY103), $B_{1-199}L_{200-456}$ (NCY104), or $B_{(S351->A)}$ (NCY105) protein on LPS activity in the chromogenic LAL assay.

To test the relative abilities of BPI, LBP and RENPs to neutralize LPS in vitro, these proteins were tested for inhibitory activity in the chromogenic LAL assay. Briefly, BPI and RENPs (25 µl of 0–200 µg/ml) were pre-incubated for 1 hour at 37° C. with 1 EU/ml of *E. coli* 0111:B4 LPS, (Whitaker Biologicals, Walkersville, Md.). The mixtures were then tested for LAL activity using the chromogenic LAL assay kit (Whitaker Biologicals, Walkersville, Md). The results are shown in FIG. 8 and Table 4. LPS was neutralized by the various proteins tested in the order of: $B_{(S351->A)} \geq BPI > L_{1-197(I43->V)}B_{200-456(N206->D)} > B_{1-199}$ $L_{200-456} > LBP$. Several studies were carried out with different lots of each protein and the $IC_{50}$ values were determined. The averaged $IC_{50}$ values are shown in Table 4.

TABLE 4

LPS Inhibition in the Chromogenic LAL Assay

| Product | $IC_{50}$ (µg/ml) | No. of test |
|---|---|---|
| $B_{(S351->A)}$ | 1.5 | (n = 1) |
| BPI | 5.2 ± 3.3 | (n = 10) |
| $L_{1-197(I43->V)}B_{200-456(N206->D)}$ | 28.0 ± 20.0 | (n = 4) |
| $B_{1-199}L_{200-456}$ | 40.0 | (n = 1) |
| LBP | 65.0 ± 31.0 | (n = 4) |

These results demonstrate that BPI neutralizes LPS activity in the LAL assay at lower concentrations than LBP. $B_{1-199}L_{200-456}$, which contains the N-terminal domain of BPI, effectively competes with BPI for binding to LPS (see FIG. 7) but is a relatively poor inhibitor of LPS in the LAL assay. These results indicate that the N-terminal (LPS-binding) domain of BPI alone does not account for the neutralizing activity of BPI in the LAL assay. $L_{1-197(I43->V)}$ $B_{200-456(N206->D)}$ was a more potent inhibitor than LBP or $B_{1-199}L_{200-456}$, suggesting that the C-terminal domain of BPI plays a very important role in endotoxin neutralization in the LAL assay.

Additional results of LPS neutralizing activity in the chromogenic LAL assay are shown in Table 5. $L_{1-197(I43->V)}B_{200-456(N206->D)}$, $L_{1-59}B_{60-456}$, and $L_{1-134}$ $B_{135-456}$ share the C-terminal half of the BPI molecule, again indicating that this domain plays an important role in LPS-neutralizing activity. Also, these data indicate that the 199-456 region is most important in LPS neutralization since adding BPI amino acid residues between 136-456 or 60-456 did not improve LPS neutralizing activity. Together with the LPS binding data, these results further indicate that the C-terminal half of BPI is important for neutralization, while the N-terminal sequence is more critical for LPS binding.

TABLE 5

LPS Inhibition in the Chromogenic LAL Assay

| Protein | | IC50 | n |
|---|---|---|---|
| BPI | Cumulative | 1.58 ± 1.58 | 94 |
| | Lot# 149718 | 1.57 ± 1.01 | 54 |
| | Lot# 149719 | 1.69 ± 0.35 | 7 |
| | Lot# 149722 | 1.70 ± 0.28 | 2 |
| | Lot# 149724 | 1.41 ± 0.45 | 45 |
| | Lot# 155794 | 1.95 ± 0.92 | 2 |
| LBP | Cumulative | 55.92 ± 30.53 | 8 |
| | Lot# 151281 | 34.33 ± 7.45 | 6 |
| | Lot# 151204 | 77.50 ± 24.45 | 2 |
| $L_{1-197(143->V)}B_{200-456(N206->D)}$ | Cumulative | 22.86 ± 16.28 | 54 |
| | Lot# 151235 | 25.50 ± 0.71 | 2 |
| | Lot# 151242 | 36.50 ± 2.12 | 2 |
| | Lot# 151274 | 3.46 ± 2.18 | 38 |
| | Lot# 159616 | 8.83 ± 4.91 | 4 |
| $B_{1-199}L_{200-456}$ | Cumulative | 24.19 ± 6.42 | 9 |
| | Lot# 151246 | 12.50 ± 0.26 | 3 |
| | Lot# 152658 | 10.70 | 1 |
| | Lot# 155737 | 40.18 ± 34.48 | 4 |
| $B_{1-199}$ | Cumulative | 5.52 ± 5.05 | 17 |
| | Lot# 151285 | 1.12 ± 0.00 | 2 |
| | Lot# 155709 | 9.73 ± 1.18 | 3 |
| | Lot# 155779 | 2.13 ± 0.81 | 2 |
| $L_{1-59}B_{60-456}$ | Lot# 155754 | 3.64 ± 1.64 | 5 |
| $L_{1-134}B_{135-456}$ | Lot# 155756 | 5.02 ± 3.11 | 5 |
| $L_{1-275}B_{278-456}$ | Lot# 155791 | 14.00 ± 2.65 | 3 |
| $L_{1-359}B_{360-456}$ | Lot# 155733 | >100 | 4 |
| $L_{1-197}B_{200-456}$ | Cumulative | 12.75 ± 3.54 | 12 |
| | Lot# 155758 | 10.25 ± 30.9 | 8 |
| | Lot# 159619 | 15.25 ± 5.91 | 4 |
| $B_{CAT6}$ | Lot# 155785 | 1.97 ± 0.06 | 3 |
| $B_{CAT9}$ | Lot# 155762 | 29.60 ± 23.23 | 5 |
| $B_{CAT15}$ | Lot# 155788 | 7.87 ± 2.80 | 3 |
| $L_{(1-198)}B_{(202-275)}L_{(274-456)}$ | Lot# 159649 | >100 | 3 |
| $L_{(1-198)}B_{(201-456)}Fc$ | Lot# 155760 | 12.15 ± 6.00 | 4 |
| $L_{1-199}$ | | 9.2 | 1 |
| $B_{1-199}$ | | 10.2 ± 0.92 | 5 |
| $L_{(1-134)}B_{(136-275)}L_{(274-456)}$ | Lot# 159643 | 22.00 ± 15.25 | 4 |

$B_{CAT9}$, which contains the entire BPI sequence except for nine cationic residues between positions 148 and 197 showed very poor LPS-neutralizing activity, suggesting that these residues are important in LPS-neutralizing activity. Similarly, this compound was relatively ineffective at competing with native BPI for binding to LPS. These cationic residues may permit correct structural conformation of the molecule, since both $L_{1-197(I43->V)}B_{200-456(N206->D)}$ and $B_{CAT9}$ contain the C-terminal domain of BPI, yet $L_{1-197(I43->V)}B_{200-456(N206->D)}$ has potent neutralizing activity while $B_{CAT9}$ does not.

Example 8: Inhibition of FITC-labeled LPS Binding to Human Monocytes

The relative LPs-binding affinities of RENPs of the invention were investigated by examining the abilities of the RENPs to inhibit LPS binding to human peripheral blood monocytes. Blood collected in acid citrate dextrose-containing VACUTAINER™ tubes (Becton Dickinson, Rutherford, N.J.) was diluted 1:4 in Hank's balanced salt solution (HBSS) minus calcium and magnesium (Gibco BRL, Grand Island, Md.). Mononuclear cells were isolated using Ficol-Paque (Pharmacia Inc., Piscataway, N.J.). Cells were washed three times in HBSS, then brought up to an appropriate volume of RPMI 1640 with glutamine and antibiotics to give approximately $1 \times 10^6$ cells/ml. To one ml aliquots of cells, FITC-LPS was added to a final concentration of 500 ng/ml. Tubes were closed and incubated at 37° C. on a rocking platform. At the end of the incubation, cells were washed twice with PBS with 0.05% Human Serum Albumin and 0.02% sodium azide. FACS analysis of the cells was performed on a FACStar flow cytometer, Immunocytometry System, Becton Dickinson (Mountain View, Calif.). The monocyte portion of the cell population was determined by side scatter versus forward scatter gating and confirmed by staining a separate aliquot of cells with phycoerythrin-conjugated anti-DR antibody (Becton Dickinson Immunocytometry Systems, Milpitas, Calif.). Results are reported as logarithmic scale mean fluorescence intensity.

Figure 9:
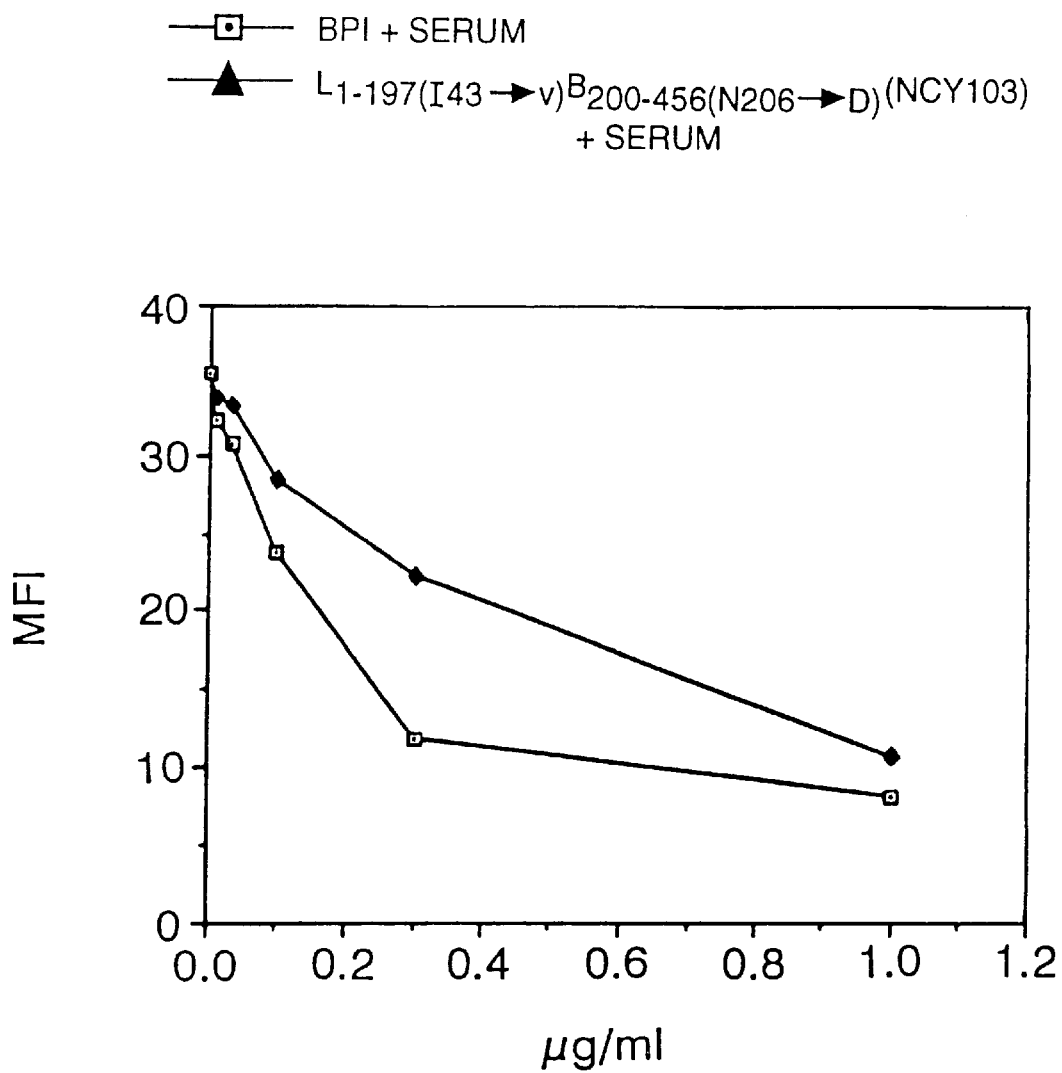
FIG. 9 is a graph showing FITC-LPS binding to monocytes in the presence of BPI or $L_{1-197(I43->V)}B_{200-456(N206->D)}$ (NCY103).

To determine the relative abilities of BPI or $L_{1-197(I43->V)}B_{200-456(N206->D)}$ to inhibit LPS binding to human peripheral blood monocytes, isolated human peripheral blood mononuclear cells were incubated with 10% human serum containing 500 ng/ml FITC-conjugated $E.\ coli$ O55:B5 LPS in the presence or absence of BPI or $L_{1-197(I43->V)}B_{200-456(N206->D)}$. Binding of FITC-LPS to monocytes could be inhibited by increasing concentrations of both BPI and $L_{1-197(I43->V)}B_{200-456(N206->D)}$ (FIG. 9). Thus $L_{1-197(I43->V)}B_{200-456(N206->D)}$ has BPI-like activity, despite the fact that $L_{1-197(I43->V)}B_{200-456(N206->D)}$ contains the N-terminal domain of LBP. These data, along with the results of the LPS neutralization studies shown in FIG. 8, suggest that the C-terminal domains of BPI and LBP, and not the N-terminal domains, determine whether the proteins inhibit or mediate LPS activation of cells.

Further studies were undertaken to determine the effects of BPI, LBP, $L_{1-197(I43->V)}B_{200-456(N206->D)}$ and $B_{1-199}L_{200-456}$ on FITC-labeled LPS binding to peripheral blood monocytes in the presence and absence of serum. In a serum-free FITC-labeled LPS binding system where no LBP is available, FITC-labeled LPS does not bind to cells. In contrast recombinant LBP facilitated LPS binding to cells at concentrations as low as 100 ng/ml. $B_{1-199}L_{200-456}$ also facilitated binding, although to a lesser extent. Neither BPI or $L_{1-197(I43->V)}B_{200-456(N206->D)}$ promoted significant binding of LPS to cells. These data indicate that the C-terminal domain of LBP is active in LPS binding to cells. The N-terminal domain of BPI may exert an inhibitory influence on LPS binding to cells mediated by the C-terminal domain of LBP because $B_{1-199}L_{200-456}$ was less active than LBP.

Figure 14A:
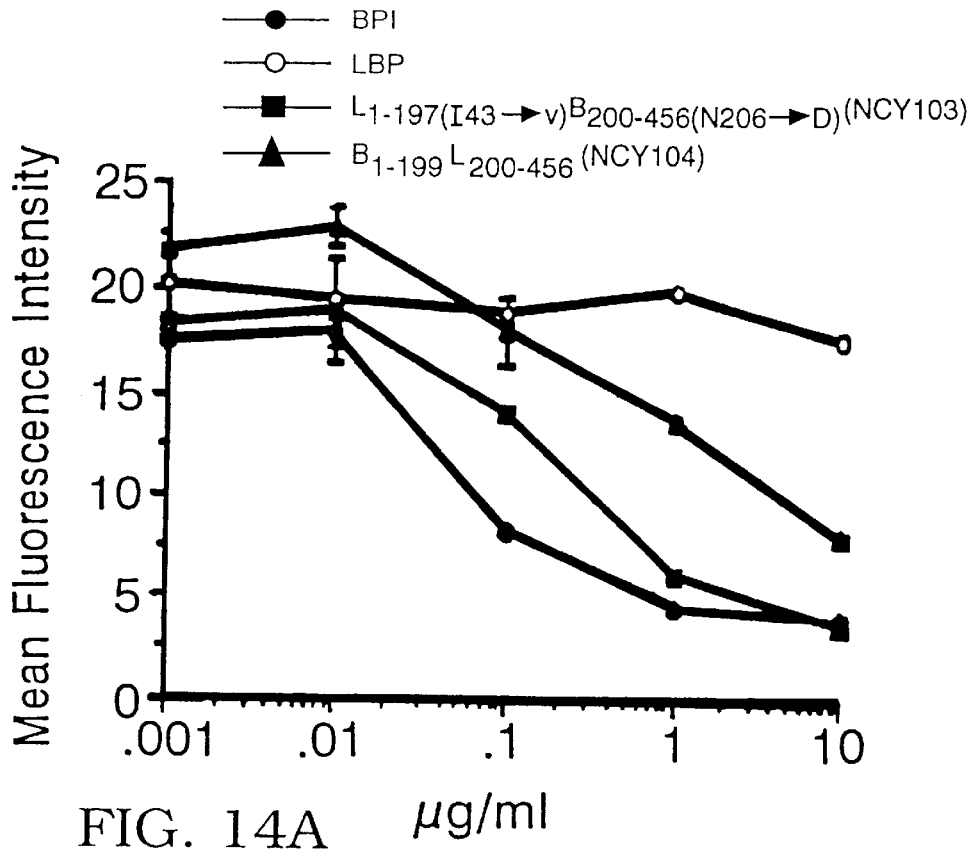
FIGS. 14A–14B are graphs showing the effects of BPI, LBP, $L_{1-197(I43->V)}B_{200-456(N206->D)}$ (NCY103) and $B_{1-199}L_{200-456}$ (NCY104) on FITC-labeled LPS binding to human peripheral blood monocytes in the presence of 10% autologous serum (14A) and in the absence of serum and presence of 0.5% human serum albumin (14B).
Figure 14B:
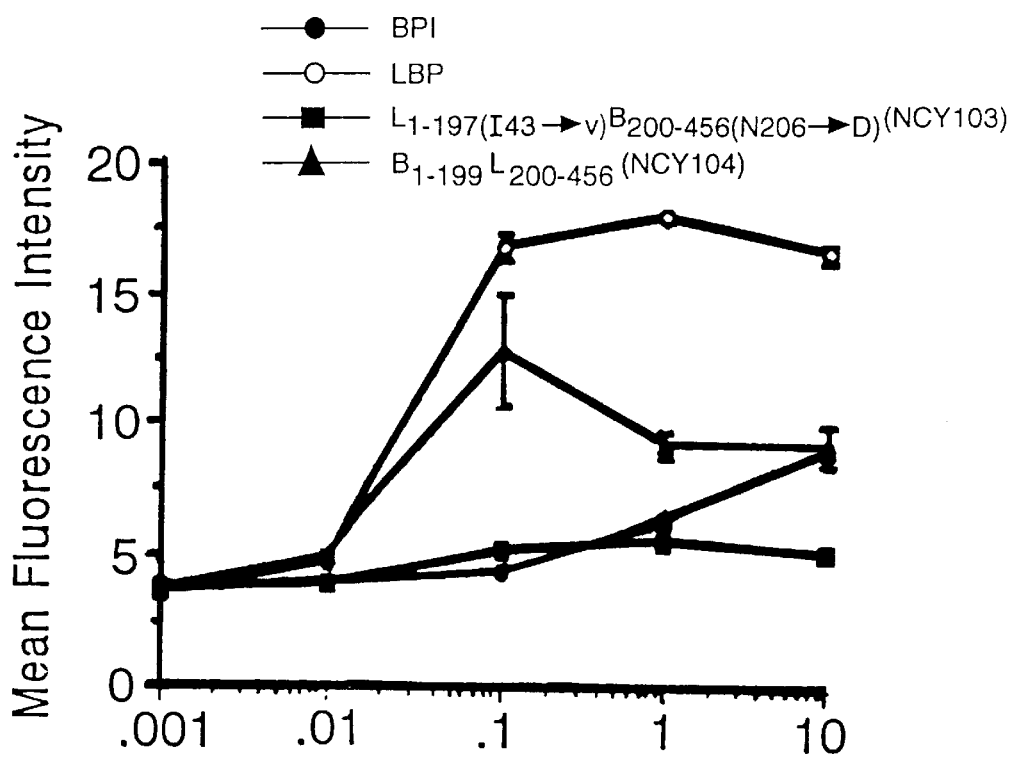

Normal human serum contains about 1-10 μg/ml LBP. In the presence of 10% autologous serum, BPI and $L_{1-197(I43->V)}B_{200-456(N206->D)}$ potently inhibited FITC LPS binding to monocytes, with BPI showing slightly greater potency. $B_{1-199}L_{200-456}$ had marginal activity, and LBP had no effect (FIG. 14A). These data indicate the importance of the BPI C-terminus in this test of LPS neutralization. $B_{1-199}L_{200-456}$ which lacks the C-terminal domain of BPI, is approximately two orders of magnitude less potent at blocking LPS binding. LBP, as expected, had no effect. Thus, BPI can intervene in the sepsis cascade by preventing LPS from binding to monocytes and causing release of TNFalpha.

Example 9: THP-1 Cell TNF Production Assay

THP-1 cells were obtained from the American Tissue Culture Collection (Rockville, Md.) and were maintained in REM medium containing 10% fetal bovine serum, 2 mM L-glutamine, 100 units penicillin and 100 μg/ml streptomycin. Cells were passed at $2\times10^5$ cells/ml every 3 days. Responsiveness of THP-1 cells to LPS was induced by culturing the cells for 48 hours in REM medium containing 10% fetal calf serum, 2 mM L-glutamine, 100 units penicillin, 100 μg/ml of streptomycin and 100 nM PMA at 37° C. in a humidified atmosphere with 5% $CO_2$. Cells were cultured in 96-well flat-bottomed tissue culture plates at $1-2\times10^5$ cells per well in a final volume of 200 μl. After 48 hours, adherent cells were washed three times with 200 μl of medium without serum. To 180 μl of medium without serum but with 0.5% HSA, LPS (10 μl at 200 ng/ml) and/or BPI, LBP or other RENPs were added (10 gl at 0–2 mg/ml) and the cells were cultured for an additional 4 hours. After 4 hours, supernatants were transferred to a U-bottomed 96 well plate and the plate was centrifuged (500×g, 12 min) to pellet any cell debris. Supernatants were then stored in a second plate at –20° C. until assayed for TNF by ELISA.

Figure 15:
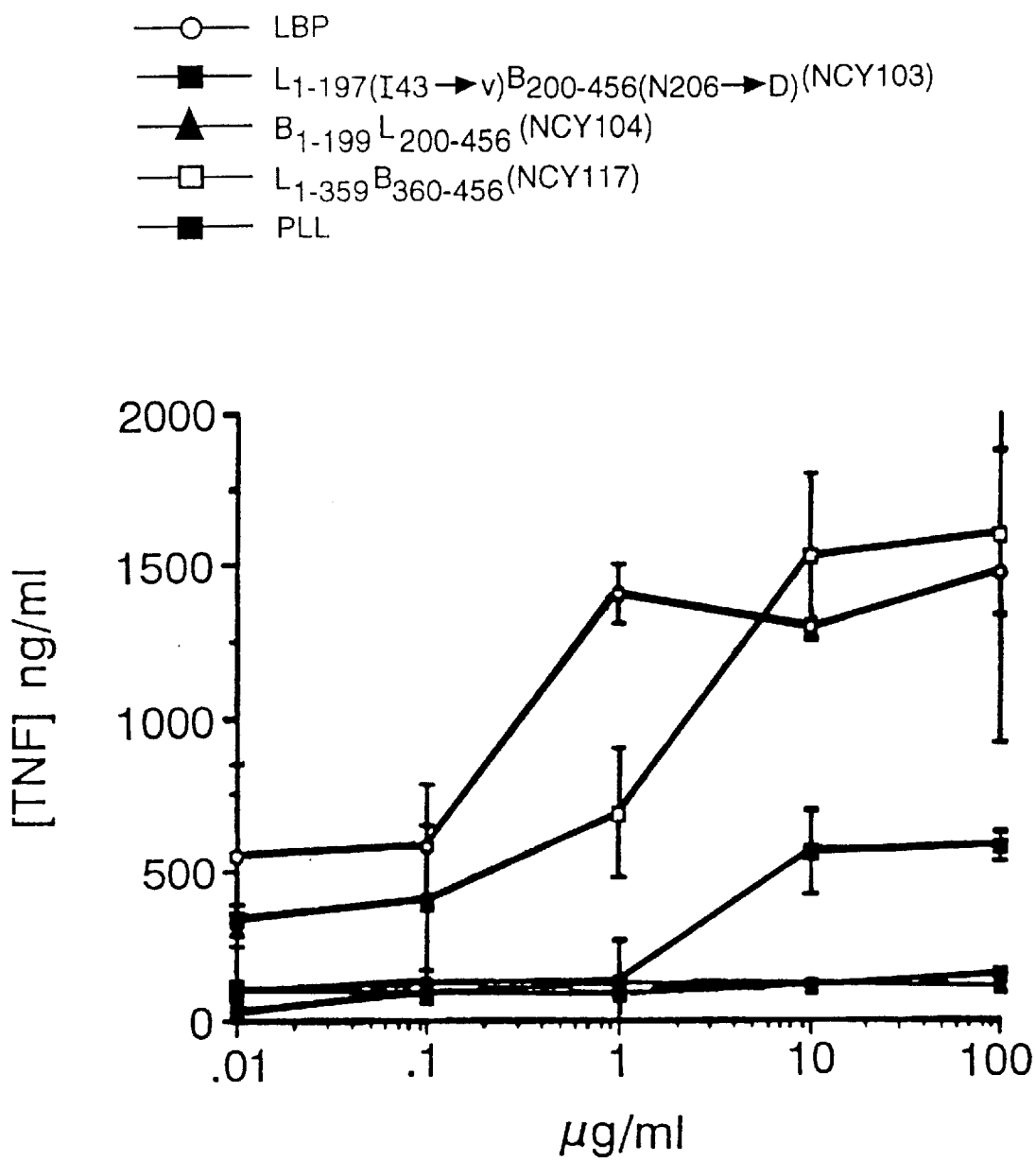
FIG. 15 is a graph comparing the effects of LBP vs. $L_{1-197(I43->V)}B_{200-456(N206->D)}$ (NCY103), $B_{1-199}L_{200-456}$ (NCY104), $L_{1-359}B_{360-456}$ (NCY117) and PLL (poly-L-lysine) on the stimulation of TNFα release by phorbol ester-induced THP-1 cells in the absence of serum.
Figure 16:
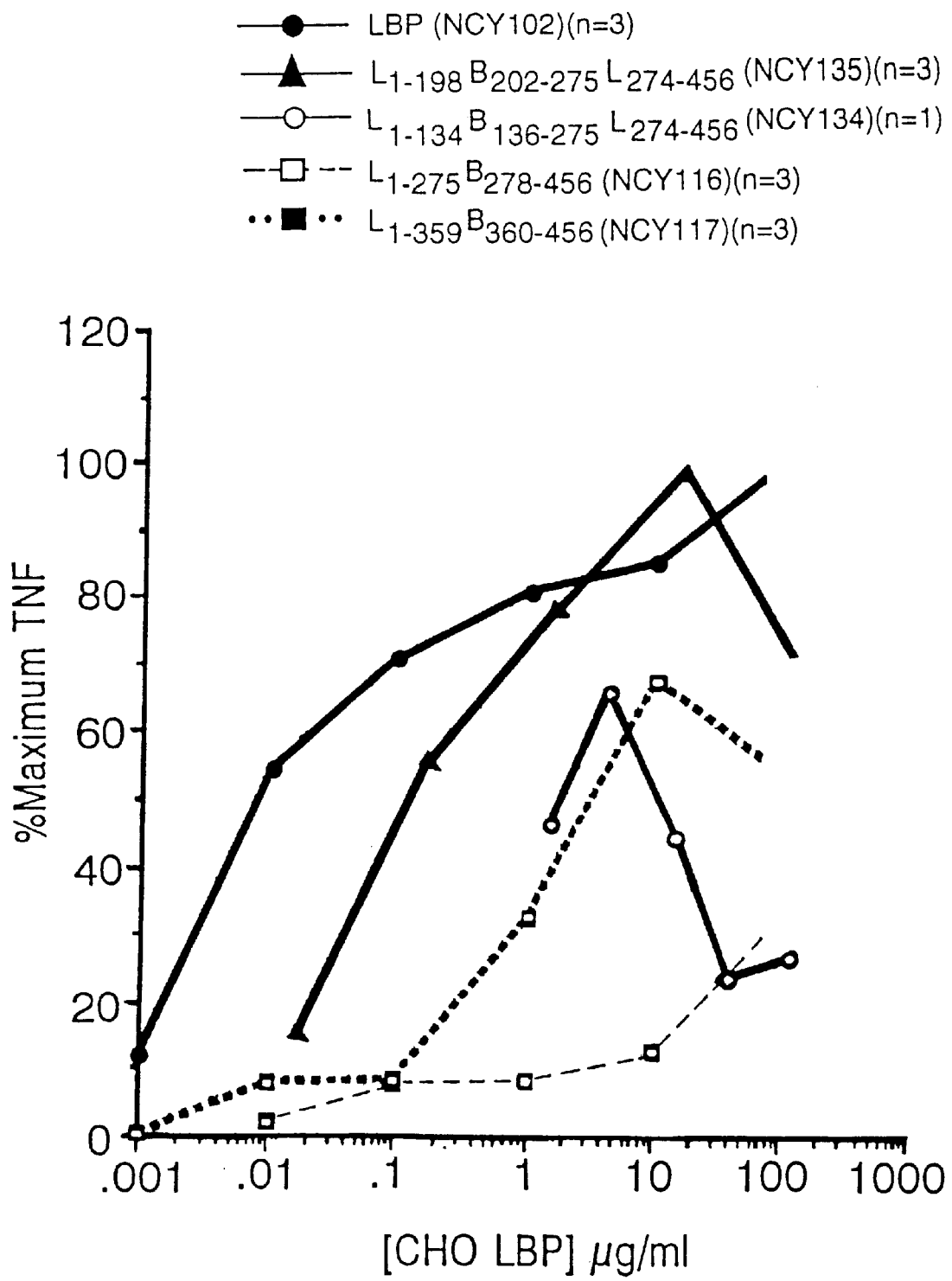
FIG. 16 is a graph showing the effects of various recombinant-endotoxin neutralizing proteins upon LPS-mediated TNF production in THP-1 cells cultured without serum.
Figure 17A:
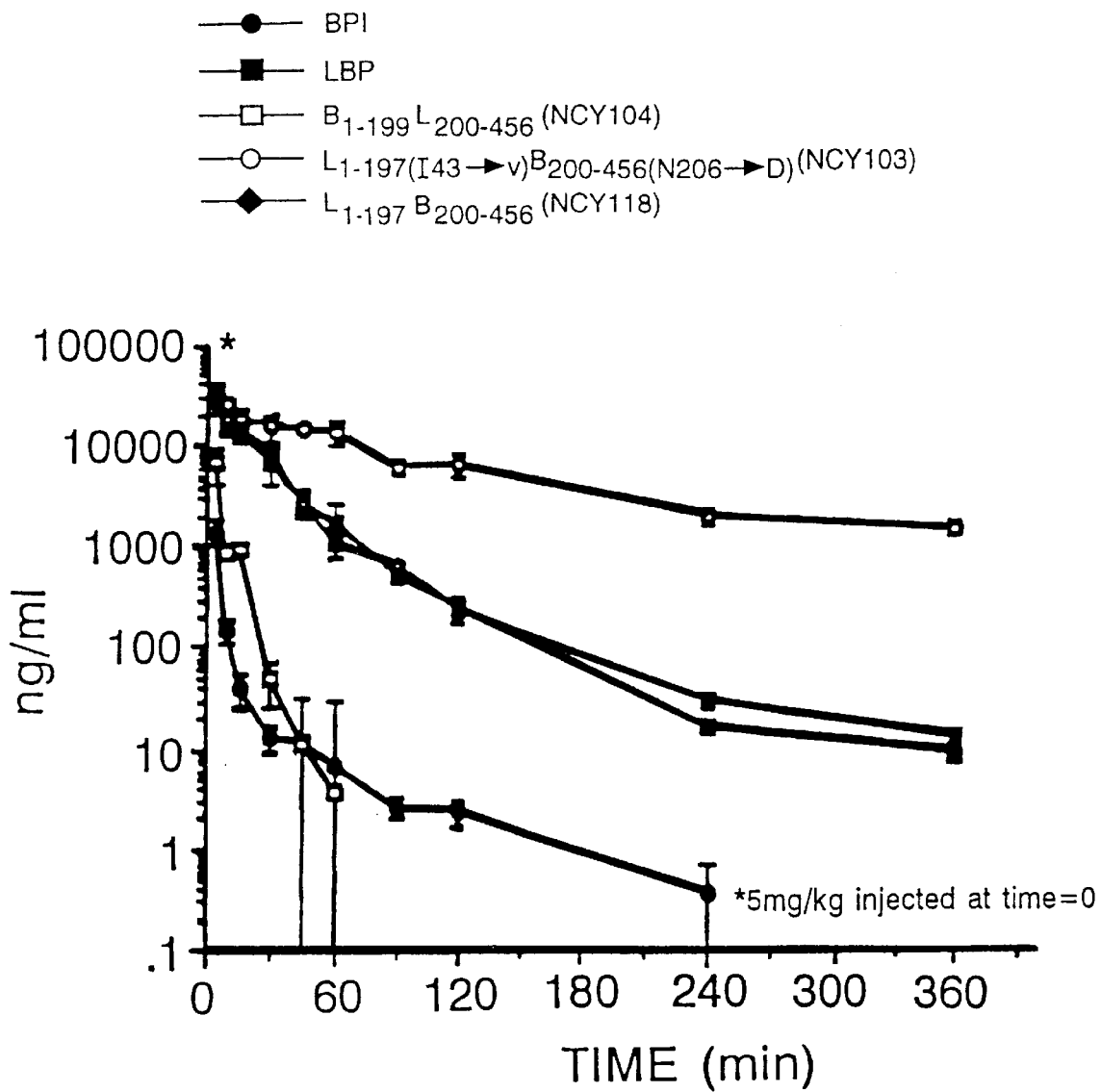
FIGS. 17A–17H are graphs showing the clearance of: BPI, LBP, $L_{1-197(I43->V)}B_{200-456(N206->D)}$ (NCY103), $B_{1-199}L_{200-456}$ (NCY104), and $L_{1-197}B_{200-456}$ (NCY118) (17A); BPI, $L_{1-59}B_{60-456}$ (NCY114), $L_{1-134}B_{135-456}$ (NCY115), and $B_{CAT9}$ (NCY139) (17B); BPI, LBP, $L_{1-359}B_{360-456}$ (NCY117) and $L_{1-197}B_{200-456}$ (NCY118) (17C); and BPI, LBP and $L_{(1-198)}B_{(201-456)}Fc$ (NCY144) (assayed for both Fc and BPI) in CD-1 mice (17D); LBP, $L_{1-275}B_{278-456}$ (NCY116), $L_{1-359}B_{360-456}$ (NCY117), $L_{1-197}B_{200-456}$ (NCY118) (17E); LBP, $L_{1-197(I43->V)}$ $B_{200-456(N206->D)}$ (NCY103), $L_{1-134}B_{135-456}$ (NCY115), $L_{(1-198)}B_{(202-275)}L_{(274-456)}$ (NCY135), and $L_{(1-134)}B_{136-275}$ $L_{(274-456)}$ (NCY134) (17F); LBP (NCY102), $L_{CAT6}$ (NCY141), $L_{CAT9}$ (NCY142), $L_{CAT15}$ (NCY143) and BPI (17G); and BPI, $L_{1-134}B_{135-456}$ (NCY115), and $L_{1-59}B_{60-456}$ (NCY114) (17H).
Figure 17B:
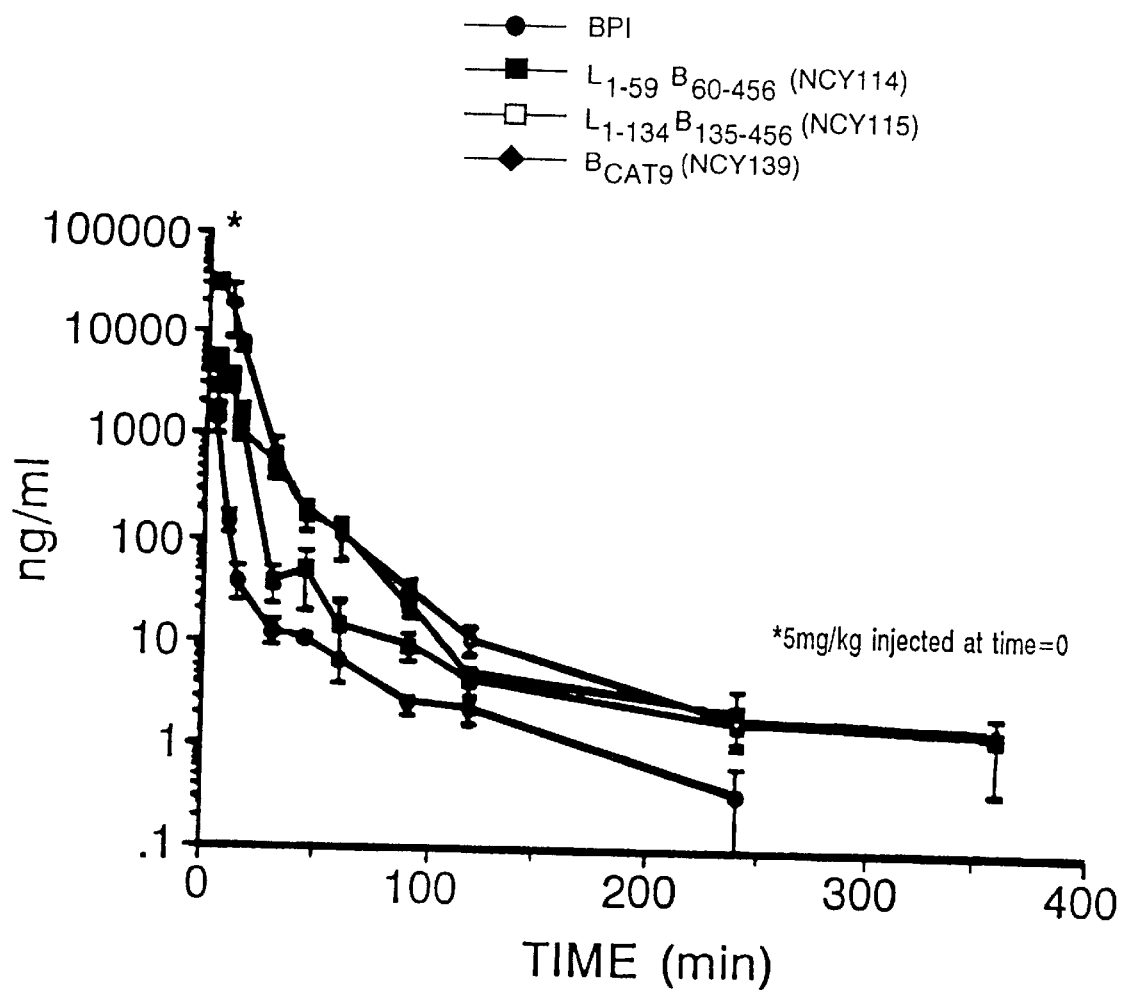
Figure 17C:
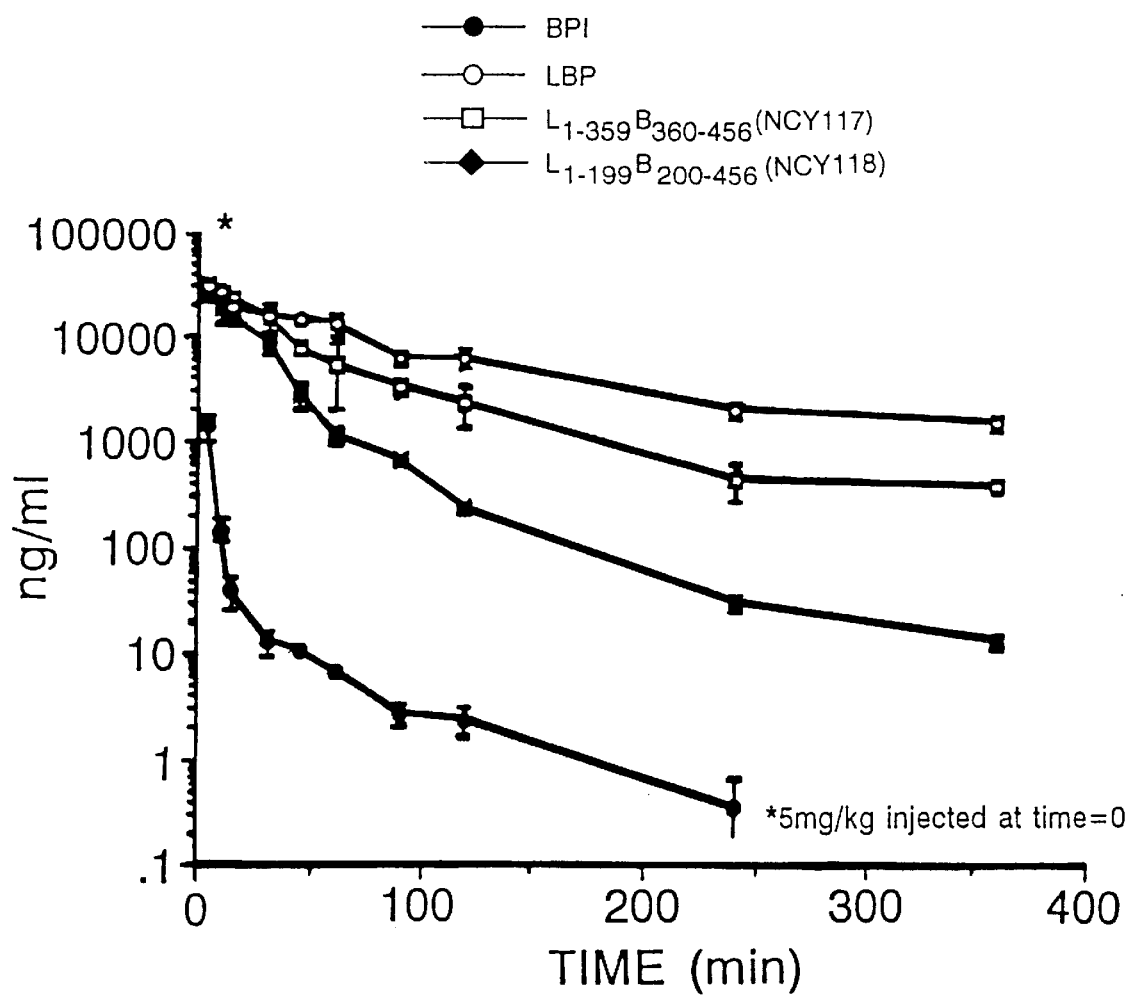
Figure 17D:
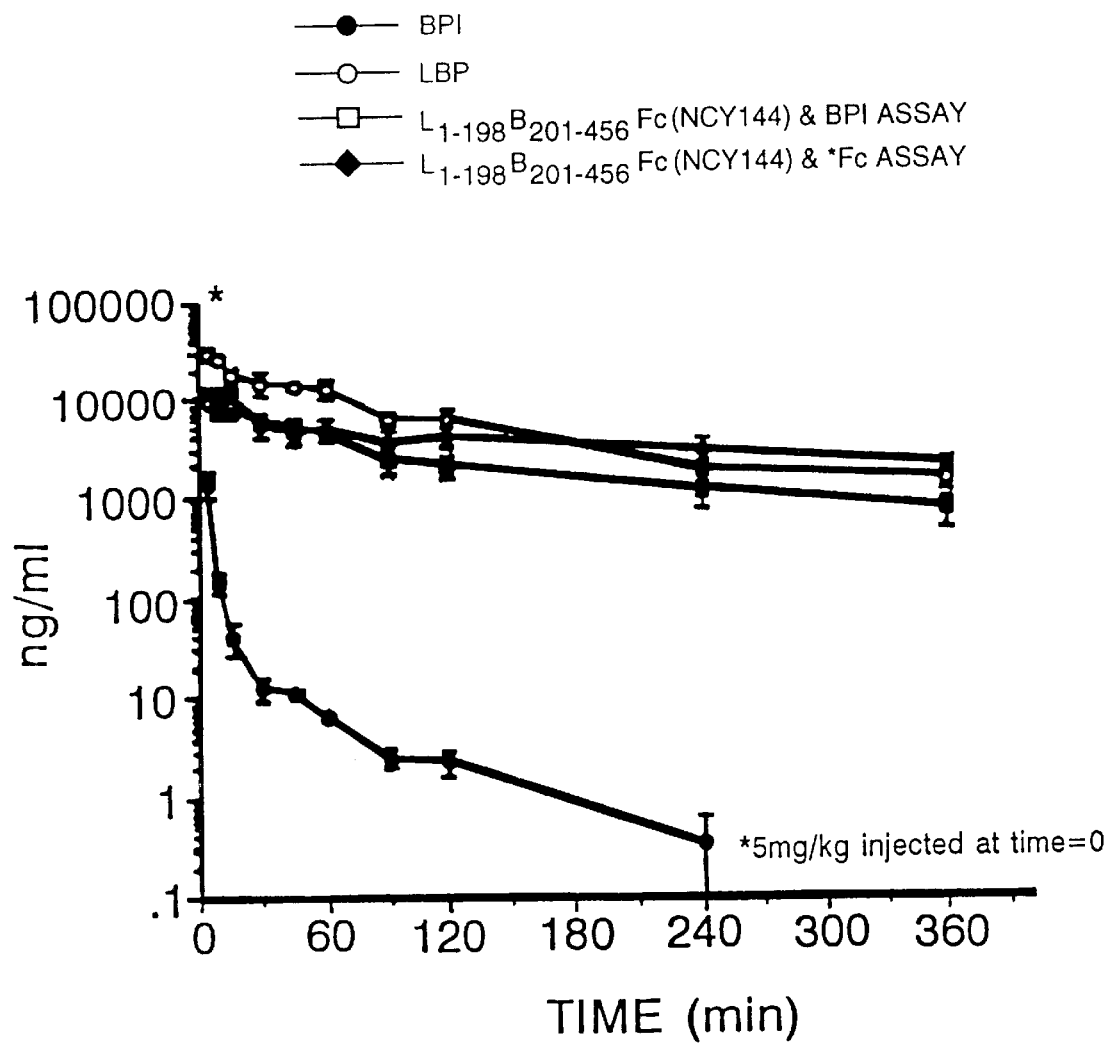
Figure 17E:
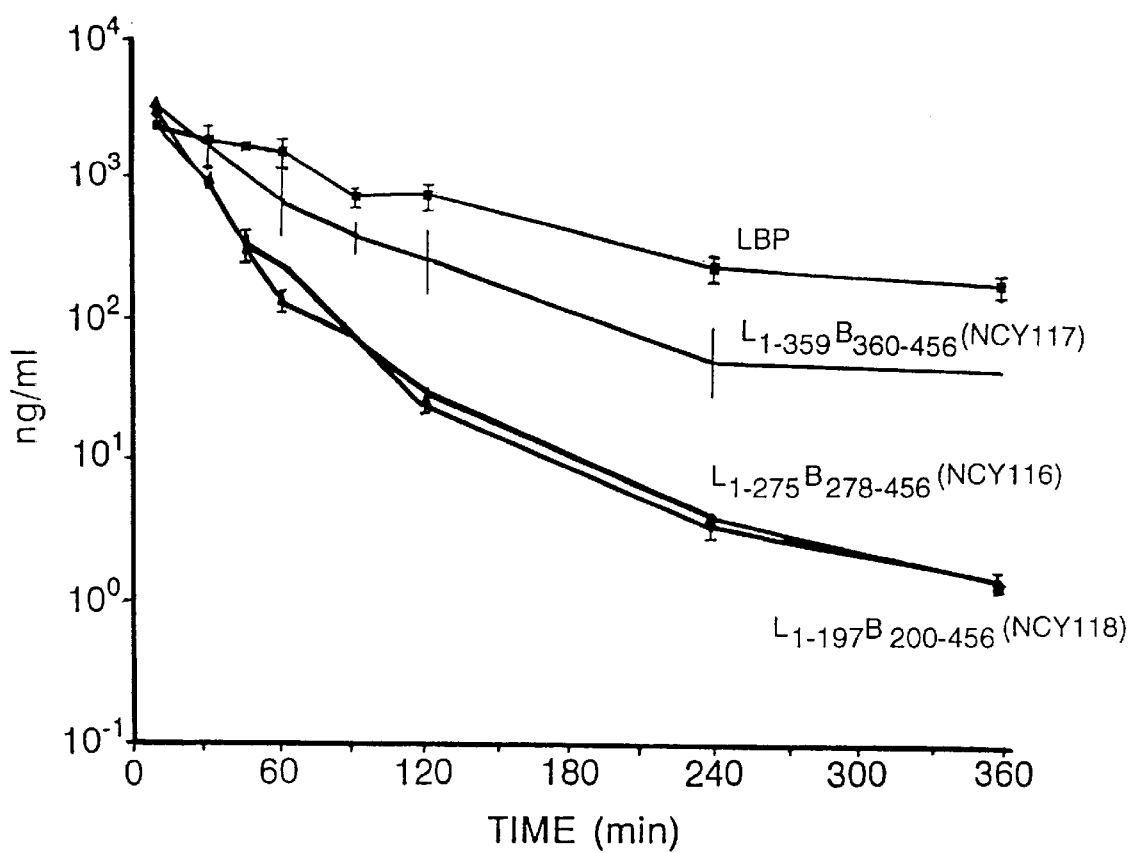
Figure 17F:
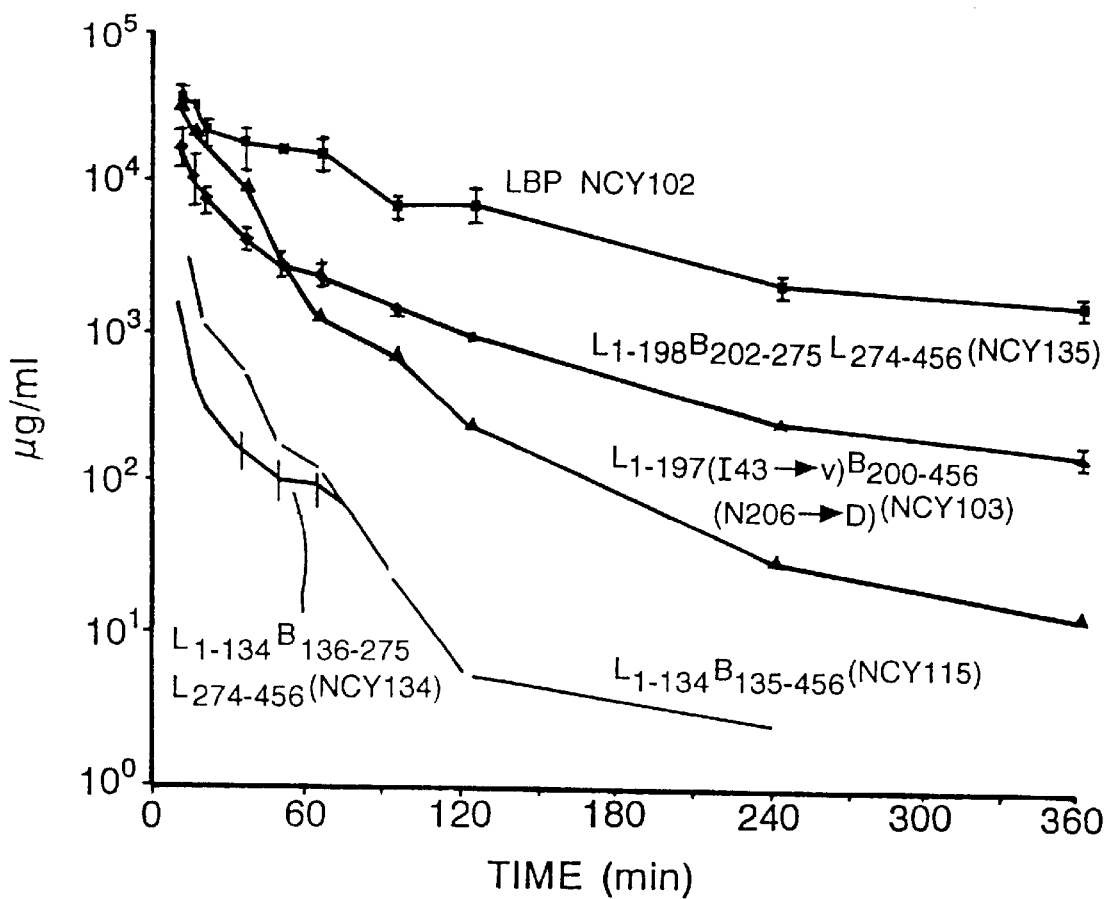
Figure 17G:
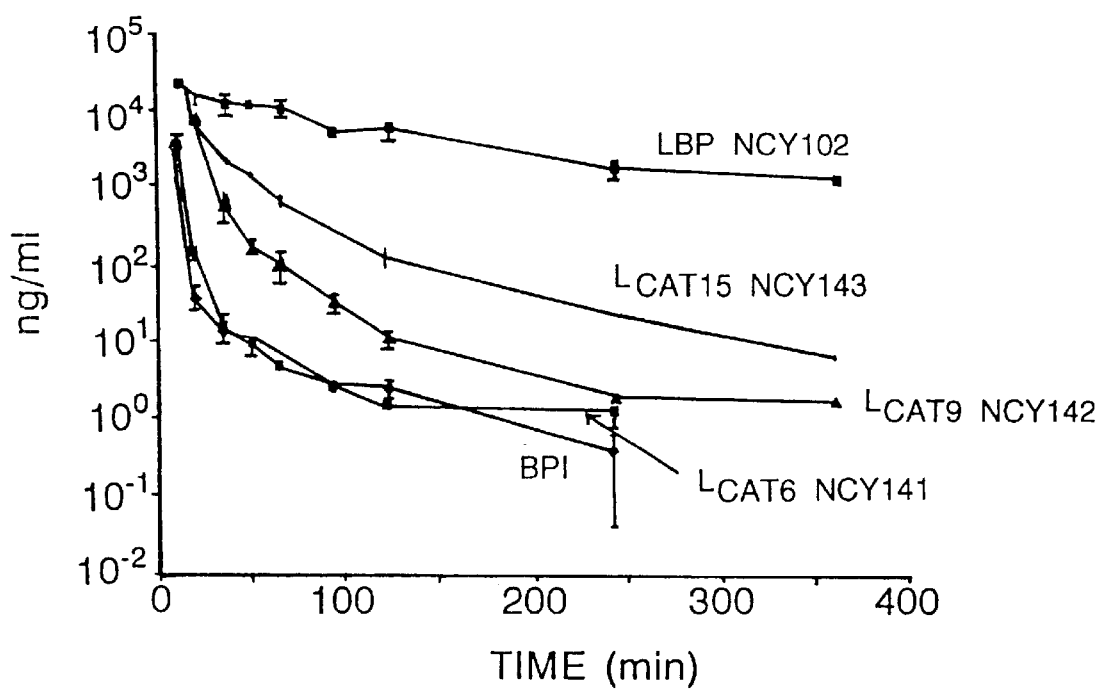
Figure 17H:
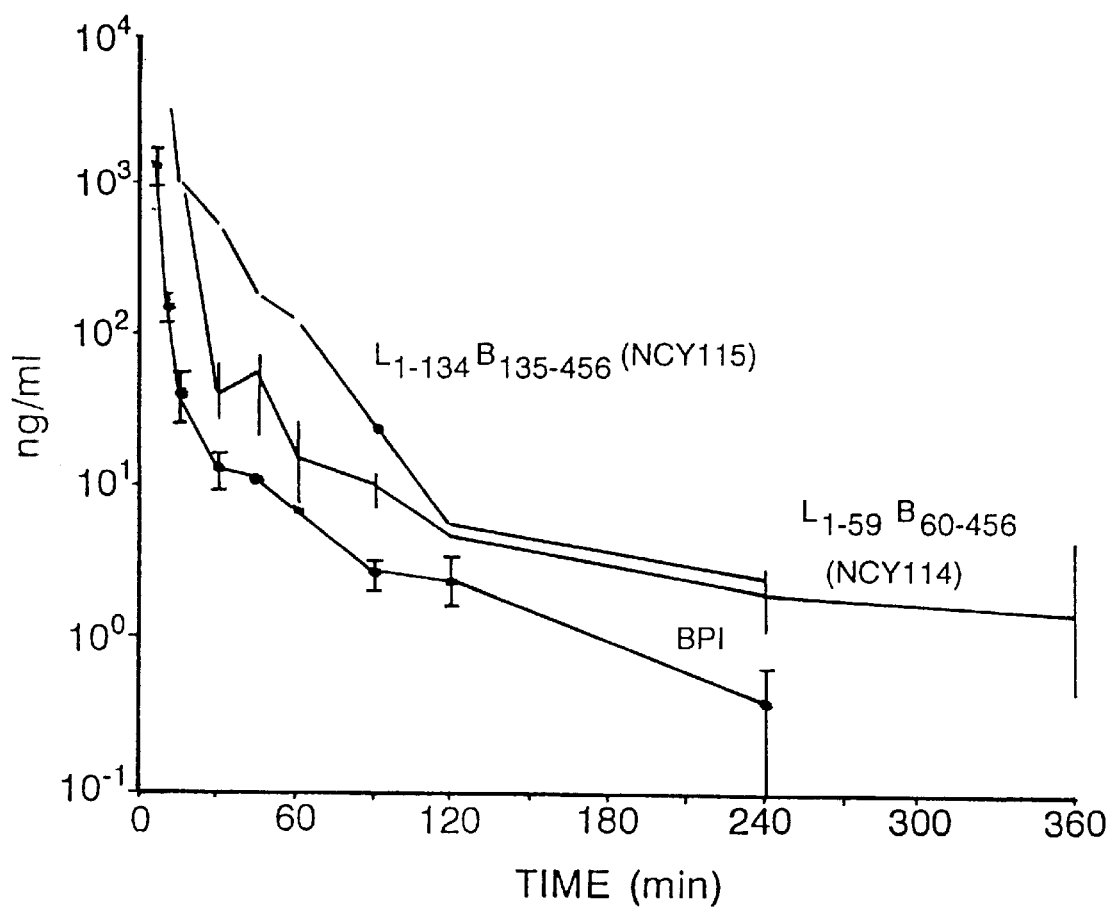

To further identify the regions of BPI which contribute to LPS-neutralizing activity, and the domains of LBP which are responsible for transducing the LPS signal to cells, the abilities of RENPs to replace LBP were compared under serum-free conditions. In these experiments, cells of the promonocytic cell line THP-1 were induced to respond to LPS by culturing for 48 hours with phorbol ester. After induction, cells were stimulated with 19 ng/ml of LPS in the presence or absence of the recombinant protein. In this system, TNF release requires a source of LBP. Data from these experiments (FIG. 15) show that only LBP and $L_{1-359}B_{360-456}$ stimulated TNF release. Thus the domain of LBP responsible for facilitating LPS-induced TNF release is within amino acid residues 199-359. Interestingly, $B_{1-199}L_{200-456}$ did not mediate TNF release in a serum-free system. This may indicate that the N-terminal domain of BPI binds too tightly to LPS to allow transfer of LPS to CD14 on the macrophage surface. FIG. 16 shows an additional comparison of TNF production. Because $L_{(1-198)}B_{(202-275)}L_{(274-456)}$ includes LBP domain 274-456 and has activity, the active domain may comprise only residues 274-359.

Example 10: LPS-Induced TNF Release in Whole Blood

Peripheral blood from normal human volunteers was collected in heparin-containing VACUTAINER™ tubes (Becton Dickinson). To one milliliter of whole blood, BPI, a protein of the subject invention, or buffer control was added, followed by 1 ng/ml $E.\ coli$ O55:B5 refined standard endotoxin (RSE) (Whitaker Bioproducts). Samples were incubated in closed microtubes at 37° C. for 4 hours on a rocking platform. At the end of the incubation, samples were centrifuged for 5 minutes at 500×g at 4° C., the plasma collected and frozen on dry ice until assayed for the presence of cytokines. TNF levels were determined by ELISA using human recombinant TNF (Genentech Inc., South San Francisco, Calif.) as a standard.

In later studies it was determined that BPI activity in whole blood is inhibited by heparin, and the anticoagulant was changed to citrate. In these experiments, to 120 μl of citrated whole blood, 20 μA of BPI or an RENP (at 0-1 mg/ml) or buffer control, 20 μl of 100 ng/ml of $E.\ coil$ O55:B5 LPS was added to stimulate cells in whole blood samples. These experiments were performed in polypropylene microtiter plates (Costar, Cambridge, Mass.). After the 37°C. incubation step, the plates were centrifuged 15 min at 500×g at 4° C. and the plasma removed for assaying.

To test the effects of BPI, LBP, and RENPs on LPS activation of TNF production in whole blood, BPI, LBP, $L_{1-197(I43->V)}B_{200-456(N206->D)}$, or $B_{1-199}L_{200-456}$ was mixed with heparinized blood, and LPS was added to the resulting mixture. The blood was incubated for four hours at 37° C., and TNF in the plasma was measured as described, supra.

Figure 10:
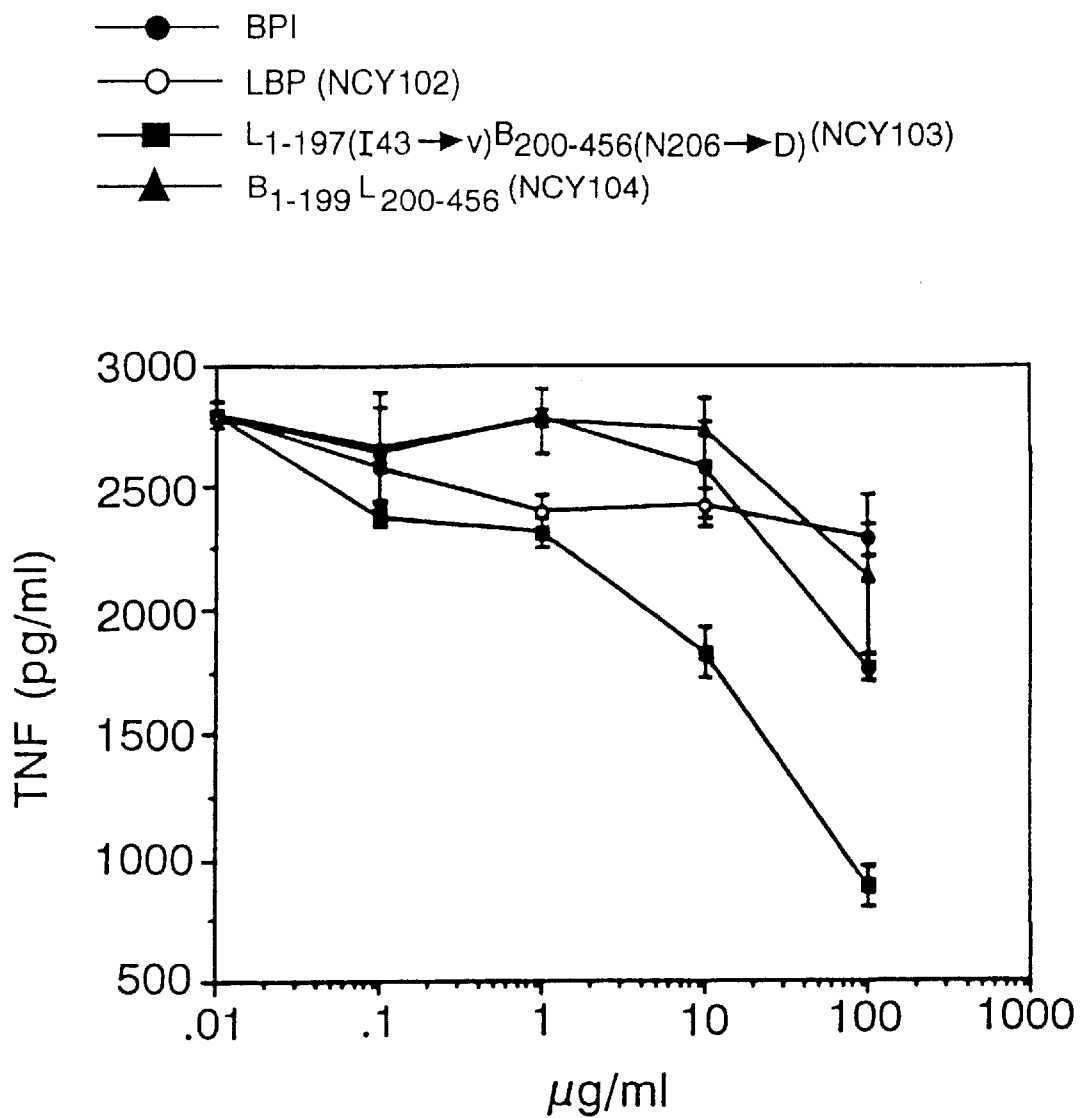
FIG. 10 is a graph showing the effects of BPI, LBP, $L_{1-197(I43->V)}B_{200-456(N206->D)}$ (NCY103) or $B_{1-199}L_{200-456}$ (NCY104), on TNF release by LPS in whole blood.

Results are shown in FIG. 10. $L_{1-197(I43->V)}B_{200-456(N206->D)}$ was the most potent at blocking TNF release, followed by BPI as the next most potent blocker. $B_{1-199}L_{200-456}$ and LBP had essentially no effect. Thus, in whole blood, $L_{1-197(I43->V)}B_{200-456(N206->D)}$ proved to be the most potent inhibitor of LPS-mediated cytokine stimulation.

When experiments were performed in citrated rather than heparinized whole blood, endotoxin-neutralizing activity of BPI and $L_{1-197(I43->V)}B_{200-456(N206->D)}$ were equivalent (Table 6). In experiments in which recombinant proteins were preincubated with endotoxin before addition to whole blood, the activities of these compounds fell roughly into two groups. BPI, $L_{1-197(I43->V)}B_{200-456(N206->D)}$, $B_{1-199}$, $B_{CAT6}$, $B_{CAT15}$, $L_{1-59}B_{60-406}$, $L_{1-134}B_{135-456}$ and $L_{1-197}B_{200-456}$ possess LPS-neutralizing activity, while LBP, $B_{1-199}L_{200-456}$, $L_{1-359}B_{360-456}$ and $B_{CAT9}$ were relatively inactive. Results with $L_{1-275}B_{278-456}$, $B_{CAT9}$, and $L_{(1-198)}B_{(201-456)}Fc$ were equivocal. When compounds were added to the blood samples immediately prior to LPS, the IC50 values were higher, but the same group of proteins showed activity. These data further indicate the role of the C-terminal region of BPI, demarcated by amino acid residues 200-359, in LPS neutralization in a physiological environment such as whole blood. Because $L_{1-199}$ is not a potent endotoxin-neutralizing protein (see Tables 9 and 11), it can be concluded that the C-terminal domain of BPI must significantly contribute to the endotoxin-neutralizing activity of $L_{1-197(I43->V)}$ $B_{200-456(N206->D)}$ and $L_{1-197}B_{200-456}$. All compounds which contain this sequence (201-359) are active except $B_{CAT9}$, which was also inactive in other assays possibly because the cationic amino acid residues which were replaced may be important in configuring the molecule. These data indicate that $L_{1-197(I43->V)}B_{200-456(N206->D)}$ is equivalent to $L_{1-197}B_{200-456}$ in activity, thus implying that the amino acid differences between these two proteins have no affect upon LPS binding affinity.

TABLE 6

LPS Inhibition in Human Whole Blood

| Protein Pre-incubated | IC50 (µg/ml) | n | Not Pre-incubated | IC50 (µg/ml) | n |
|---|---|---|---|---|---|
| $L_{1-134}B_{135-456}$ | 0.15 ± 0.12 | 3 | BPI | 2.60 ± 1.52 | 5 |
| $L_{1-197}B_{200-456}$ | 2.90 ± 3.59 | 12 | $L_{1-134}B_{135-456}$ | 3.7 ± 1.60 | 2 |
| $L_{1-59}B_{60-456}$ | 0.28 ± 0.25 | 3 | $L_{1-199\backslash7(I43->V)}B_{200-456(N206->D)}$ | 7.13 ± 5.92 | 4 |
| $L_{1-197(I43->V)}B_{200-456(N206->D)}$ | 0.16 ± 0.11 | 17 | $L_{1-59}B_{60-456}$ | 15 ± 18.58 | 2 |
| BPI | 0.43 ± 0.49 | 13 | $L_{1-197}B_{200-456}$ | 26.5 ± 0.71 | 2 |
| $L_{(1-198)}B_{(201-456)}Fc$ | 18.00 ± 27.73 | 3 | $L_{1-359}B_{360-456}$ | >100 | 1 |
| $B_{1-199}L_{200-456}$ | >100 | 3 | $B_{CAT9}$ | >100 | 2 |
| $L_{1-359}B_{360-456}$ | >100 | 3 | $L_{(1-198)}B_{(201-456)}Fc$ | >100 | 2 |
| $B_{CAT9}$ | 11.50 ± 3.54 | 2* | $B_{1-199}L_{200-456}$ | ND | |
| $B_{1-199}$ | 0.73 ± 0.48 | 6 | $B_{1-199}$ | 4.0 | 1 |
| $L_{1-199}$ | >100 | 2 | $L_{1-199}$ | >100 | 1 |
| $B_{CAT15}$ | 0.21 ± 0.26 | 3 | | | |
| $B_{CAT6}$ | 0.27 ± 0.25 | 2 | | | |
| $L_{(1-134)}B_{(136-275)}L_{(274-456)}$ | 2.0 | 1 | | | |
| $L_{(1-198)}B_{(202-275)}L_{(274-456)}$ | 5.27 ± 5.83 | 3 | | | |
| $L_{1-275}B_{278-456}$ | 38.10 ± 53.64 | 3 | | | |

*Two additional values for $B_{CAT9}$ were >100.

Example 11: Mouse Serum Half-Life Assay

CD-1 mice weighing approximately 20 grams were injected with 5 mg/kg body weight BPI, LBP, or RENPs (1 mg/ml) at time zero. In heparinized (or later EDTA-containing) tubes, blood was collected from the retroorbital plexus from three animals for each time point tested. A typical blood collection schedule was 5, 10, 15, 30, 45, 60, 90, 120, 240, and 360 minutes. The EDTA anticoagulated blood was centrifuged for about 10 min at 1000×g and the supernatant plasma removed and stored frozen on dry ice until tested. Levels of BPI, LBP, or RENP in the plasma samples were determined by ELISA using the appropriate protein as the standard.

A potent anti-endotoxin therapeutic should not only neutralize endotoxin, but should also have the capacity to clear endotoxin from the circulation. The circulating levels of radioactively labeled $^{125}$I-BPI were measured in the mouse in the presence and absence of endotoxin (Table 7).

In the absence of endotoxin, the elimination (alpha) phase for $^{125}$I-BPI was less than two minutes. In the presence of LPS, the alpha phase was extended to 6.2 minutes. $^{125}$I-LpS alone has a single phase distribution (beta) with a half-life of about 101 minutes. When $^{125}$I-LPS and unlabeled BPI were administered, a 6.2 minute elimination (alpha) phase was observed, indicating that elimination was remarkably facilitated by BPI.

TABLE 7

Serum Half-Life of BPI and LPS in the Mouse

| Test Article | t½alpha | t½beta |
|---|---|---|
| $^{125}$I-BPI | 1.6 | 103.0 |
| $^{125}$I-BPI + LPS | 6.3 | 72.0 |

TABLE 7-continued

Serum Half-Life of BPI and LPS in the Mouse

| Test Article | t½alpha | t½beta |
|---|---|---|
| $^{125}$I-LPS | — | 101.0 |
| $^{125}$I-LPS + BPI | 6.2 | 114.0 |

Figure 11:
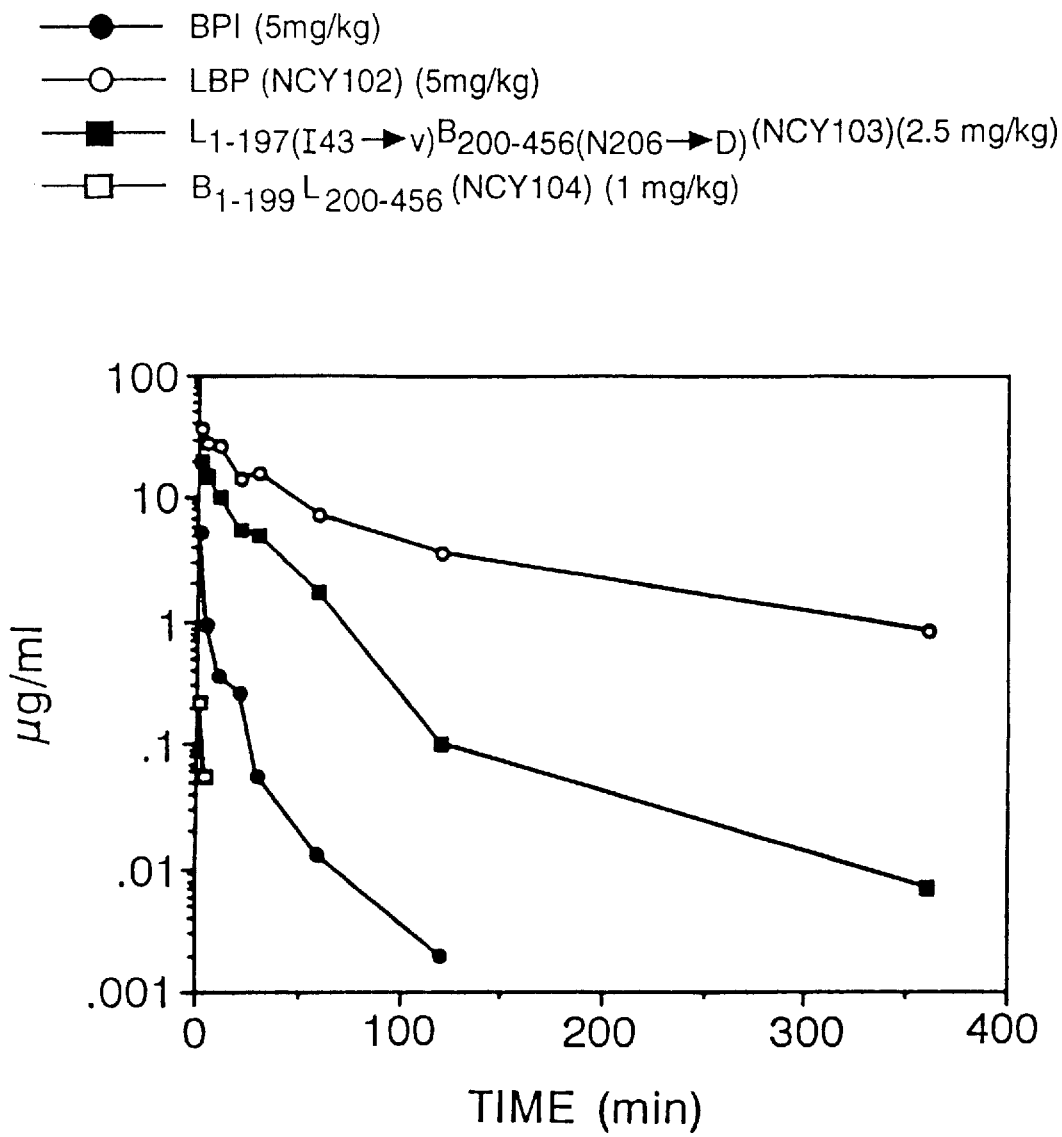
FIG. 11 is a graph showing clearance of BPI, LBP, $L_{1-197(I43->V)}B_{200-456(N206->D)}$ (NCY103) or $B_{1-199}L_{200-456}$ (NCY104) from mouse serum after intravenous injection.

In order to determine whether the very short circulating half-life of BPI could be extended by molecular engineering, the circulating half-lives of BPI, LBP, $B_{1-199}L_{200-456}$ and $L_{1-197(I43->V)}B_{200-456(N206->D)}$ were compared (FIG. 11). Using both labeled and unlabeled material, it was observed that the circulating half-life of BPI in the mouse is remarkably short. This may be a result of the highly cationic nature of BPI having a predicted pI of 10.6. LBP, normally present in the circulation at concentrations of 10 µg/ml, has a predicted pI of about 6.8. As expected, $L_{1-197(I43->V)}B_{200-456(N206->D)}$ (LBP-BPI chimera lacking BPI cationic residues) has a markedly longer circulating half-life than $B_{1-199}L_{200-456}$ (BPI-LBP chimera having BPI cationic residues). FIG. 11 shows that $L_{1-197(I43->V)}B_{200-456(N206->D)}$ indeed has a longer half-life than BPI. $B_{1-199}L_{200-456}$, with the N-terminal domain of BPI, had an even shorter half-life than that of BPI. Thus, the N-terminal domain of BPI appears to play a major role in its short circulating half-life.

Further pharmacokinetic studies were performed in which recombinant proteins of the subject invention were administered to CD-1 mice at a 5 mg/kg bolus dose. Results of these experiments are shown in FIGS. 17A–17H. At 5 mg/kg, the circulating half life of $B_{1-199}L_{200-456}$ was similar to that of BPI. $L_{1-197(I43->V)}B_{200-456(N206->D)}$ and $L_{1-197}B_{200-456}$ had overlapping elimination curves and again indicating that these two molecules are equivalent with respect to their biological activities. $L_{1-197(I43->V)}B_{200-456(N206->D)}$ and $B_{1-199}$ persisted in the circulation significantly longer than BPI or $B_{1-199}L_{200-456}$, but not as long as the serum protein LBP. Comparison of the elimination curves of $L_{1-59}B_{60-456}$, $L_{1-134}B_{135-456}$ and $B_{BCAT9}$ revealed that the N-terminus of LBP plays a role in extending circulating half-life. $L_{1-59}B_{60-456}$ circulates slightly longer than BPI, and contains the least LBP sequence of any of the recombinant proteins tested (amino acid residues 1-59). $L_{1-134}B_{135-456}$ was cleared somewhat more slowly, indicating that LBP amino acid residues 60-134 of LBP impart a longer circulating half-life. In contrast, the cationic residues of BPI between 134-199 shorten the half-life, since in $B_{CAT9}$, where the cationic residues in this region were replaced with the corresponding residues of LBP, the half-life was similar to that of $L_{1-134}B_{135-456}$. Including more LBP residues in the N-terminal domain further extends the half life. If amino acid residues 199-359 of LBP are added ($L_{1-359}B_{360-456}$), the half-life is longer, but not quite as long as that of LBP. Likewise $L_{(1-198)}B_{(202-275)}L_{(274-456)}$ (with LBP domain 1-198 and 274-456) has a relatively long t1/2. These results indicate that the more "LBP-like" the molecule is, the longer it circulates. In addition, combining an Ig fragment Fc with $L_{1-197(I43->V)}B_{200-456(N206->D)}$ gives the longest half life.

Example 13: Mouse Endotoxin Challenge Assay

Female CD-1 mice were injected in the lateral tail vein with a $LD_{100}$ dose (25-35 mg/kg) of *Salmonella abortus equi* endotoxin, which was followed by an injection of BPI, RENP, or vehicle control into the opposite lateral tail vein at the indicated time. Protein injection concentrations varied and provided doses of 0.5, 1, and 5 mg/kg. Use of vehicle control illustrated the lethality of the endotoxin challenge in the test animal. Animals were observed for mortality at 24, 28, and 72 hours. Preliminary studies showed that mortality does not change from day three to day seven or beyond.

The efficacies of BPI, LBP, $L_{1-197(I43->V)}B_{200-456(N206->D)}$, $B_{1-199}L_{200-456}$ and $B_{(S351->A)}$ against lethal endotoxin challenge in mice were compared (Tables 8-10). The efficacies of $L_{1-197(I43->V)}B_{200-456(N206->D)}$, $L_{1-197}B_{200-456}$, $L_{1-59}B_{60-456}$, $L_{1-134}B_{135-456}$, $L_{(1-198)}B_{(201-456)}Fc$, $L_{1-275}B_{278-456}$, $L_{1-359}B_{360-456}$, $B_{CAT9}$, $B_{CAT6}$, and $B_{CAT15}$ against lethal endotoxin challenge in mice were also compared (Table 11). When each protein was given within two minutes after lethal endotoxin challenge, BPI, $L_{1-197(I43->V)}B_{200-456(N206->D)}$ and $B_{(S351->A)}$ had similar potency, whereas LBP and $B_{1-199}L_{220-456}$ showed minimal protection. The marginal protective effects of LBP and $B_{1-199}L_{220-456}$ since these agents do not block the inflammatory signal of LPS acting on human cells in vitro (FIG. 10).

TABLE 8

Mouse Endotoxin Challenge
Comparison of BPI, LBP (NCY102),
and $L_{1-197(143->V)}B_{200-456(N206->D)}$ (NCY103)

| Drug | Dose | % Survival (n = 10) |
|---|---|---|
| Control | 0 mg/kg | 0% |
| BPI | 5 mg/kg | 60% |
|  | 1 mg/kg | 40% |
| LBP | 5 mg/kg | 30% |
|  | 1 mg/kg | 20% |
| $L_{1-197(143->V)}B_{200-456(N206->D)}$ | 5 mg/kg | 60% |
|  | 1 mg/kg | 50% |

TABLE 9

Mouse Endotoxin Challenge
Comparison of BPI, $L_{1-197(143->V)}B_{200-456(N206->D)}$ and $B_{(S351->A)}$

| Drug | Dose | % Survival (n = 10) |
|---|---|---|
| Control | 0 mg/kg | 0% |
| BPI | 5 mg/kg | 80% |
| $L_{1-197(143->V)}B_{200-456(N206->D)}$ | 5 mg/kg | 100% |
| $B_{(S351->A)}$ | 5 mg/kg | 90% |

TABLE 10

Mouse Endotoxin Challenge
Comparison of BPI and $B_{1-199}L_{200-456}$ (NCY104)

| Drug | Dose | % Survival (n = 10) |
|---|---|---|
| Control | 0 mg/kg | 40% |
| BPI | 10 mg/kg | 100% |
|  | 2 mg/kg | 100% |
|  | 0.4 mg/kg | 70% |
| $B_{1-199}L_{200-456}$ | 10 mg/kg | 60% |
|  | 2 mg/kg | 60% |
|  | 0.2 mg/kg | 50% |

TABLE 11

Survival in CD-1 Mice Following Lethal Endotoxin Challenge

Panel A

|  | Survivors/n | % Survival | p (vs. control) |
|---|---|---|---|
| BPI | 40/50 | 80.00 | <0.001 |
| $L_{1-197(I43 \to V)}B_{200-456(N206 \to D)}$ | 17/20 | 85.00 | <0.001 |
| $L_{1-197}B_{200-456}$ | 16/20 | 80.00 | <0.001 |
| $L_{1-59}B_{60-456}$ | 13/20 | 65.00 | <0.001 |
| $L_{1-134}B_{135-456}$ | 13/20 | 65.00 | <0.001 |
| $L_{(1-198)}B_{(201-456)}Fc$ | 5/10 | 50.00 | 0.001 |
| $L_{1-359}B_{360-456}$ | 2/10 | 20.00 | 0.149 |
| $B_{CAT6}$ | 9/10 | 90.00 | <0.001 |
| $B_{CAT9}$ | 1/10 | 10.00 | 0.442 |
| $L_{1-275}B_{278-456}$ | 0/10 | 0 | — |
| $B_{CAT15}$ | 6/10 | 60.0 | <0.05 |
| Control | 1/30 | 3.30 | — |

Panel B

|  | Dose mg/kg | Survivors (n = 20) | % Survival | p (vs. control)* |
|---|---|---|---|---|
| BPI | 5 | 13 | 65 | <0.001 |
|  | 1 | 9 | 45 | 0.002 |
|  | 0.5 | 6 | 30 | 0.0 |
| $L_{1-97(I43 \to V)}B_{200-456(N206 \to D)}$ | 5 | 18 | 90 | <0.001 |
|  | 1 | 12 | 60 | <0.001 |
|  | 0.5 | 9 | 45 | 0.001 |
| $B_{1-199}$ | 5 | 3 | 15 | NS |
|  | 1 | 0 | 0 | NS |
|  | 0.5 | 1 | 5 | NS |

Figure 12:
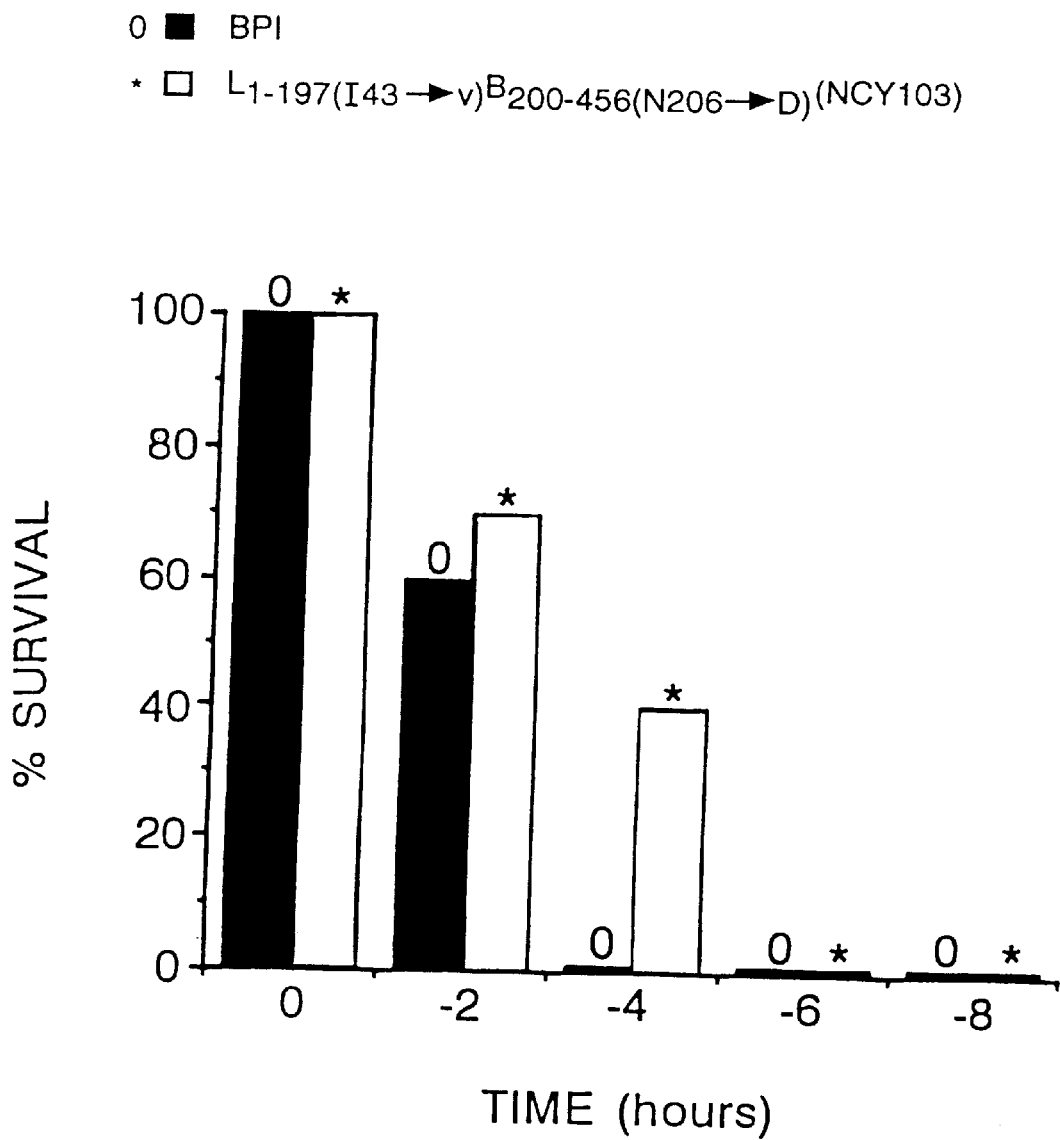
FIG. 12 is a graph comparing the efficacy of BPI and $L_{1-197(I43->V)}B_{200-456(N206->D)}$ (NCY103) in the protection to endotoxin challenge.

*Fisher's Exact Test $L_{1-197(I43 \to V)}B_{200-456(N206 \to D)}$ was markedly more effective than BPI when given more than an hour before or after LPS (FIG. 12). These results indicate that the longer circulating half-life of $L_{1-197(I43 \to V)}B_{200-456(N206 \to D)}$, or perhaps the increased ability of $L_{1-197(I43 \to V)}B_{200-456(N206 \to D)}$ to inhibit endotoxin in whole blood, has a dramatic effect on $L_{1-197(I43 \to V)}B_{200-456(N206 \to D)}$ efficacy in vivo.

Further experiments were performed to assess the LPS-neutralizing activities of recombinant proteins of the subject invention in vivo. In these experiments, a lethal LPS challenge was administered at time zero, followed immediately by a 5 mg/kg bolus injection of recombinant protein.

Example 12: BPI Reduction of LPS-Induced Cytokine Function and Mortality in Rats The potential effect of BPI against LPS related cytokine formation and mortality was investigated in rats with either (a) hemorrhagic shock (bled to lower pressure to 30–35 mmHg mean arterial pressure for 90 minutes, followed by reinfusion of shed blood and an equal volume of Ringer's over 30 minutes), or (b) endotoxic shock (caused by 100 µg LPS and 500 mg D-galactosamine/ kg). Similarly, recombinant BPI binds LPS and inhibits TNF formation in vitro. Treatment comprised 5 mg BPI/kg i.v. for the BPI group, or 1 ml saline i.v. for the control group.

The results of the investigation of BPI efficacy in rats with either (a) hemorrhagic shock or (b) endotoxic shock show that (a) in rats with hemorrhagic shock, the mortality was decreased from 5/10 (50% control group) to 2/10 (20% BPI group) at 48 hours; (b) in rats with endotoxic shock, the 5-day mortality was significantly reduced (p=0.055) by BPI treatment to 43%, as compared to 83% in the control group. Plasma LPS levels were at least partially neutralized at two hours (5.9±4.1 vs 10.8±4.1 ng/ml). Cytokine formation was concomitantly reduced in the BPI group as measured by plasma TNF levels at two hours (3.9±2.9 vs 10.3±6.3 ng/ml). Liver transaminases (GOT and GPT, whose elevation indicates hepatic dysfunction) and bilirubin still increased at eight hours; however, the increase was less with BPI. These data demonstrate that BPI has utility as a therapeutic agent against endotoxin-related disorders in hemorrhagic as well as endotoxic shock.

Example 14: Protection Against LPS Challenge by Intrarulmonary Delivery of RENPs Anesthetized male CD-1 mice were treated intra-nasally with 1 or 10 µg of either BPI or $L_{1-197(I43 \to V)}B_{200-456(N206 \to D)}$ in 50 µl. Control animals received 50 µl of saline for injection. After 20 minutes, animals were re-anesthetized, and challenged with 10 ng of E. coli 055:B5 LPS. One hour after endotoxin challenge, mice were re-anesthetized, and 0.7 ml of saline containing 1% human serum albumin was added to the lungs via the trachea. The lungs were gently kneaded. A 0.5 ml volume of BAL (bronchoalveolar lavage) fluid was aspirated, cells were pelleted by centrifugation, and the BAL sample was sorted at −70° C. The TNF-alpha level in the BAL fluid was determined by ELISA (results shown in FIG. 19).

Figure 19:
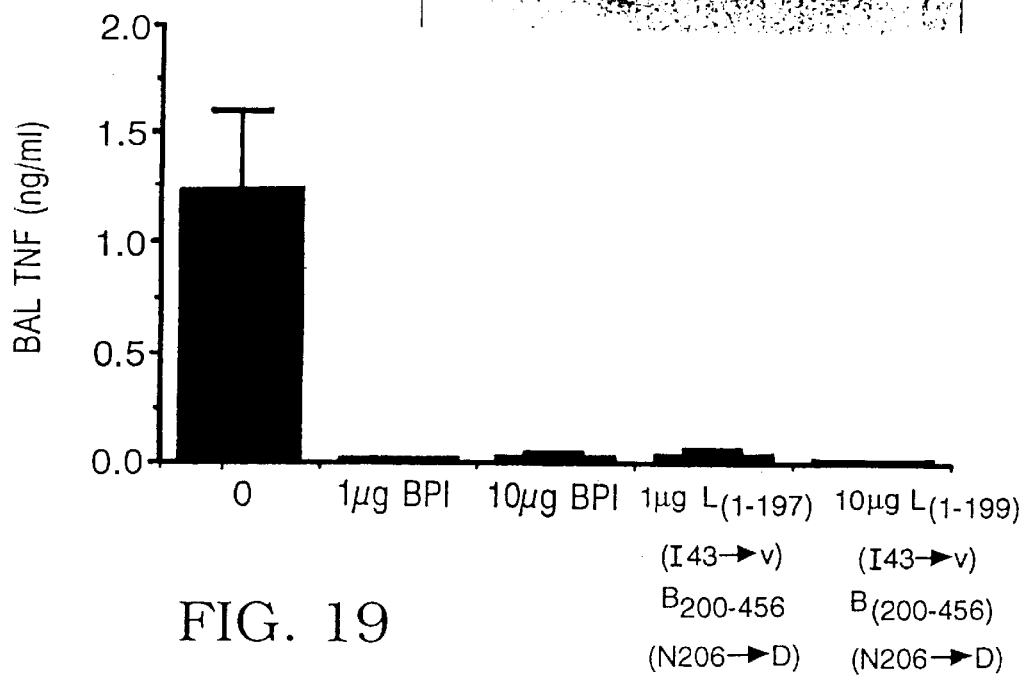
FIG. 19 is a graph showing the effects of BPI and $L_{1-197(I43->V)}B_{200-456(N206->D)}$ (NCY103) on endotoxin activation of monocytes.

FIG. 19 shows that endotoxin-neutralizing proteins such as BPI and $L_{1-197(I43 \to V)}B_{200-456(N206 \to D)}$ (NCY103) can also neutralize endotoxin-mediated TNF release in the lung. These results indicate that these proteins are effective when delivered directly into the lung and thus may be useful for treatment of pneumonias and other endotoxin-related disorders of the lung, such as ARDS.

Example 15: Construction of $L_{1-197}B_{200-456}$ cDNA encoding $L_{1-197}B_{200-456}$ was constructed by creating a unique ClaI site at the junction between the nucleotide sequence coding for $Ile_{197}$-$Asp_{198}$ residues (ATA-GAT-> ATC-GAT). For $L_{1-197}B_{200-456}$, a 0.7 kb NheI/ClaI DNA fragment (encoding amino acids 1-197) derived from the 5' sequence of LBP and a 0.8 kb ClaI/XhoI fragment (encoding amino acids 200-456) derived from the 3' sequence of BPI were generated by PCR. The chimeric cDNAs were spliced together by cloning the fragments into pSE, a mammalian vector. The cDNAs for BPI, LBP and $L_{1-197}B_{200-456}$ were transfected into Chinese hamster ovary cells (strain DUXB11) using lipofectin. The resulting transformed cells were selected, and expression was amplified with methotrexate. Cell culture supernatants were screened for reactivity by ELISA. Recombinant BPI, LBP, and $L_{1-197}B_{200-456}$ were purified as described above.

Example 16: Pharmokinetics of $L_{1-197}B_{200-456}$

Data for pharmacokinetic analysis were collected from healthy CD-1 mice given a single bolus injection (5 mg/kg) of recombinant protein at time=0. Blood was collected from three mice for each collection time point by retroorbital puncture at timepoints over three hours. Blood samples anticoagulated in EDTA were assayed by a double antibody sandwich ELISA for the presence of BPI, LBP or $L_{1-197}B_{200-456}$. Pharmacokinetic analysis was performed using a non-compartmental analysis (PharmK pharmacokinetic software, SoftRes, Inc.).

Comparison of BPI and LBP shows that BPI was cleared rapidly with a clearance rate of 13.0 ml/minute (Table 12). LBP had the longest half life, with a clearance rate of 0.042 ml/min. Compared to BPI, LBP was cleared 310 times more slowly. $L_{1-197}B_{200-456}$ had an intermediate half life (Clearance rate=0.175 ml/min), being cleared 74 times more slowly than BPI.

TABLE 12

Clearance rate of $L_{1-197}B_{200-456}$

| | CL (ml/min) | (vs. BPI) |
|---|---|---|
| BPI | 13.000 | — |
| LBP | 0.042 | (310 fold) |
| $L_{1-197}B_{200-456}$ | 0.175 | (74 fold) |

Example 17: LPS protection by $L_{1-197}B_{200-456}$

Female CD-1 mice (n=10) were injected in the lateral tail vein with 35 mg/kg S. abortus equi LPS (Sigma, St. Louis, Mo.) at time=0. Recombinant protein (5 mg/kg) was then administered intravenously into the opposite lateral tail vein immediately following (t=0) endotoxin challenge. Survival was monitored at 24, 48 and 72 hours post-challenge. Control animals received 0.1 ml saline instead of recombinant protein. The p values were determined by Fisher's exact test.

Figure 20:
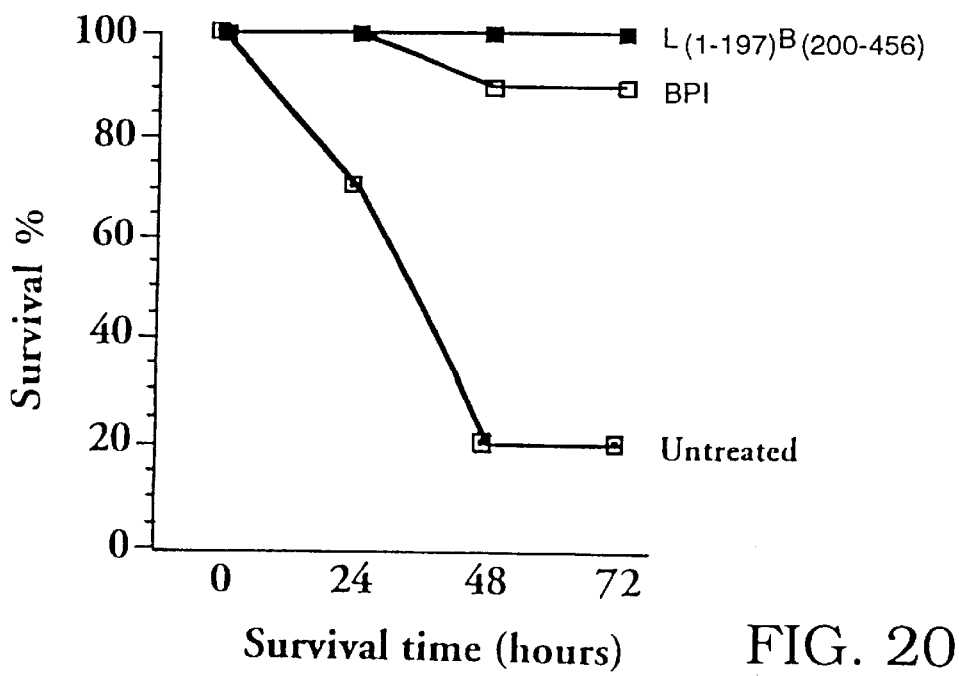
FIG. 20 is a graph showing the protective effects of $L_{1-197}B_{200-456}$ (NCY118) to endotoxin challenge in mice.

The results are shown in FIG. 20. BPI and $L_{1-197}B_{200-456}$ provided 90% to 100% survival, respectively, at the 72 hour end point. No further mortality was noted at seven days post-challenge. The untreated control group had a survival rate of 20%. The survival rates of the treated groups were statistically significant compared to the control group (p<0.001 for the $L_{1-197}B_{200-456}$ group and p=0.003 for the BPI group determined by Fisher's exact test). These results indicate that $L_{1-197}B_{200-456}$ is as effective as BPI in this endotoxin challenge model in vivo. Example 18: Protection Against Endotoxin Challenge in Mice The ability of the recombinant, endotoxin-neutralizing proteins $B_{(1-41)}L_{(1-199)}B_{(1-456)}$, $L_{(1-164)}B_{(200-456)}$, $B_{(1-175)}B_{(200-456)}$, $B_{(1-236)}$, and $B_{(1-190)}$ to protect mice against endotoxin challenge was carried out as described in Example 17 above. Protection by these proteins was compared to the protection provided by BPI or saline. The results of these studies are shown in Table 13.

TABLE 13

| | Compound | Lot # | Number of Survivors/10 at Time (hours) | | | | | | | |
|---|---|---|---|---|---|---|---|---|---|---|
| | | | 0 | 12 | 18 | 24 | 36 | 48 | 60 | 72 |
| Group 1 | native BPI | 149724 | 10 | 10 | 10 | 10 | 10 | 9 | 9 | 9 |
| Group 2 | $B_{(1-41)}L_{(1-199)}B_{(1-456)}$ | 162303 | 10 | 10 | 10 | 10 | 9 | 9 | 8 | 8 |
| Group 3 | $L_{(1-164)}B_{(200-456)}$ | 164325 | 10 | 10 | 9 | 9 | 8 | 8 | 7 | 7 |
| Group 4 | $L_{(1-175)}B_{(200-456)}$ | 164326 | 10 | 10 | 10 | 10 | 10 | 10 | 10 | 10 |
| Group 5 | $B_{(1-236)}$ | 159695 | 8 | 7 | 5 | 4 | 1 | 0 | 0 | 0 |
| Group 6 | $B_{(1-190)}$ | 159699 | 10 | 9 | 8 | 6 | 6 | 6 | 5 | 5 |
| Group 7 | Saline | | 10 | 8 | 7 | 6 | 4 | 3 | 3 | 3 |

Each animal received 35 mg/kg LPS in 0.1 ml, followed immediately by 5 mg/kg of the indicated compound in 0.1 ml. Survival was monitored at each time point indicated.

Example 19: Detection of a Gram-negative Infection in a Patient

A blood sample of about 1 ml to 5 ml is drawn from a patient suspected of having a Gram-negative infection. The blood sample is treated with citrate anti-coagulant and plasma is separated from the blood cells by centrifugation.

The plasma is then diluted in a series of 10-fold dilutions in assay buffer (pyrogen-free TBS+1 mg/ml low endotoxin BSA, and 0.05% Tween-20). The diluted plasma samples are then mixed with a known amount of biotinylated RENP. A series of control samples containing known amounts of biotinylated RENP in assay buffer is included in the assay as quantitative and negative controls.

The test and control samples are then applied to the wells of a microtiter plate having bound LPS. The LPS-bound microtiter wells are prepared by incubation with 1 or 4 μg of S. Minnesota R595 Re LPS (LIST Biological Labs, Inc., #304) in 50 mM borate pH 9.5–9.8+20–25 mM EDTA overnight at 37° C. Blank, non-LPS coated wells are included on each plate as controls for non-specific binding. The plates are then washed extensively under running distilled deionized water, then dried at 37° C. The assay wells are subsequently blocked for 60 minutes at 37° C. with 1–2% very low endotoxin BSA (Sigma, St. Louis, Mo.) prepared in pyrogen-free Tris-buffered saline (50 mM Tris pH 7.4+150 mM NaCl).

The test and control samples are incubated for a time sufficient for binding of the RENP in the samples to the LPS bound to the microtiter wells, generally about 2–3 hours at 37° C. in a total volume of 100 μl/well. After incubation, the wells are washed four times with assay buffer, and the plates are developed with streptavidin conjugated to alkaline phosphatase followed by 100 μl of PNP substrate solution freshly prepared from two 5 mg tablets dissolved in 10 ml substrate buffer. Substrate buffer is prepared with 24.5 mg $MgCl_2$, 48 ml diethanolamine, brought up to 400 ml, pH adjusted to 9.8 and volume brought up to 500 ml. Absorbances are read at 405 nm on a microplate reader.

If the level of biotinylated RENP bound to the wells of the test sample is significantly less than the level of biotinylated RENP bound to the negative control sample, then the patient has endotoxin circulating in the bloodstream which is generally associated with a Gram-negative infection. Moreover, the level of RENP binding in the test sample is compared to the levels of RENP binding in the quantitative controls, each of which are representative of varying degrees of severity of Gram-negative infection in a patient. The level of binding of the test sample is thus compared to the levels of binding of the quantitative samples to determine a degree of severity of infection.

Example 20: Detection of a Gram-negative Infection in vivo

RENP is detectably labeled with $^{125}I$ using methods well known in the art. Approximately 100 μg of an $^{125}I$-labeled RENP is injected intravenously into a patient suspected of having a Gram-negative infection in an organ, e.g., the liver. After allowing a time sufficient for circulation of the $^{125}I$-labeled RENP to the suspected site of infection, the abdomen of the patient is fluoroscoped or X-rayed 2 to 3 times so as to include various perspectives. The X-ray is then examined to identify sites of binding of the RENP by virtue of an abnormally darkened section on the X-ray. Upon identification of the site of infection, the clinician designs an appropriate therapeutic regimen.

Following procedures similar to those described above, other recombinant, LPS-binding proteins can be produced and used in diagnostic methods and methods of treatment according to the invention.

The invention now being fully described, it will be apparent to one of ordinary skill in the art that many changes and modifications can be made thereto without departing from the spirit or scope of the appended claims.

What is claimed is:

1. An isolated DNA molecule encoding a recombinant endotoxin binding polypeptide selected from the group consisting of:

(a) $L_{1-59}B_{60-456}$ wherein $L_{1-59}$ is the LBP sequence of amino acids corresponding to amino acids 1 to 59 of SEQ ID NO:2 and $B_{60-456}$ is the BPI sequence of amino acids corresponding to amino acids 60 to 456 of SEQ ID NO:4 or 16;

(b) $L_{1-134}B_{135-456}$ wherein $L_{1-134}$ is the LBP sequence of amino acids corresponding to amino acids 1 to 134 of SEQ ID NO:2 or 8 and $B_{135-456}$ is the BPI sequence of amino acids corresponding to amino acids 135 to 456 of SEQ ID NO:4 or 16;

(c) $L_{1-275}B_{278-456}$ wherein $L_{1-275}$ is the LBP sequence of amino acids corresponding to amino acids 1 to 275 of SEQ ID NO:2, 8 or 12 and $B_{278-456}$ is the BPI sequence of amino acids corresponding to amino acids 278 to 456 of SEQ ID NO:4 or 16;

(d) $L_{1-359}B_{360-456}$ wherein $L_{1-359}$ is the LBP sequence of amino acids corresponding to amino acids 1 to 359 of SEQ ID NO:2, 8 or 12 and $B_{360-456}$ is the BPI sequence of amino acids corresponding to amino acids 360 to 456 of SEQ ID NO:4;

(e) $L_{1-197}B_{200-456}$ wherein $L_{1-197}$ is the LBP sequence of amino acids corresponding to amino acids 1 to 197 of SEQ ID NO:2 or 12 and $B_{200-456}$ is the BPI sequence of amino acids corresponding to amino acids 200 to 456 of SEQ ID NO:4 or 16;

(f) $L_{1-197(I43->V)}B_{200-456(N206->D)}$ wherein $L_{1-197(I43->V)}$ is the LBP sequence of amino acids corresponding to amino acids 1 to 197 of SEQ ID NO:2, 8 or 12, except that Ile at the position corresponding to amino acid 43 has been substituted by Val, and $B_{200-456(N206->D)}$ is the BPI sequence of amino acids corresponding to amino acids 200 to 456 of SEQ ID NO:4 or 16, except that Asn at the position corresponding to amino acid 206 has been substituted by Asp;

(g) $L_{1-199}B_{200-456(S351->A)}$ wherein $L_{1-199}$ is the LBP sequence of amino acids corresponding to amino acids 1 to 199 of SEQ ID NO:2, 8 or 12 and $B_{200-456(S351->A)}$ is the BPI sequence of amino acids corresponding to amino acids 200 to 456 of SEQ ID NO:4 or 16, except that Ser at the position corresponding to amino acid 351 has been substituted by Ala;

(h) $L_{1-199}Fc$ wherein $L_{1-199}$ is the LBP sequence of amino acids corresponding to amino acids 1 to 199 of SEQ ID NO:2, 8 or 12, and an Fc portion of an immunoglobulin;

(i) LBP that is the amino acid sequence corresponding to amino acids 1 to 456 of SEQ ID NO:2 or 12;

(j) $B_{(S351->A)}$ is the BPI sequence corresponding to amino acids 1 to 456 of SEQ ID NO:4 or 16, except that Ser at the position corresponding to amino acid 351 has been substituted by Ala;

(k) $B_{(DS200->DP)}$ is the BPI sequence corresponding to amino acids 1 to 456 of SEQ ID NO:4 or 16, except that Ser at the position corresponding to amino acid 201 has been substituted by Pro;

(l) $B_{1-199}L_{200-456}$ wherein $B_{1-199}$ is the BPI sequence of amino acids corresponding to amino acids 1 to 199 of SEQ ID NO:4 and $L_{200-456}$ is the LBP sequence of amino acids corresponding to amino acids 200-456 of SEQ ID NO:2 or 8; and (m) $L_{1-199}$ is the LBP sequence corresponding to amino acids 1-199 of SEQ ID NO: 2, 8, or 12.

2. A vector comprising the DNA of claim 1.

3. A transformed host cell comprising the DNA of claim 1.

4. A method for producing a recombinant endotoxin binding polypeptide, said method comprising the steps of, (a) culturig a transformed host cell comprising DNA encoding a recombinant endotoxin binding polypeptide according to claim 1, said DNA being operably linked to a promoter for expression of the polypeptide encoded by the DNA, said culturing being under conditions allowing expression of said polypeptide; and (b) isolating the recombinant endotoxin binding polypeptide produced.

5. An isolated DNA molecule encoding a recombinant endotoxin binding polypeptide selected from the group consisting of:

(a) $L_{1-134}$ $B_{1-361}L_{360-456}$ wherein $L_{1-134}$ is the LBP sequence of amino acids corresponding to amino acids 1 to 134 of SEQ ID NO:2 or 8 and $B_{136-361}$ is the BPI sequence of amino acids corresponding to amino acids 136 to 361 of SEQ ID NO:4 or 16 and $L_{360-456}$ is the LBP sequence of amino acids corresponding to amino acids 360 to 456 of SEQ ID NO:2;

(b) $L_{1-134}B_{136-275}L_{274-456}$ wherein $L_{1-134}$ is the LBP sequence of amino acids corresponding to amino acids 1 to 134 of SEQ ID NO:2 or 8 and $B_{136-275}$ is the BPI sequence of amino acids corresponding to amino acids 136 to 275 of SEQ ID NO:4 and $L_{274-456}$ is the LBP sequence of amino acids corresponding to amino acids 274 to 456 of SEQ ID NO:2 or 8;

(c) $L_{1-198}B_{202-275}L_{274-456}$ wherein $L_{1-198}$ is the LBP sequence of amino acids corresponding to amino acids 1 to 198 of SEQ ID NO:2, 8 or 12 and $B_{202-275}$ is the BPI sequence of amino acids corresponding to amino acids 202 to 275 of SEQ ID NO:4 and $L_{274-456}$ is the LBP sequence of amino acids corresponding to amino acids 274 to 456 of SEQ ID NO:2;

(d) $L_{1-198}B_{202-361}L_{360-456}$ wherein $L_{1-198}$ is the LBP sequence of amino acids corresponding to amino acids 1 to 198 of SEQ ID NO:2, 8 or 12 and $B_{202-361}$ is the BPI sequence of amino acids corresponding to amino acids 202 to 361 of SEQ ID NO:4 or 16 and $L_{360-456}$ is the LBP sequence of amino acids corresponding to amino acids 360 to 456 of SEQ ID NO:2;

(e) $L_{1-198}B_{201-456}Fc$ wherein $L_{1-198}$ is the LBP sequence of amino acids corresponding to amino acids 1 to 198 of SEQ ID NO:2, 8 or 12 and $B_{201-456}Fc$ is the BPI sequence of amino acids corresponding to amino acids 201 to 456 of SEQ ID NO:4 or 16, and an Fc portion of an immunoglobulin;

(f) $B_{(K77->S)(K86->R)(K90->R)(K96->S)(K118->L)(K127->R)}$ is the BPI sequence corresponding to amino acids 1 to 456 of SEQ ID NO:4 or 16, except that it has the following amino acid substitutions: (1) $Lys^{77}$ to Ser, (2) $Lys^{86}$ to Arg, (3) $Lys^{90}$ to Arg, (4) $Arg^{96}$ to Ser, (5) $Lys^{118}$ to Leu, and (6) $Lys^{127}$ to Arg;

(g) $B_{(K27->S)(K30->L)(K33->T)(K42->R)(K44->P)(K48->R)(R59->H)}$ is the BPI sequence corresponding to amino acids 1 to 456 of SEQ ID NO:4 or 16, except that it has the following amino acid substitutions: (1) $Lys^{27}$ to Ser, (2) $Lys^{30}$ to Leu, (3) $Lys^{33}$ to Thr, (4) $Lys^{42}$ to Arg, (5) $Lys^{44}$ to Pro, (6) $Lys^{48}$ to Arg, and (7) $Arg^{59}$ to His;

(h) $B_{(K148->G)(K150->D)(K160->N)(K161->Q)(R167->Q)(K169->V)(K177->M)(K185->D)(K198->E)}$ is the BPI sequence corresponding to amino acids 1 to 456 of SEQ ID NO:4 or 16, except that it has the following amino acid substitutions: (1) $Lys^{148}$ to Gly, (2) $Lys^{150}$ to Asp, (3) $Lys^{160}$ to Asn, (4) $Lys^{161}$ to Gln, (5) $Arg^{167}$ to Gln, (6) $Lys^{169}$ to Val, (7) $Lys^{177}$ to Met (8) $Lys^{185}$ to Asp, and (9) $Lys^{198}$ to Glu;

(i) $B_{(K77->S)(K86->R)(K90->R)(R96->S)(K118->L)(K127->R)(K148->G)(K150->D)(K160->N)(K161->Q)(R167->Q)(K169->V)(K177->M)(K185->D)(K198->E)}$ is the BPI sequence corresponding to amino acids 1 to 456 of SEQ ID NO:4 or 16, except that it has the following amino acid substitutions: (1) $Lys^{77}$ to Ser, (2) $Lys^{86}$ to Arg, (3) $Lys^{90}$ to Arg, (4) $Arg^{96}$ to Ser, (5) $Lys^{118}$ to Leu and (6) $Lys^{127}$ to Arg, (7) $Lys^{148}$ to Gly, (8) $Lys^{150}$ to Asp, (9) $Lys160$ to Asn, (10) $Lys^{161}$ to Gln, (11) $Arg^{167}$ to Gln, (12) $Lys^{169}$ to Val, (13) $Lys^{177}$ to Met, (14) $Lys^{185}$ to Asp, and (15) $Lys^{198}$ to Glu;

(j) $L_{(S77->K)(R86->K)(R90->K)(S96->K)(L118->K)(R126->K)}$ is the LBP sequence corresponding to amino acids 1 to 456 of SEQ ID NO:2, 8 or 12, except that it has the following amino acid substitutions: (1) $Ser^{77}$ to Lys, (2) $Arg^{86}$ to Lys, (3) $Arg^{90}$ to Lys, (4) $Ser^{96}$ to Lys, (5) $Leu^{118}$ to Lys, and (6) $Arg^{126}$ to Lys;

(k) $L_{(G147->K)(D148->K)(N158->K)(Q159->K)(Q165->R)(V167->K)(M175->K)(D183->K)(E196->K)}$ is the LBP sequence corresponding to amino acids 1 to 456 of SEQ ID NO:2, 8 or 12, except that it has the following amino acid substitutions: (1) $Gly^{147}$ to Lys, (2) $Asp^{148}$ to Lys, (3) $Asn^{158}$ to Lys, (4) $Gln^{159}$ to Lys, (5) $Gln^{165}$ to Arg, (6) $Val^{167}$ to Lys, (7) $Met^{175}$ to Lys, (8) $Asp^{183}$ to Lys, and (9) $Glu^{196}$ to Lys; and (l) $L_{(S77->K)(R86->K)(R90->K)(S96->K)(L118->K)(R126->K)(G147->K)(D148->K)(N158->K)(Q159->K)(Q165->R)(V167->K)(M175->K)(D183->K)(E196->K)}$ is the LBP sequence corresponding to amino acids 1 to 456 of SEQ ID NO:2, 8 or 12, except that it has the following amino acid substitutions: (1) $Ser^{77}$ to Lys, (2) $Arg^{86}$ to Lys, (3) $Arg^{90}$ to Lys, (4) $Ser^{96}$ to Lys, (5) $Leu^{118}$ to Lys, and (6) $Arg^{126}$ to Lys, (7) $Gly^{147}$ to Lys, (8) $Asp^{148}$ to Lys, (9) $Asn^{158}$ to Lys, (10) $Gln^{159}$ to Lys, (11) $Gln^{165}$ to Arg, (12) $Val^{167}$ to Lys, (13) $Met^{175}$ to Lys, (14) $Asp183$ to Lys, and (15) $Glu^{196}$ to Lys.

6. A vector comprising the DNA of claim 5.

7. A transformed host cell comprising the DNA of claim 5.

8. A method for producing a recombinant endotoxin binding polypeptide, said method comprising the steps of: (a) culturing a transfonned host cell comprising DNA encoding a recombinant endotoxin binding polypeptide according to claim 5, said DNA being operably linked to a promoter for expression of the polypeptide encoded by the DNA, said culturing being under conditions allowing expression of said polypeptide; and (b) isolating the recombinant endotoxin binding polypeptide produced.

9. An isolated DNA molecule encoding a recombinant endotoxin binding polypeptide selected from the group consisting of:

(a) $L_{1-164}B_{200-456}$ wherein $L_{1-164}$ is the LBP sequence of amino acids corresponding to amino acids 1 to 164 of SEQ ID NO:2, 8 or 12 and $B_{200-456}$ is the BPI sequence of amino acids corresponding to amino acids 200 to 456 of SEQ ID NO:4 or 16;

(b) $L_{1-175}B_{200-456}$ wherein $L_{1-175}$ is the LBP sequence of amino acids cotresponding to amino acids 1 to 175 of SEQ ID NO:2, 8 or 12 and $B_{200-456}$ is the BPI sequence of amino acids corresponding to amino acids 200 to 456 of SEQ ID NO:4 or 16; and (c) $B_{1-41}L_{42-199}B_{200-456}$ wherein $B_{1-41}$ is the BPI sequence corresponding to amino acids 1 to 41 of SEQ ID NO:4, $L_{42-199}$ is the LBP sequence corresponding to amino acids 42 to 199 of SEQ ID NO:2, 8 or 12, and $B_{200-456}$ is the BPI sequence corresponding to amino acids 200 to 456 of SEQ ID NO: 4 or 16.

10. A vector coming the DNA of claim 9.

11. A transfonned host cell comprising the DNA of claim 9.

12. A method for producing a recombinant endotoxin binding polypeptide, said method comprising the steps of: (a) culturing a transformed host cell comprising DNA encoding a recombinant endotoxin binding polypeptide according to claim 9, said DNA being operably linked to a promoter for expression of the polypeptide encoded by the DNA, said culturing being under conditions allowing expression of said polypeptide; and (b) isolating the recombinant endotoxin binding polypeptide produced.

* * * * *